United States Patent
Heckel et al.

(10) Patent No.: US 10,155,749 B2
(45) Date of Patent: Dec. 18, 2018

(54) SUBSTITUTED BENZIMIDAZOLIUM COMPOUNDS USEFUL IN THE TREATMENT OF RESPIRATORY DISEASES

(71) Applicant: Boehringer Ingelheim International GmbH, Ingelheim am Rhein (DE)

(72) Inventors: Armin Heckel, Biberach an der Riss (DE); Dieter Hamprecht, Pozzolengo (IT); Joerg Kley, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/542,894

(22) PCT Filed: Jan. 7, 2016

(86) PCT No.: PCT/EP2016/050167
§ 371 (c)(1),
(2) Date: Jul. 11, 2017

(87) PCT Pub. No.: WO2016/113167
PCT Pub. Date: Jul. 21, 2016

(65) Prior Publication Data
US 2018/0105512 A1   Apr. 19, 2018

(30) Foreign Application Priority Data
Jan. 12, 2015 (EP) .................... 15150826

(51) Int. Cl.
| | | |
|---|---|---|
| C07D 403/12 | (2006.01) |
| A61K 31/497 | (2006.01) |
| A61K 31/5377 | (2006.01) |
| A61K 31/551 | (2006.01) |
| A61K 31/675 | (2006.01) |
| A61K 45/06 | (2006.01) |
| C07C 53/18 | (2006.01) |
| C07D 401/14 | (2006.01) |
| C07D 405/14 | (2006.01) |
| C07F 9/53 | (2006.01) |
| C07D 403/14 | (2006.01) |
| C07F 9/6558 | (2006.01) |
| C07F 7/18 | (2006.01) |
| A61P 11/00 | (2006.01) |
| C07D 413/14 | (2006.01) |

(52) U.S. Cl.
CPC .......... *C07D 403/12* (2013.01); *A61P 11/00* (2018.01); *C07D 401/14* (2013.01); *C07D 403/14* (2013.01); *C07D 405/14* (2013.01); *C07D 413/14* (2013.01); *C07F 7/1856* (2013.01); *C07F 9/5304* (2013.01); *C07F 9/65583* (2013.01)

(58) Field of Classification Search
CPC .. C07D 403/12; C07D 401/14; C07D 405/14; C07C 53/18; A61K 31/497; A61K 31/5377; A61K 31/551; A61K 31/675; A61K 45/06
USPC ........................................................ 514/80
See application file for complete search history.

(56) References Cited

U.S. PATENT DOCUMENTS

2015/0018313 A1   1/2015   Kley et al.

FOREIGN PATENT DOCUMENTS

| WO | 11079087 A1 | 6/2011 | |
| WO | WO-2011079087 A1 * | 6/2011 | ......... A61K 31/4184 |
| WO | 2015007516 A1 | 1/2015 | |

OTHER PUBLICATIONS

Ertl et al., "Fast Calculation of Molecular Polar Surface Area as a Sum Fragment-Based Contributions and Its Application to the Prediction of Drug Transport Properti ES", Journal of Medicinal Chemistry, 2000, vol. 43, No. 20, pp. 3714-3717.
International Search Report and Written Opinion for corresponding application PCT/EP2016/050167, dated Feb. 23, 2016.
Schoenberger et al., "Novel small molecule epithelial sodium channel inhibitors as potential therapeutics in cystic fibrosis—a patent evaluation", Expert Opinion on Therapeutic Patents, Informa Healthcare, 2013, vol. 23, No. 10, pp. 1383-1389.

* cited by examiner

*Primary Examiner* — Kahsay Habte
(74) *Attorney, Agent, or Firm* — Philip I. Datlow

(57) ABSTRACT

The present invention relates to compounds of formula (I), or the tautomers or pharmacologically acceptable acid addition salts thereof, characterized by a topological polar surface area value (TPSA) of at least 145, wherein $R^1$, $R^2$, $R^3$, $R^4$, X, and $Z^-$ have one of the meanings as defined in the specification, to the use of compounds of formula (I) as a medicament, to pharmaceutical composition comprising at least one compound of formula (I), as well as to medicament combinations containing one or more compounds of formula (I).

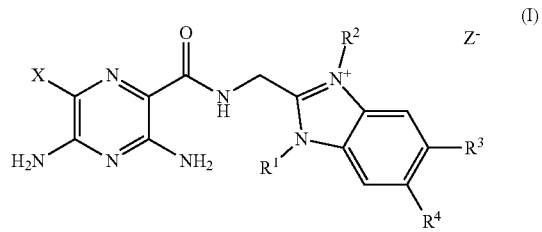

12 Claims, No Drawings

SUBSTITUTED BENZIMIDAZOLIUM COMPOUNDS USEFUL IN THE TREATMENT OF RESPIRATORY DISEASES

FIELD OF THE INVENTION

The present invention relates to compounds of formula (I), or the tautomers or pharmacologically acceptable acid addition salts thereof,

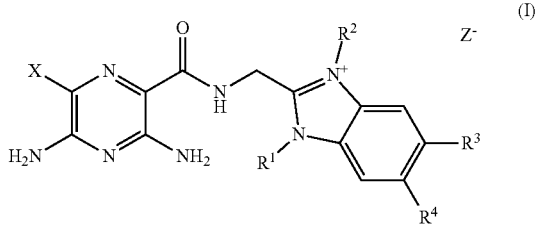

characterized by a topological polar surface area value (TPSA) of at least 145, wherein $R^1$, $R^2$, $R^3$, $R^4$, X, and $Z^-$ have one of the meanings as defined in the specification, to the use of compounds of formula (I) as a medicament, to pharmaceutical compositions comprising at least one compound of formula (I), as well as to medicament combinations containing one or more compounds of formula (I).

BACKGROUND TO THE INVENTION

WO2011079087 discloses compounds of similar structure showing ENaC (Epithelial Sodium Channel) inhibitor activity.

The problem of the present invention is to prepare new compounds which may be used therapeutically for the treatment of pathophysiological processes treatable by the blockade of an epithelial sodium channel, particularly for the treatment of the lungs and airways. The new compounds of the present invention exhibit a longer lasting activity in topical lung treatment. The new compounds of the present invention further exhibit a reduced permeability being beneficial for topical lung treatment.

DETAILED DESCRIPTION OF THE INVENTION

The present invention relates to compounds of formula (I), or the tautomers or pharmacologically acceptable acid addition salts thereof,

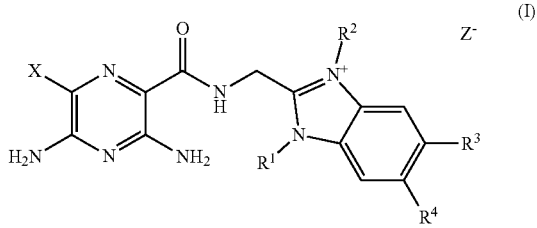

wherein
$R^1$ and $R^2$ are independently selected from $C_1$-$C_6$-alkyl, wherein $C_1$-$C_6$-alkyl may be substituted by hydroxy, $C_1$-$C_4$-alkoxy, or $C_3$-$C_7$-cycloalkyl;
X is Cl or Br; and $Z^-$ is chloride, bromide, iodide, hydroxide, hydrogensulfate, sulfate, nitrate, phosphate, formate, acetate, trifluoroacetate, fumarate, citrate, tartrate, oxalate, succinate, mandelate, methanesulfonate or p-toluenesulfonate; or Z— may be absent if the remaining compound of formula (I) carries at least one negatively charged substituent $R^3$ or $R^4$;

wherein at least one of $R^3$ or $R^4$ is independently selected from a substituent —C(O)$NR_aR_b$, —$CH_2$—C(O)$NR_aR_b$, or —O—$CH_2$—C(O)$NR_aR_b$, wherein $R^a$ is H, methyl, ethyl, hydroxyethyl, or hydroxypropyl, and $R^b$ is selected from $C_1$-$C_2$-alkoxy-$C_2$-$C_3$-alkyl, amino-$C_2$-$C_3$-alkyl, 4-piperidinyl, 1-acetyl-4-piperidinyl, dimethylamino-$C_2$-$C_3$-alkyl, (3-hydroxy-1-pyridinylium)-$C_2$-$C_3$-alkyl, acetylamino-$C_2$-$C_3$-alkyl, 1-($C_1$-$C_6$-alkyl)-4-piperidinyl, 1-($C_1$-$C_4$-alkoxy-carbonyl)-4-piperidinyl, $C_1$-$C_3$-alkylsulfonylamino-($C_2$-$C_3$-alkyl), 3-hydroxy-5-pyridyl, 1-(ethylaminocarbonylmethyl)-4-piperidinyl, 3-benzyloxy-5-pyridyl, 3-hydroxy-6-methyl-2-pyridylmethyl and 3-hydroxy-2-pyridylmethyl-, or wherein $R^a$ and $R^b$ together with the nitrogen atom they are attached to form a group selected from 1-(2-pyridyl)-4-piperazinyl, 1-($C_1$-$C_4$-alkoxycarbonyl)-4-piperazinyl, 1-(1-morpholinylcarbonyl)-4-piperazinyl,
1-(2-pyridylacetyl)-4-piperazinyl, 1-(3-hydroxy-5-pyridycarbonyl)-4-piperazinyl, and 1-acetyl-4-piperazinyl, or wherein at least one of $R^3$ or $R^4$ is independently selected from hydroxycarbonylyl) methoxy, N-morpholinylcarbonyl, 3,4-dihydroxypyrrolidin-1-yl, 4-hydroxytetrahydrofur-3-yloxy, tert-butoxycarbonylmethoxy, (3-hydroxy-1-pyridinylium)-$C_2$-$C_3$-alkoxy, $(CH_3)_3N^+$—$(CH_2)_3$—P(O)$(O^-)$—O—$(CH_2)_2$—O—, ($C_1$-$C_5$-alkylcarbonyl)(($CH_3)_2$P(O)$CH_2$)N—$(CH_2)_2$—O—, 1-piperazinylcarbonyl-$(CH_2)_m$—, or 1-methyl-4-piperazinyl-carbonyl-$(CH_2)_m$—, wherein m is 0, 1 or 2, or wherein at least one of $R^3$ or $R^4$ is independently selected from one of the following substituents:

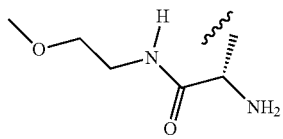
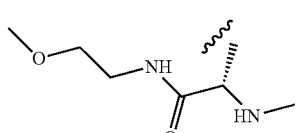
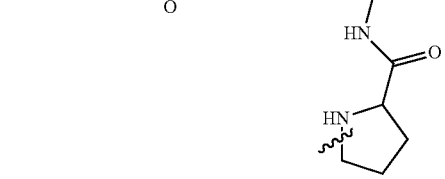

3
-continued

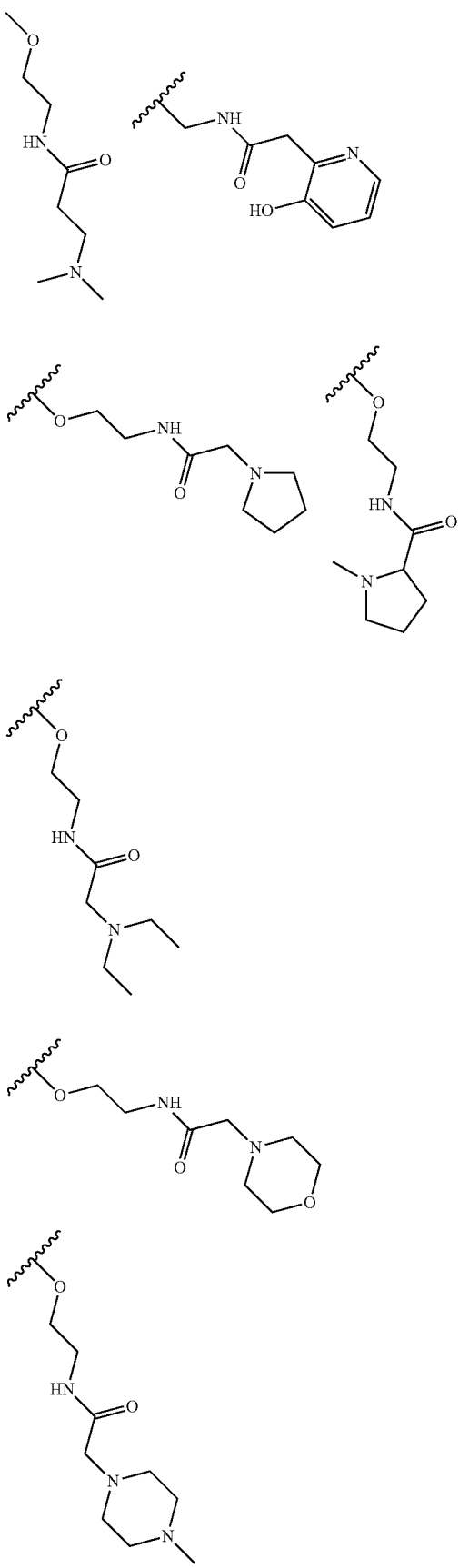

4
-continued

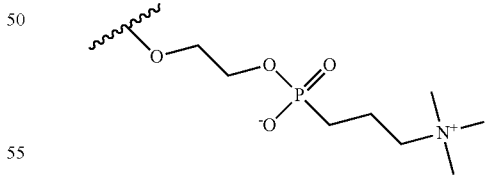

wherein ⌇ denotes the point of attachment; and wherein the remaining substituent $R^3$ or $R^4$ may additionally be selected from H, F, $C_1$-$C_6$-alkoxy, di($C_1$-$C_6$-alkyl)amino, $C_1$-$C_6$-alkylaminocarbonyl, $C_1$-$C_6$-alkylaminocarbonyl-methoxy, di($C_1$-$C_6$-alkyl)aminocarbonyl, and N-morpholino;

provided that if one of $R^3$ or $R^4$ is at least one of $R^1$ or $R^2$ is $C_3$-$C_7$-cycloalkyl-$C_1$-$C_6$-alkyl; and provided that if one of $R^3$ or $R^4$ is N-morpholinocarbonyl the remaining substituent $R^3$ or $R^4$ is different from H, F or $C_1$-$C_6$-alkylaminocarbonyl; and provided that at least one of $R^3$ or $R^4$ is different from H, hydroxycarbonyl, (hydroxycarbonyl)methoxy and tert-butoxycarbonylmethoxy.

The compounds of formula (I) according to the present invention are characterized by a topological polar surface area value (TPSA) of at least 145. The term "topological polar surface area" as used herein refers to a value calculated as described in Ertl P. et al., J. Med. Chem, 43 (2000), 3714-3717. Suitable compounds of formula (I) will usually have a TPSA value in the range of from 145 to 250.

The present invention relates to compounds of formula (I) as defined herein or the tautomers or pharmacologically acceptable acid addition salts thereof for use as a medicament.

The present invention further relates to compounds of formula (I) as defined herein or the tautomers or pharmacologically acceptable acid addition salts thereof for use in the treatment of a disease selected from among respiratory diseases or complaints and allergic diseases of the airways.

The present invention further relates to compounds of formula (I) as defined herein or the tautomers or pharmacologically acceptable acid addition salts thereof for use in the treatment of a disease selected from among chronic bronchitis, acute bronchitis, bronchitis caused by bacterial or viral infection or fungi or helminths, allergic bronchitis, toxic bronchitis, chronic obstructive bronchitis (COPD), asthma (intrinsic or allergic), pediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases, alveolitis, hyperreactive airways, nasal polyps, pulmonary oedema, pneumonitis of different origins, and dry eyes.

The present invention further relates to pharmaceutical compositions comprising at least one compound of formula (I) as defined herein or the tautomers or pharmacologically acceptable acid addition salts thereof and a pharmaceutically acceptable carrier.

The present invention further relates to medicament combinations which contain, besides one or more compounds of formula (I) as defined herein or the tautomers or pharmacologically acceptable acid addition salts thereof as further active substances one or more compounds selected from among the categories of further ENaC inhibitors, betamimetics, anticholinergics, corticosteroids, PDE4-inhibitors, LTD4-antagonists, EGFR-inhibitors, dopamine agonists, H1 antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators or double or triple combinations thereof.

The compounds of formula (I) or the pharmaceutically acceptable salts thereof as defined herein are particularly suitable for the treatment of pathophysiological processes treatable by the blockade of an epithelial sodium channel, particularly for the treatment of the lungs and airways.

Accordingly the present invention further relates to the compound of formula (I) as defined herein or a pharmaceutically acceptable salt thereof for use as a medicament.

The present invention further relates to the compound of formula (I) as defined herein or a pharmaceutically acceptable salt thereof for use in the treatment of a disease selected from among respiratory diseases or complaints and allergic diseases of the airways.

The present invention particularly relates to compounds of formula (I) or pharmaceutically acceptable salts thereof for use in the treatment of a disease selected from among chronic bronchitis, acute bronchitis, bronchitis caused by bacterial or viral infection or fungi or helminths, allergic bronchitis, toxic bronchitis, chronic obstructive bronchitis (COPD), asthma (intrinsic or allergic), paediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases, alveolitis, hyperreactive airways, nasal polyps, pulmonary oedema, pneumonitis of different origins, and dry eyes, more particularly for use in the treatment of a disease selected from chronic bronchitis, acute bronchitis, bronchitis, chronic obstructive bronchitis (COPD), asthma (intrinsic or allergic), cystic fibrosis and paediatric asthma, preferably chronic bronchitis, COPD and cystic fibrosis.

The present invention further relates to pharmaceutical compositions comprising at least one compound of formula (I) or a pharmaceutically acceptable salt thereof as defined herein and a pharmaceutically acceptable carrier.

The present invention further relates to medicament combinations which contain, besides one or more compounds of formula (I) or a pharmaceutically acceptable salt thereof as defined herein, as further active substances, one or more compounds selected from among the categories of further ENaC inhibitors, betamimetics, anticholinergics, corticosteroids, PDE4-inhibitors, LTD4-antagonists, EGFR-inhibitors, dopamine ago-nists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators or double or triple combinations thereof.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, $H_2N$, OS, $O_2S$, NC (cyano), HOOC, $F_3C$ or the like, the skilled artisan can see the radical attachment point(s) to the molecule from the free valences of the group itself. For combined groups comprising two or more subgroups, the terminal term indicates the radical attachment point, for example, the substituent "aryl-$C_{1-3}$-alkyl" means an aryl group which is bound to a $C_{1-3}$-alkyl-group, the latter of which is bound to the core or to the group to which the substituent is attached.

In case a compound of the present invention is depicted in form of a chemical name and as a formula, in case of any discrepancy the formula shall prevail.

Many of the following terms may be used repeatedly in the definition of a formula or group and in each case have one of the meanings given above, independently of one another.

Unless specifically indicated, according to the invention a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The term "substituted" as used herein, means that any one or more hydrogens on the designated atom is replaced with a selection from the indicated group, provided that the designated atom's normal valence is not exceeded, and that the substitution results in a stable compound.

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds. For example the groups may comprise: Straight-chain or branched carbon chains, optionally interrupted by heteroatoms, optionally substituted by rings, heteroatoms or other common functional groups.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The phrase "pharmacologically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmacologically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)pyrrolidine, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamidobenzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a cationic group and optionally an additional basic or acidic moiety by conventional chemical methods. Generally, such salts can be prepared by reacting other salt forms of these compounds with a sufficient amount of the appropriate base or acid in water or in an organic diluent like ether, ethyl acetate, ethanol, isopropanol, or acetonitrile, or a mixture thereof. Moreover, counterions can generally be exchanged by ion exchange chromatography.

Salts of other acids than those mentioned above which for example are useful for purifying or isolating the compounds of the present invention (e.g. trifluoro acetate salts) also comprise a part of the invention.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C—$, $H_3C—CH_2—$, $H_3C—CH_2—CH_2—$, $H_3C—CH(CH_3)—$, $H_3C—CH_2—CH_2—CH_2—$, $H_3C—CH_2—CH(CH_3)—$, $H_3C—CH(CH_3)—CH_2—$, $H_3C—C(CH_3)_2—$, $H_3C—CH_2—CH_2—CH_2—CH_2—$, $H_3C—CH_2—CH_2—CH(CH_3)—$, $H_3C—CH_2—CH(CH_3)—CH_2—$, $H_3C—CH(CH_3)—CH_2—CH_2—$, $H_3C—CH_2—C(CH_3)_2—$, $H_3C—C(CH_3)_2—CH_2—$, $H_3C—CH(CH_3)—CH(CH_3)—$ and $H_3C—CH_2—CH(CH_2CH_3)—$.

The term "$C_{1-n}$-alkylene" wherein n is an integer 2 to n, either alone or in combination with another radical, denotes an acyclic, straight or branched chain divalent alkyl radical containing from 1 to n carbon atoms. For example the term $C_{1-4}$-alkylene includes $—CH_2—$, $—CH_2—CH_2—$, $—CH(CH_3)—$, $—CH_2—CH_2—CH_2—$, $—C(CH_3)_2—$, $—CH(CH_2CH_3)—$, $—CH(CH_3)—CH_2—$, $—CH_2—CH(CH_3)—$, $—CH_2—CH_2—CH_2—CH_2—$, $—CH_2—CH_2—CH$ (CH$_3$)—, —CH(CH$_3$)—CH$_2$—CH$_2$—, —CH$_2$—CH(CH$_3$)—CH$_2$—, —CH$_2$—C(CH$_3$)$_2$—, —C(CH$_3$)$_2$—CH$_2$—, —CH(CH$_3$)—CH(CH$_3$)—, —CH$_2$—CH(CH$_2$CH$_3$)—, —CH(CH$_2$CH$_3$)—CH$_2$—, —CH(CH$_2$CH$_2$CH$_3$)—, —CH(CH(CH$_3$))$_2$— and —C(CH$_3$)(CH$_2$CH$_3$)—.

By the term "C$_{1-6}$-alkoxy" (including those which are part of other groups) are meant branched and unbranched alkoxy groups with 1 to 6 carbon atoms and by the term "C$_{1-4}$-alkoxy" are meant branched and unbranched alkoxy groups with 1 to 4 carbon atoms. Alkoxy groups with 1 to 4 carbon atoms are preferred. Examples include: methoxy, ethoxy, propoxy, butoxy or pentoxy. The abbreviations OMe, OEt, OPr, etc. may optionally be used for the above-mentioned groups. Unless stated otherwise, the definitions propoxy, butoxy and pentoxy include all the possible isomeric forms of the respective groups. Thus for example propoxy includes n-propoxy and iso-propoxy, butoxy includes iso-butoxy, sec-butoxy and tert-butoxy etc.

The term "C$_{3-n}$-cycloalkyl", wherein n is an integer from 4 to n, either alone or in combination with another radical denotes a cyclic, saturated, unbranched hydrocarbon radical with 3 to n C atoms. For example the term C$_{3-7}$-cycloalkyl includes cyclopropyl, cyclobutyl, cyclopentyl, cyclohexyl and cycloheptyl.

In all cases of contradictions between structure and their naming, structure shall prevail.

Preferred Embodiments

One particular embodiment of the invention relates to compounds of formula (I) as defined herein or to the tautomers or pharmacologically acceptable acid addition salts thereof, wherein at least one of R$^3$ or R$^4$ is independently selected from a substituent —C(O)NR$_a$R$_b$ selected from

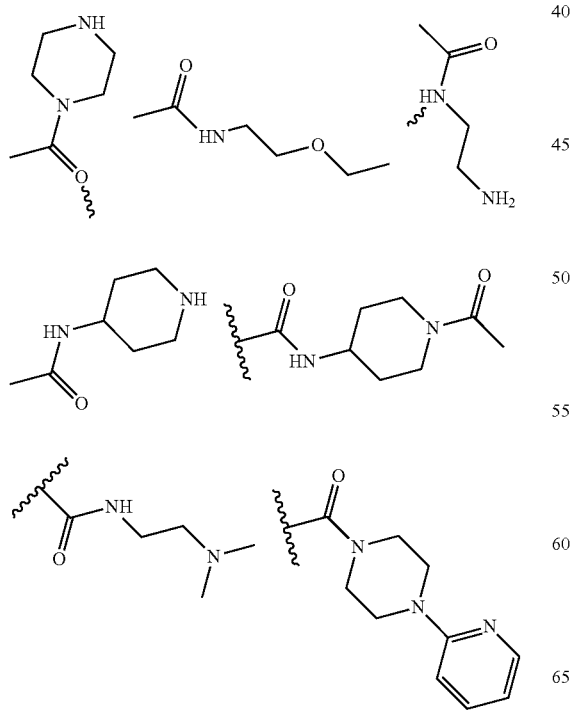
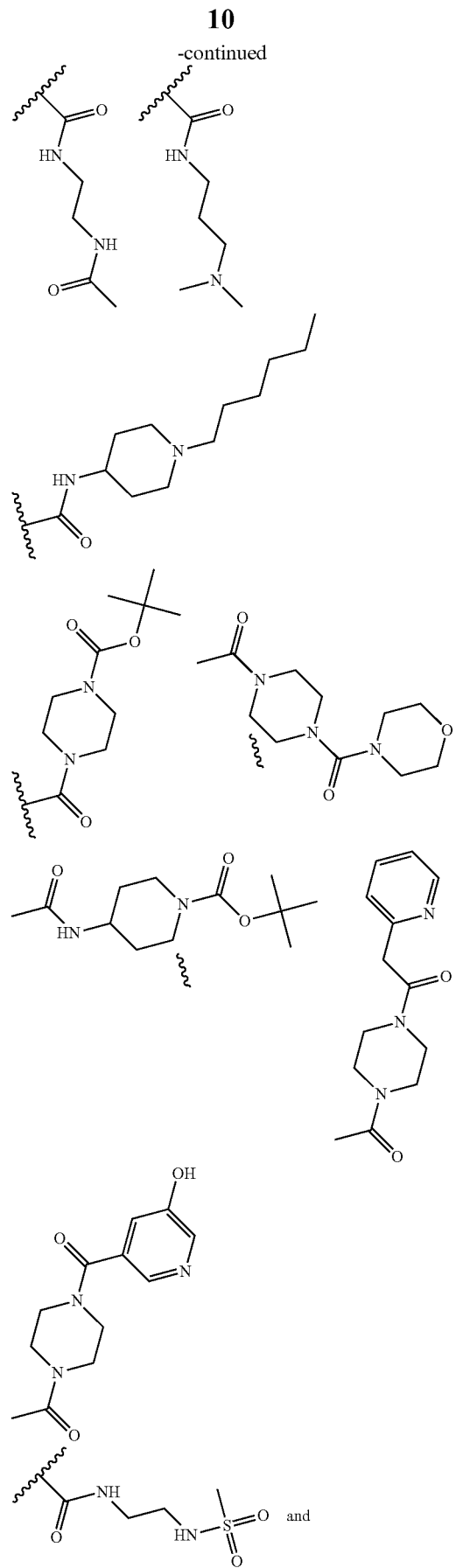

-continued

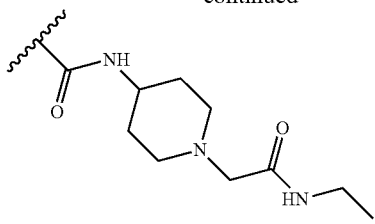

wherein ⚹ denotes the point of attachment.

Another particular embodiment of the invention relates to compounds of formula (I) as defined herein or to the tautomers or pharmacologically acceptable acid addition salts thereof, wherein at least one of $R^3$ or $R^4$ is independently selected from a substituent —$CH_2$—$C(O)NR_aR_b$, selected from

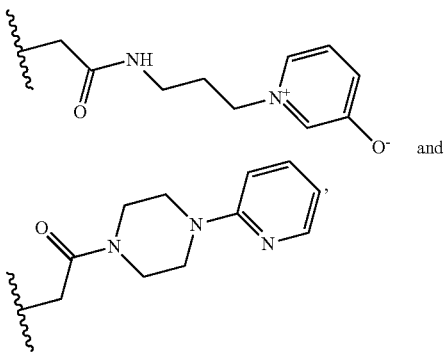

wherein ⚹ denotes the point of attachment.

Another particular embodiment of the invention relates to compounds of formula (I) as defined herein or to the tautomers or pharmacologically acceptable acid addition salts thereof, wherein at least one of $R^3$ or $R^4$ is independently selected from a substituent —O—$CH_2$—$C(O)NR_aR_b$ selected from

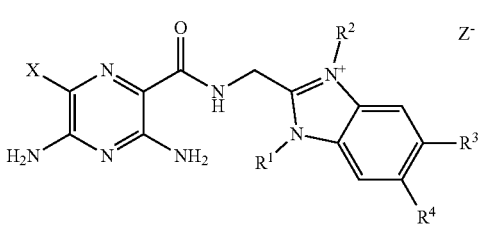

wherein \ denotes the point of attachment.

Another particular embodiment of the invention relates to compounds of formula (I) as defined herein or to the tautomers or pharmacologically acceptable acid addition salts thereof, wherein one of $R^3$ or $R^4$ is selected from (3-hydroxy-1-pyridinylium)ethoxy, 2-(N-(dimethylphosphinoylmethyl)-N-(3-methylbutanoyl)amino)ethyloxy, 2-(N-(dimethylphosphinoylmethyl)-N-(hexanoyl)amino)ethyloxy, piperazin-1-ylcarbonyl, and 1-methylpiperazin-4-yl-carbonyl-($CH_2$)—.

Another particular embodiment of the invention relates to compounds of formula (I) or to the tautomers or pharmacologically acceptable acid addition salts thereof as defined in the above embodiments, wherein the remaining substituent $R^3$ or $R^4$ is selected from H, F, ethoxy, n-pentyloxy, dimethylamino, ethylaminocarbonyl, ethylaminocarbonylmethoxy, n-hexyl(methyl)aminocarbonyl, and N-morpholino.

Another particular embodiment of the invention relates to compounds of formula (I) as defined herein or to the tautomers or pharmacologically acceptable acid addition salts thereof, wherein $R^1$ and $R^2$ are independently selected from methyl, ethyl, n-propyl, 2-hydroxyethyl, 2-hydroxypropyl, cyclopropylmethyl, and cyclohexylmethyl.

The present invention relates to compounds of formula (I) as defined herein or to the tautomers or pharmacologically acceptable acid addition salts thereof, wherein $Z^-$ is chloride, bromide, iodide, hydroxide, hydrogensulfate, sulfate, nitrate, phosphate, formate, acetate, trifluoroacetate, fumarate, citrate, tartrate, oxalate, succinate, mandelate, methanesulfonate or p-toluenesulfonate, or wherein $Z^-$ may be absent if the remaining compound of formula (I) carries at least one negatively charged substituent $R^3$ or $R^4$. If $Z^-$ is selected from anions carrying more than one negative charge, such as fumarate, citrate, tartrate, oxalate, or succinate, $Z^-$ may represent the monovalent equivalent part of such an anion. Alternatively, $Z^-$ may represent the respective partially protonated form, such as hydrogenfumarate, hydrogencitrate, dihydrogencitrate, hydrogentartrate, etc. Further in this context the term "negatively charged substituent $R^3$ or $R^4$ is meant to include substituents which at a neutral pH-value are to a substantial extent present in deprotonated form, i.e. substituents having a pKa value of 9 or lower, such as carboxygroups or acidic hydroxyl substituents.

One particular embodiment of the invention relates to compounds of formula (I) as defined herein or to the tautomers or pharmacologically acceptable acid addition salts thereof, wherein $Z^-$ is chloride, iodide, formate or trifluoroacetate, or $Z^-$ may be absent if the remaining compound of formula (I) carries a negatively charged substituent $R^3$ or $R^4$.

Any substituent defined above may be combined with any other substituent defined above. Particularly preferred are compounds of formula (I) or the pharmaceutically acceptable salts thereof wherein at least 2, 3, 4, 5, or 6 of the substituents defined herein have one of the particular or preferred meaning as defined herein.

Preparation

The following methods are suitable for preparing compounds of general formula (I).

The compounds according to the invention may be obtained using methods of synthesis which are known to the one skilled in the art and described in the literature of organic synthesis. General methods for functional group protection and deprotection are described e.g. in: Greene, T. W. and Wuts, P. G. M. (eds.): Protective Groups in Organic Synthesis, third edition 1999; John Wiley and Sons, Inc. Preferably the compounds are obtained analogously to the methods of preparation explained more fully hereinafter, in particular as described in the experimental section.

Compounds of general formula (I) can be prepared by standard amidation procedures from amines of general formula (II) and the appropriate 3,5-diaminopyrazine-2-carboxylic acid applying e.g. the coupling reagent HATU. Amines (II) can be prepared from N-protected precursors of general formula (III) by standard deprotection procedures. Suitable protecting groups in (III) are e.g. BOC (wherein RPG denotes —NHPG with PG denoting tert-BuOC(O)—) and phthaloyl (wherein RPG denotes phthalimide). Compounds (III) can be prepared by alkylation of benzimidazoles of general formula (IIIa) applying alkylating agents $R^1$-LG. The leaving group LG can be e.g. Br or I.

Alternatively, compounds of general formula (I) can be prepared by alkylation of benzimidazoles of general formula (Ia) applying alkylating agents $R^1$-LG. The leaving group LG can be e.g. Br or I. Compounds of general formula (Ia) can be prepared by standard amidation procedures from amines of general formula (IIa) and the approprioate 3,5-diaminopyrazine-2-carboxylic acid applying e.g. the coupling reagent HATU. Amines (IIa) can be prepared from N-protected precursors of general formula (IIIa) by standard deprotection procedures. Suitable protecting groups in (IIIa) are e.g. BOC (wherein RPG denotes —NHPG with PG denoting tert-BuOC(O)—) and phthaloyl (wherein RPG denotes phthalimide).

Benzimidazoles (IIIa) can be prepared from phenylenediamines (IV) in a two step procedure comprising (i) amidation with N-protected glycine using e.g. the coupling reagent TBTU and (ii) ring closure under acid catalysis, e.g. in glacial acetic acid at elevated temperature.

Phenylenediamines can be prepared from the respective nitroanilines (V) by standard nitro reduction conditions (e.g. catalytic hydrogenation using raney-nickel as a catalyst).

Compounds (V) can be prepared from derivatives (VI) by nucleophilic substitution of the leaving group LG (e.g. F or Cl) with a primary amine $R^2$—$NH_2$ as nucleophile. Alternatively, compounds (V) can be accessed from nitroanilines (Va) by either alkylation (using an alkylating agent $R^2$-LG) or reductive amination (using an appropriate aldehyde) of the aromatic amino group.

Compounds (I), (Ia), (III), (IIIa) and (V) can be modified using methods of synthesis which are known to one skilled in the art and described in the literature of organic synthesis, preferably by functional group protection or deprotection steps, esterifications, amidation, hydrogenations, or 1,3-dipolar cycloadditions. Thereby, before such a modification, the structures of $R^1$, $R^2$, $R^3$, and $R^4$ may be beyond of what is claimed hereinafter.

The skilled person will appreciate that within these general synthesis schemes, the substituents $R^1$ and $R^2$ can in principle be interchanged, meaning that $R^2$ instead of $R^1$ can be introduced in the late alkylation step applying an alkylating agent $R^2$-LG.

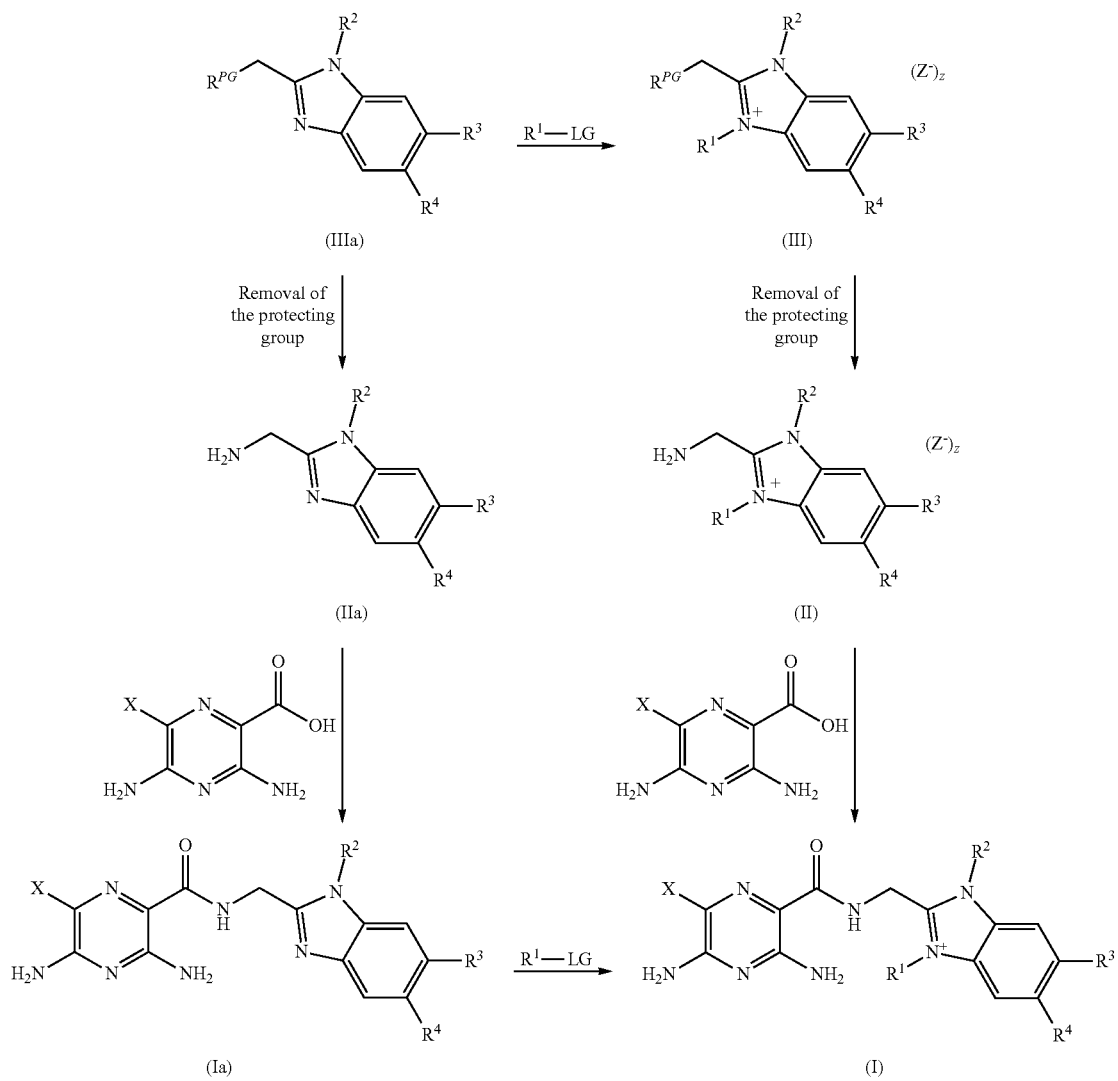

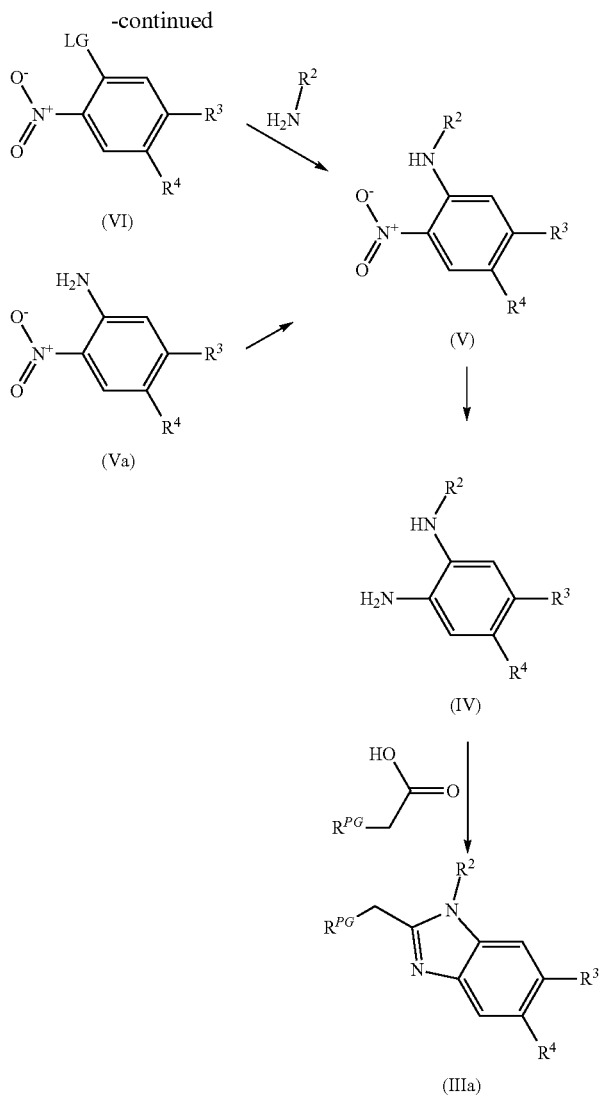

Compounds of formula (I), as defined hereinbefore, are salts containing an anion $Z^-$. These anions $Z^-$ may be derived from synthesis or purification or changed from one anionic species to another suitable anionic species by methods known to those skilled in the art. Examples of such methods are ion exchange using for example ion exchange resins or displacement of an acid counterion from its salt using another, usually stronger, acid. For example, treatment of a compound of formula (I), as defined hereinbefore, where $Z^-$ is $CF_3COO^-$, with HCl in a suitable solvent, such as water, methanol or diethyl ether, may produce a compound of formula 1, as defined hereinbefore, where $Z^-$ is $Cl^-$.

Certain compounds of formula (I), as defined hereinbefore, may contain groups that may be further converted into the salts thereof, for pharmaceutical use particularly into pharmaceutically acceptable salts with inorganic or organic acids and bases. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid. Corresponding processes are known to the skilled person.

Moreover, where one or more stereoisomers may exist, the compounds of general formula (I) or intermediates in the synthesis of compounds of general formula (I) may be obtained as mixtures and then resolved into their stereoisomers, e.g. enantiomers and/or diastereomers. Thus, for example, cis/trans mixtures may be resolved into their cis and trans isomers, and racemic compounds may be separated into their enantiomers.

Thus, for example, the cis/trans mixtures may be resolved by chromatography into the cis and trans isomers thereof. The compounds of general formula (I) or intermediates in the synthesis of compounds of general formula 1, which occur as racemates may be separated by methods known per se (cf. Allinger N. L. and Eliel E. L. in "Topics in Stereochemistry", Vol. 6, Wiley Interscience, 1971) into their optical antipodes and compounds of general formula 1 or intermediates in the synthesis of compounds of general formula (I) with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, ditoloyltartaric acid, malic acid, mandelic acid, camphorsulfonic acid, glutamic acid, aspartic acid, or quinic acid. Optically active alcohols applicable as auxiliary residues may be, for example, (+) or (−)-menthol and optically active acyl groups in amides may be, for example, (+)- or (−)-menthyloxycarbonyl.

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

The compounds according to the invention are advantageously obtainable using the methods described in the examples that follow, which may also be combined for this purpose with methods known to the skilled person from his/her expert knowledge. Likewise, further compounds according to this invention, whose preparation are not explicitly described in the following examples, can be prepared analogously or similarly to the examples.

EXAMPLES

The following examples illustrate the present invention without restricting its scope.

Other features and advantages of the present invention will become apparent from the following more detailed Examples which illustrate, by way of example, the principles of the invention.

Where no salt forms of compounds are specified, the compound may exist as a free base or a salt or a zwitterion, depending on the chemical structure, the synthesis conditions and the processes of workup and purification applied. The skilled person will appreciate that the compound is not limited to a certain salt form. Where salt forms of compounds are specified, the stoichiometry of the counterion is usually omitted. In case of multiply charged counterions the skilled person will appreciate that the resulting salt form is uncharged, leading to the corresponding stoichiometry. The skilled person will appreciate that the compound is not limited to the mono salt form and that it may exist as a disalt, trisalt or other compound: counterion stoichiometries. Furthermore, the skilled person will appreciate that such compound may unexpectedly exist as a salt with a different counterion, depending on the synthesis conditions and the processes of workup and purification applied. Solely for the purpose of yield determination, an estimate of the nature of the counterion and of compound: counterion stoichiometry is made (as indicated by the formula given).

Synthesis of Intermediates

Intermediate A.1

3,5-Diamino-6-Chloropyrazine-2-Carboxylic acid

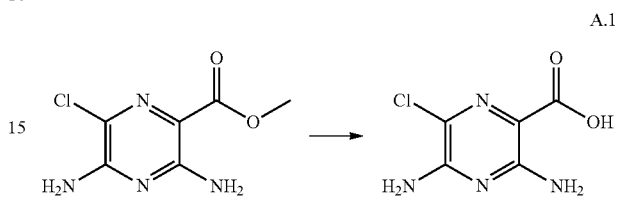

A mixture of methyl 3,5-diamino-6-chloropyrazine-2-carboxylate (100 g; 494 mmol), methanol (1 l) and NaOH (6 mol/l in water; 240 ml; 1.44 mol) is refluxed for 3 h. The mixture is allowed to cool to r.t. and then neutralized by addition of hydrochloric acid (6 mol/l in water; approx. 240 mL). Water (200 ml) is added. The precipitate formed is filtered off with suction, washed with water and dried at 60° C. $C_5H_5ClN_4O_2$ ESI Mass spectrum: m/z=189 [M+H]+; m/z=187 [M−H]−

Intermediate A.2

3,5-Diamino-6-Bromopyrazine-2-Carboxylic Acid

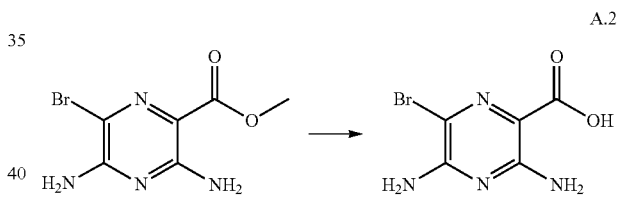

A.2 is prepared from methyl 3,5-diamino-6-bromopyrazine-2-carboxylate (which is prepared from methyl 3,5-diamino-6-chloropyrazine-2-carboxylate as described in J. Med. Chem. 10 (1967) 66-75) analogously to the procedure described for the synthesis of intermediate A.1

Intermediate B.1

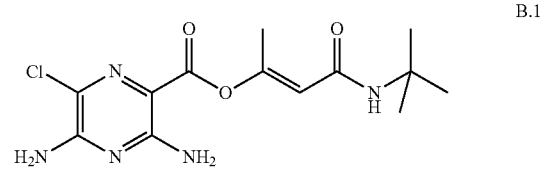 [SMILES: C/C(=C\C(=O)NC(C)(C)C)OC(=O)c1nc(Cl)c(N)nc1N]

Stage 1:
A mixture of tert-butanol (21.0 ml; 226 mmol) and 5-methylisoxazole (18.0 ml; 221 mmol) is cooled with an ice-bath. Trifluoromethanesulphonic acid (20.0 ml; 221 mmol) is added dropwise with continued cooling. The resulting mixture is stirred for 1 h without further cooling.
Stage 2:
To a solution or suspension of intermediate A.1 (14.0 g; 74.2 mmol) and triethylamine (31.0 ml; 222 mmol) in DMF (1400 ml) is added the mixture prepared in stage 1. The resulting mixture is stirred for 4 h at r.t. Ice-water is added with stirring. The precipitate formed is filtered off with suction, washed with water and dried at 65° C. to yield the title compound ($C_{13}H_{18}ClN_5O_3$).

TLC (Silica; DCM/MeOH 9:1): $R_f$=0.4

ESI Mass spectrum: m/z=328 [M+H]$^+$; m/z=326 [M−H]$^−$

Intermediate I.1

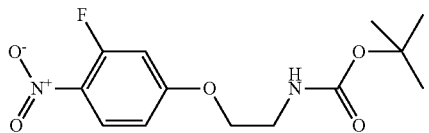

A mixture of 3-fluoro-4-nitro-phenol (25.29 g; 0.16 mol), N-(2-bromoethyl)carbaminic acid (1,1)dimethyl)ethyl ester (36.08 g; 0.16 mol) and potassium carbonate (24.48 g; 0.18 mol) in acetone is refluxed for 8 h. The mixture is evaporated and the residue is purified by silica gel chromatography (eluent: DCM/methanol 100/1).

The following intermediates are prepared accordingly from the respective phenol and the respective alkyl halide as indicated. Depending upon conditions applied, the syntheses may yield a free base, a TFA salt or other salt forms which can be applied equally to the syntheses of example compounds described herein.

| Intermediate No. | Structure | phenol applied | alkyl halide applied | Synthesis comment |
|---|---|---|---|---|
| I.2 | 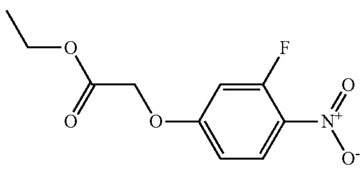 [SMILES: CCOC(=O)COc1ccc([N+](=O)[O-])c(F)c1] | | | Reaction for 3 h at 50° C. |
| I.3 | 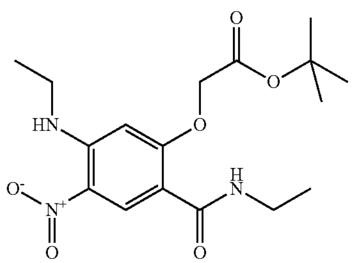 [SMILES: CCNC(=O)c1cc([N+](=O)[O-])c(NCC)cc1OCC(=O)OC(C)(C)C] | XX.2 | | Reaction overnight at r.t. |
| I.4 | 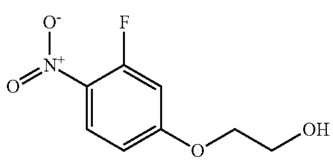 [SMILES: O=[N+]([O-])c1ccc(OCCO)cc1F] | | | |
| I.5 | | | | Reaction in ACN at 80° C. for 2 h |
| I.5 | | XX.4 | | Reaction in DMF at 70° C. for 1 h |

Intermediate II.1

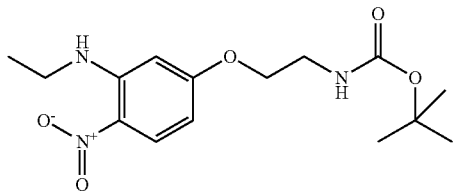

A mixture of Intermediate I.1 (19.1 g; 63.6 mmol), ethylamine (2 M in THF; 47.7 ml; 95.4 mmol) and potassium carbonate (14.0 g; 102 mmol) in THF (300 ml) is stirred at 50° C. for 2 h and at r.t. for 3 days. Insolubles are filtered off and discarded, the mother liquor is evaporated. The residue is taken up in DCM and washed with water. The organic layer is separated, dried and evaporated.

$C_{15}H_{23}N_3O_5$ ESI Mass spectrum: m/z=326 [M+H]+

The following intermediates are prepared accordingly from the respective aryl halide and the respective amine as indicated. Depending upon conditions applied, the syntheses may yield a free base, a TFA salt or other salt forms which can be applied equally to the syntheses of example compounds described below.

| Intermediate No. | Structure | Aryl halide applied | amine applied | Synthesis comment |
|---|---|---|---|---|
| II.2 | 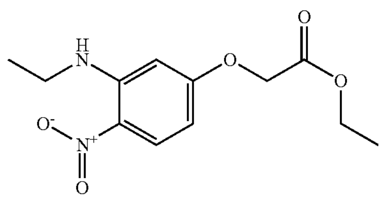 [SMILES: CCNc1cc(OCC(=O)OCC)ccc1[N+](=O)[O-]] | I.2 | Ethylamine | No addition of potassium carbonate |
| II.3 | 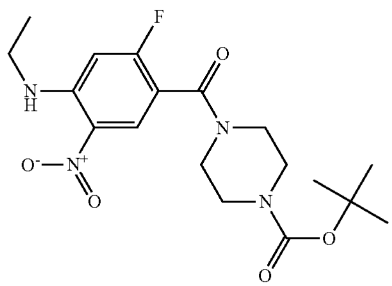 [SMILES: CCNc1cc(F)c(C(=O)N2CCN(C(=O)OC(C)(C)C)CC2)cc1[N+](=O)[O-]] | XIII.1 | Ethylamine | Triethylamine added as base; solvent is Methyl-THF |
| II.4 | 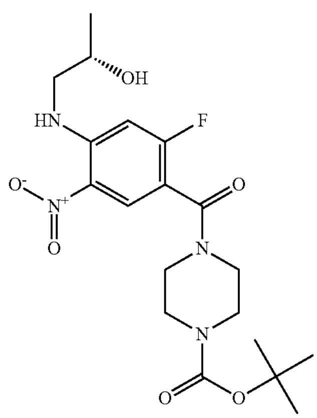 [SMILES: C[C@H](O)CNc1cc(F)c(C(=O)N2CCN(C(=O)OC(C)(C)C)CC2)cc1[N+](=O)[O-]] | XIII.1 | (S)-1-amino-2-propanol | Triethylamine added as base; solvent is Methyl-THF. Purification by silica gel chromatography (DCM/MeOH 0->5%, then DCM/EE 0->100%) |
| II.5 | 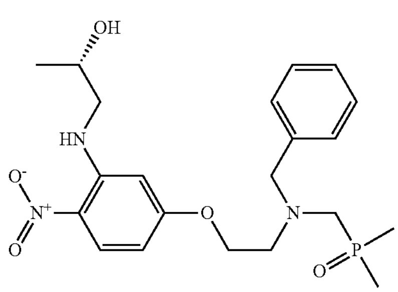 [SMILES: C[C@H](O)CNc1cc(OCCN(Cc2ccccc2)CP(C)(C)=O)ccc1[N+](=O)[O-]] | XVII.1 | (S)-1-amino-2-propanol | 2 eq. of the amine applied, no further base; solvent is Methyl-THF. |

-continued

| Intermediate No. | Structure | Aryl halide applied | amine applied | Synthesis comment |
| --- | --- | --- | --- | --- |
| II.6 | 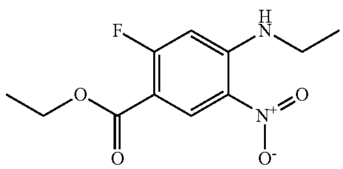 [SMILES: CCNc1cc(F)c(C(=O)OCC)cc1[N+](=O)[O-]] | XI.2 | Ethylamine | 2 eq. of the amine applied, no further base; solvent is THF; reaction at −50° C.- > r.t. |
| II.7 | 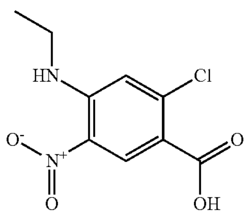 [SMILES: CCNc1cc(Cl)c(C(=O)O)cc1[N+](=O)[O-]] | | Ethylamine | Reaction with 4 eq. ethylamine (70% in water) as reactand and base. Acidified before workup |
| II.8 | 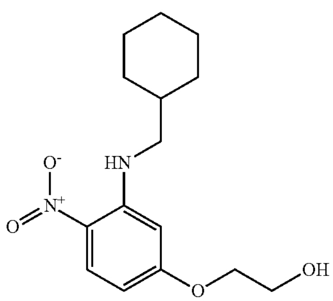 [SMILES: O=[N+]([O-])c1ccc(OCCO)cc1NCC1CCCCC1] | I.4 | | 2 eq. of the amine applied, no further base; solvent is Methyl-THF. Reaction at 60° C. overnight |
| II.9 | 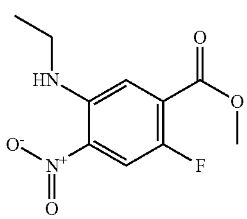 [SMILES: CCNc1cc(C(=O)OC)c(F)cc1[N+](=O)[O-]] | | Ethylamine | No addition of potassium carbonate |
| II.10 | 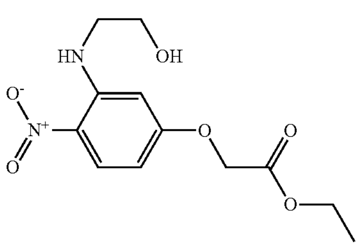 [SMILES: CCOC(=O)COc1ccc([N+](=O)[O-])c(NCCO)c1] | I.2 | Ethanolamine | 2 eq. of the amine applied, no further base; solvent is THF; reaction at −50° C.- > r.t. |
| II.11 | 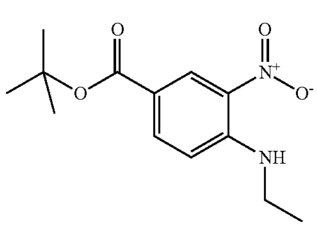 [SMILES: CCNc1ccc(C(=O)OC(C)(C)C)cc1[N+](=O)[O-]] | | Ethylamine | 5 eq. of the amine applied, no further base; solvent is THF-water 6:1. |

-continued

| Intermediate No. | Structure | Aryl halide applied | amine applied | Synthesis comment |
|---|---|---|---|---|
| II.12 | (structure) | (structure) | (S)-1-amino-2-propanol | 2 eq. of the amine applied, no further base; reaction at 70° C. for 2 h; purification by silica gel chromatography (DCM/MeOH 0->12%) |
| II.13 | (structure) | I.5 | n-propyl-amine | 2 eq. of the amine applied, no further base |
| II.14 | (structure) | I.2 | Cyclo-propyl-methyl-amine | Reaction in DMF at 80° C. overnight |
| II.15 | (structure) | XIII.2 | Ethanol-amine | Triethylamine added as base; solvent is DCM. Reaction at 0-10° C. Purification by silica gel chromatography (DCM/MeOH 8%) |
| II.16 | (structure) | XXVIII.1 | Ethyl-amine | Solvent: NMP; purification by silica gel chromatography (petrol ether/EE 30->50%) |

Intermediate III.1

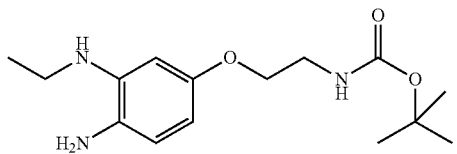

Intermediate II.1 (13.3 g; 40.9 mmol) in methanol (500 ml) is hydrogenated in a Parr apparatus (r.t.; 3 bar hydrogen; catalyst: 1.30 g Pd/C 10%). The catalyst is filtered off and the solvent is evaporated to obtain Intermediate III.1.

The following intermediates are prepared accordingly from the respective aryl halide and the respective amine as indicated. Depending upon conditions applied, the syntheses may yield a free base, a TFA salt or other salt forms which can be applied equally to the syntheses of example compounds described below.

| Intermediate No. | Structure | Nitro compound applied | Synthesis comment |
|---|---|---|---|
| III.2 | 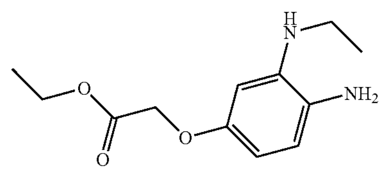 [SMILES: CCNc1cc(OCC(=O)OCC)ccc1N] | II.2 | Catalyst: Pd/C (5%) |
| III.3 | 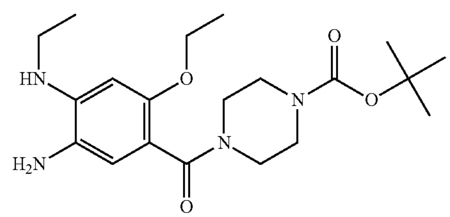 [SMILES: CCNc1cc(OCC)c(C(=O)N2CCN(C(=O)OC(C)(C)C)CC2)cc1N] | XIV.1 | Solvent: THF<br>Catalyst: Raney-Ni |
| III.4 | 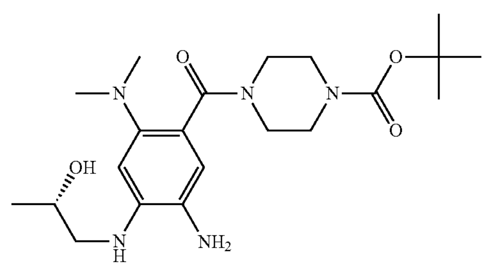 [SMILES: C[C@H](O)CNc1cc(N(C)C)c(C(=O)N2CCN(C(=O)OC(C)(C)C)CC2)cc1N] | XIV.3 | Solvent: THF<br>Catalyst: Raney-Ni |
| III.5 | 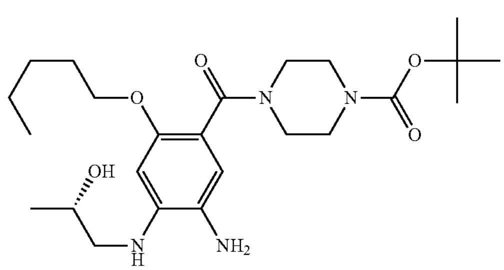 [SMILES: CCCCCOc1cc(NC[C@H](C)O)c(N)cc1C(=O)N1CCN(C(=O)OC(C)(C)C)CC1] | XIV.2 | Solvent: THF<br>Catalyst: Raney-Ni |
| III.6 | 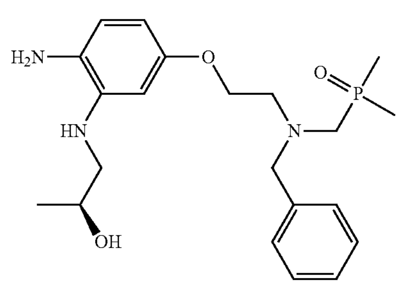 [SMILES: C[C@H](O)CNc1cc(OCCN(Cc2ccccc2)CP(C)(C)=O)ccc1N] | II.5 | Solvent: THF<br>Catalyst: Raney-Ni |

-continued

| Intermediate No. | Structure | Nitro compound applied | Synthesis comment |
|---|---|---|---|
| III.7 | 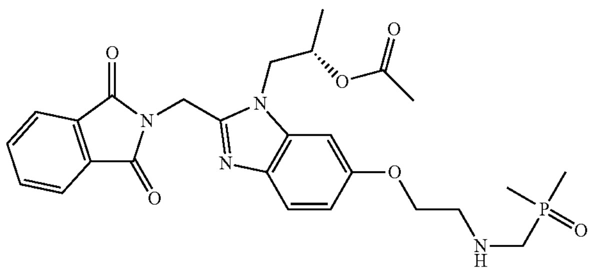 [SMILES: CC(=O)O[C@@H](C)Cn1c(CN2C(=O)c3ccccc3C2=O)nc2ccc(OCCNCP(C)(C)=O)cc21] | IV.5 | Catalyst: Pd/C (5%); purification by silica gel chromatography (DCM/MeOH 0->20%) |
| III.8 | 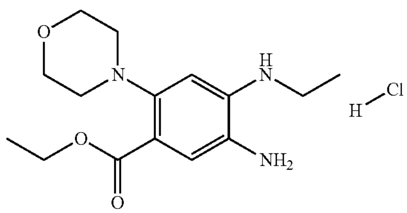 | XIV.4 | Solvent: EtOH/EE/aq. HCl 15:5:1 |
| III.9 | 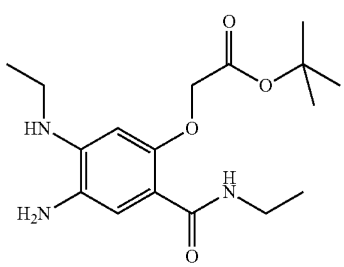 [SMILES: CCNC(=O)c1cc(N)c(NCC)cc1OCC(=O)OC(C)(C)C] | I.3 | |
| III.10 | 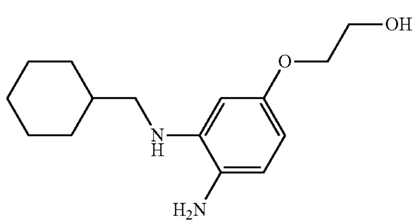 [SMILES: Nc1ccc(OCCO)cc1NCC1CCCCC1] | II.8 | Solvent: THF Catalyst: Raney-Ni |
| III.11 | 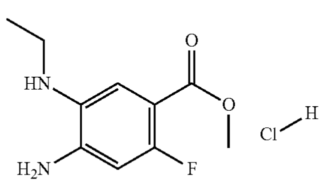 | II.9 | Catalyst: Pd/C (5%); Solvent: MeOH/aq. HCl (2 mol/l) 3:1 |
| III.12 | 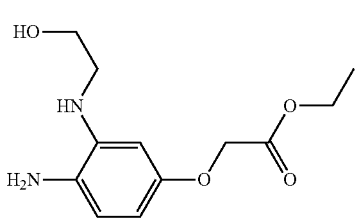 [SMILES: CCOC(=O)COc1ccc(N)c(NCCO)c1] | II.10 | Solvent: THF Catalyst: Raney-Ni |

-continued

| Intermediate No. | Structure | Nitro compound applied | Synthesis comment |
|---|---|---|---|
| III.13 | 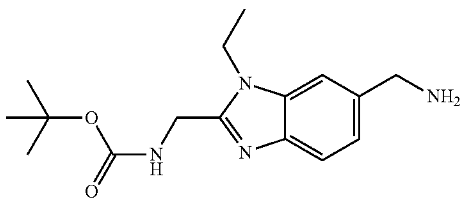 [SMILES: CCn1c(CNC(=O)OC(C)(C)C)nc2ccc(CN)cc21] | IV.13 | Solvent: MeOH/ammonia<br>Catalyst: Raney-Ni |
| III.14 | 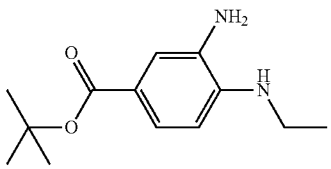 [SMILES: CCNc1ccc(C(=O)OC(C)(C)C)cc1N] | II.11 | |
| III.15 | 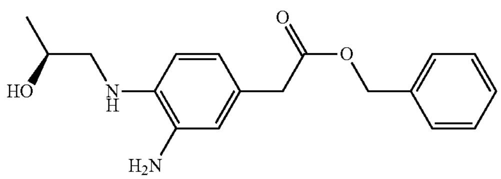 [SMILES: C[C@H](O)CNc1ccc(CC(=O)OCc2ccccc2)cc1N] | II.12 | Solvent: THF<br>Catalyst: Raney-Ni |
| III.16 | 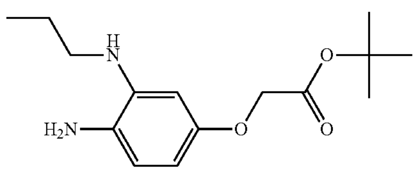 [SMILES: CCCNc1cc(OCC(=O)OC(C)(C)C)ccc1N] | II.13 | Solvent: THF |
| III.17 | 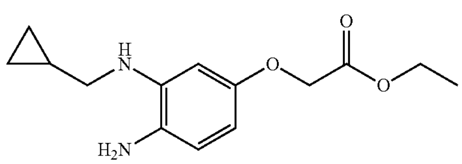 [SMILES: CCOC(=O)COc1ccc(N)c(NCC2CC2)c1] | II.14 | Solvent: MeOH |
| III.18 | 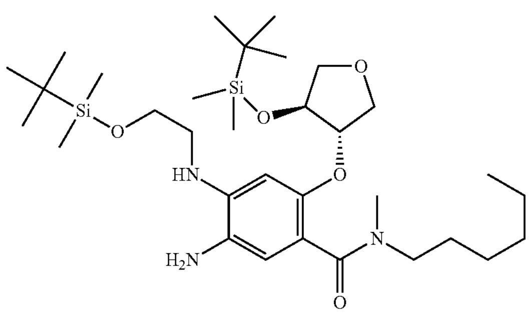 [SMILES: CCCCCCN(C)C(=O)c1cc(N)c(NCCO[Si](C)(C)C(C)(C)C)cc1O[C@H]1COC[C@@H]1O[Si](C)(C)C(C)(C)C] | XIV.4 | Solvent: THF<br>Catalyst: Raney-Ni |
| III.19 | 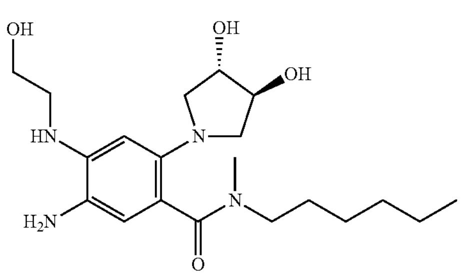 [SMILES: CCCCCCN(C)C(=O)c1cc(N)c(NCCO)cc1N1C[C@H](O)[C@@H](O)C1] | XIV-5 | Solvent: THF<br>Catalyst: Raney-Ni |

| Intermediate No. | Structure | Nitro compound applied | Synthesis comment |
|---|---|---|---|
| III.20 | 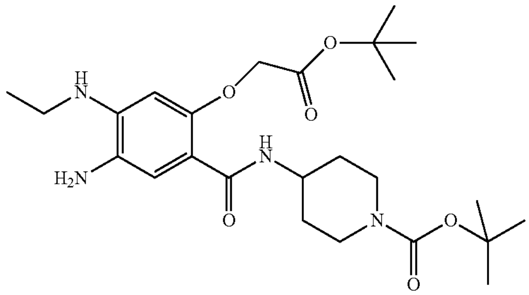 [SMILES: CCNc1cc(OCC(=O)OC(C)(C)C)c(C(=O)NC2CCN(C(=O)OC(C)(C)C)CC2)cc1N] | I.5 | |

Intermediate IV.1

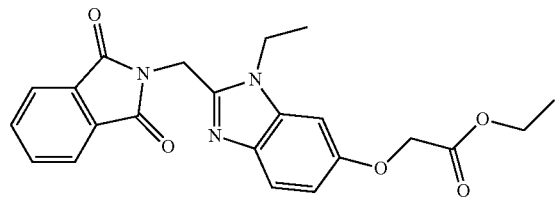

IV.1

A mixture of the diamino intermediate 111.2 (46.2 g; 194 mmol), THF (500 ml), N-phthaloyl glycine (39.8 g; 194 mmol), TBTU (62.2 g; 194 mmol) and triethylamine (21.9 g; 194 mmol) is stirred at RT for 30 min. The mixture is poured on ice-water and stirred until the ice is melted. The precipitate is filtered off with suction, washed with water and dried at 60° C. The so formed intermediate is taken up in acetic acid (200 ml) and dioxane (700 ml) and stirred at 100° C. for 1 h. The mixture is evaporated, taken up in DCM and extracted successively with $Na_2CO_3$ solution and water. The organic layer is separated, evaporated, and the residue is recrystallized from ACN.

$C_{22}H_{21}N_3O_5$ ESI Mass spectrum: m/z=408 [M+H]+

HPLC analytics: RT=0.82 min (HPLC method I)

The following intermediates are prepared accordingly from the respective diamino compound as indicated. Depending upon conditions applied, the syntheses may yield a free base, a TFA salt or other salt forms which can be applied equally to the syntheses of example compounds described below.

| Intermediate No. | Structure | diamino compound applied | Synthesis comment |
|---|---|---|---|
| IV.2 | 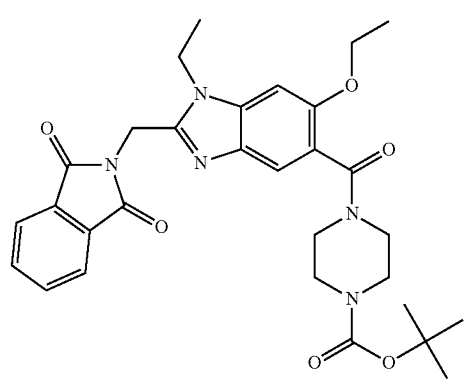 [SMILES: CCOc1cc2c(cc1C(=O)N1CCN(C(=O)OC(C)(C)C)CC1)nc(CN1C(=O)c3ccccc3C1=O)n2CC] | III.3 | Recrystallization from tert-Butylmethyl ether |

| Intermediate No. | Structure | diamino compound applied | Synthesis comment |
|---|---|---|---|
| IV.3 | 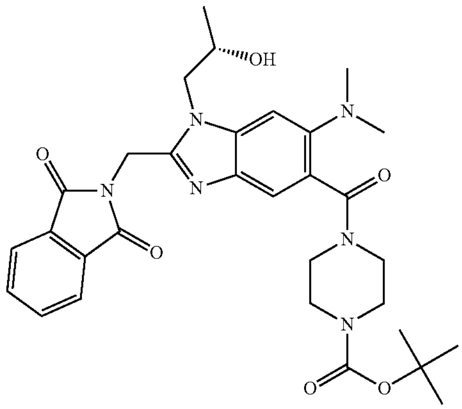 [SMILES: C[C@H](O)Cn1c(CN2C(=O)c3ccccc3C2=O)nc2cc(C(=O)N3CCN(C(=O)OC(C)(C)C)CC3)c(N(C)C)cc21] | III.4 | Stage 2: reaction in acetic acid at 90° C. overnight. No recrystallization |
| IV.4 | 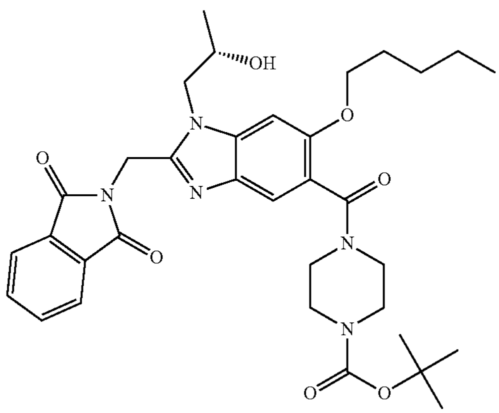 [SMILES: CCCCCOc1cc2c(cc1C(=O)N1CCN(C(=O)OC(C)(C)C)CC1)nc(CN1C(=O)c3ccccc3C1=O)n2C[C@H](C)O] | III.5 | Stage 2: reaction in acetic acid at 90° C. overnight. No recrystallization |
| IV.5 | 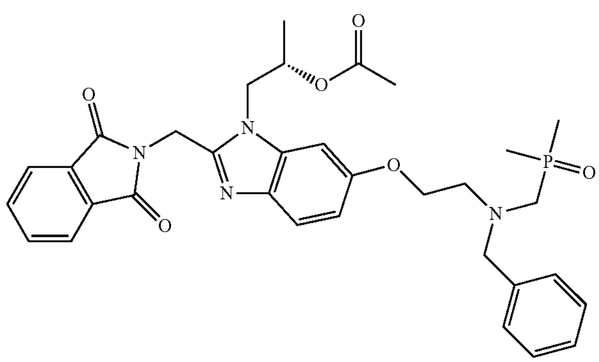 [SMILES: CC(=O)O[C@@H](C)Cn1c(CN2C(=O)c3ccccc3C2=O)nc2ccc(OCCN(Cc3ccccc3)CP(C)(C)=O)cc21] | III.6 | Stage 2: reaction at 90° C. overnight. No recrystallization |
| IV.6 | 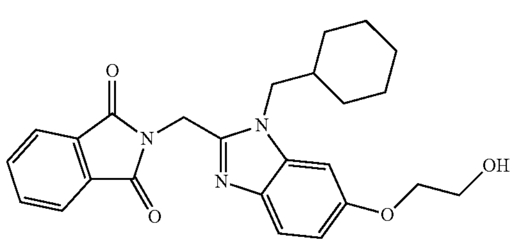 [SMILES: O=C1c2ccccc2C(=O)N1Cc1nc2ccc(OCCO)cc2n1CC1CCCCC1] | III.10 | Stage 2: reaction at 90° C. overnight in HCl (1 mol/l in dioxane). No recrystallization |

-continued

| Intermediate No. | Structure | diamino compound applied | Synthesis comment |
|---|---|---|---|
| IV.7 | 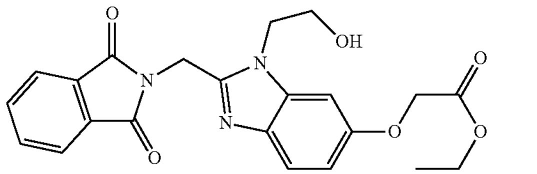 [SMILES: CCOC(=O)COc1ccc2nc(CN3C(=O)c4ccccc4C3=O)n(CCO)c2c1] | III.12 | Stage 2: reaction 85° C. overnight. No recrystallization |
| IV.8 | 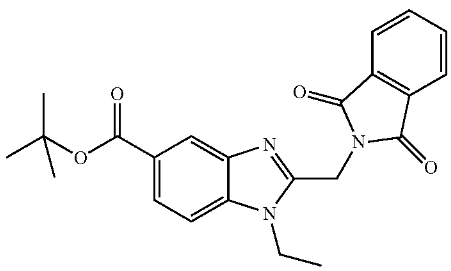 [SMILES: CCn1c(CN2C(=O)c3ccccc3C2=O)nc2cc(C(=O)OC(C)(C)C)ccc21] | III.14 | Stage 1: solvent is ACN/DMF 1:1 |
| IV.9 | 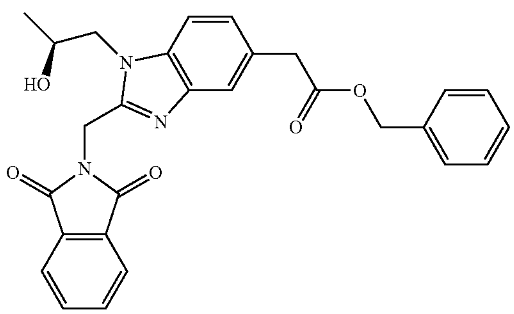 [SMILES: C[C@H](O)Cn1c(CN2C(=O)c3ccccc3C2=O)nc2cc(CC(=O)OCc3ccccc3)ccc21] | III.15 | Stage 2: reaction at 85° C. overnight. No recrystallization |
| IV.10 | 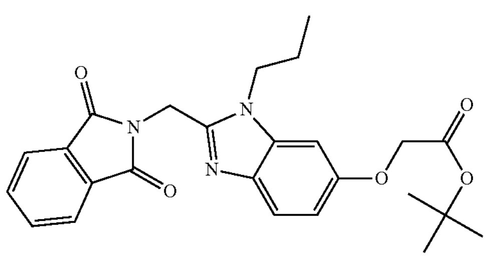 [SMILES: CCCn1c(CN2C(=O)c3ccccc3C2=O)nc2ccc(OCC(=O)OC(C)(C)C)cc21] | III.16 | Stage 2: reaction in dioxane/acetic acid (95:5) at 80° C. for 3 days. No recrystallization |
| IV.11 | 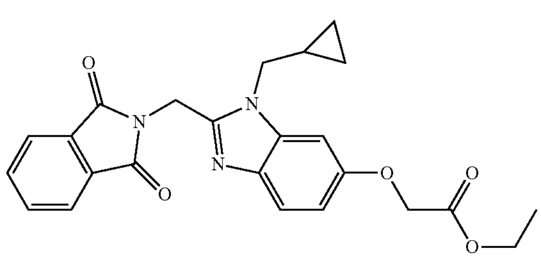 [SMILES: CCOC(=O)COc1ccc2nc(CN3C(=O)c4ccccc4C3=O)n(CC3CC3)c2c1] | III.17 | Purification by silica gel chromatography (DCM/MeOH 0->6%) |
| IV.12 | 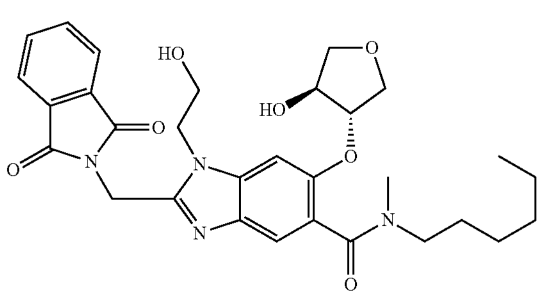 [SMILES: CCCCCCN(C)C(=O)c1cc2nc(CN3C(=O)c4ccccc4C3=O)n(CCO)c2cc1O[C@H]1COC[C@@H]1O] | III.18 | Stage 2: reaction at 80° C. for 3 h in HCl (4 mol/l in dioxane). No recrystallization |

| Intermediate No. | Structure | diamino compound applied | Synthesis comment |
|---|---|---|---|
| IV.13 | (structure) | III.19 | Stage 2: reaction in acetic acid at 80° C. for 3 h. No recrystallization |

Intermediate V.1

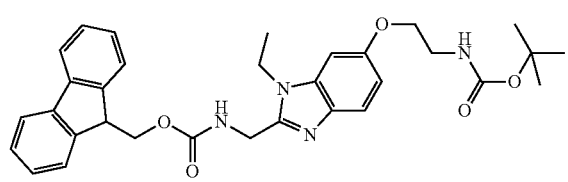

V.1

Step 1: A mixture of Intermediate III.1 (12.00 g; 40.63 mmol), the glycine derivative (9H-fluoren-9-ylmethoxycarbonylamino)-acetic acid (12.08 g; 40.63 mmol), the coupling reagent HATU (16.99 g; 44.69 mmol) and DIPEA (13.91 mL; 81.25 mmol) in DMF (50 ml) is stirred at r.t. for 1 h. The mixture is evaporated.

Step 2: The residue is taken up in glacial acetic acid (50 mL) and stirred at 60° C. for 3 h. The solvent is evaporated. The residue is taken up in DCM and washed with water and NaHCO$_3$ (sat. aq. solution). The organic layer is separated, dried and evaporated. The residue is purified by silica gel chromatography (eluent: DCM/methanol 40/1).

$C_{32}H_{36}N_4O_5$ ESI Mass spectrum: m/z=557 [M+H]+

HPLC analytics: RT=0.63 min (HPLC G)

The following intermediates are prepared accordingly from the respective diamino compound as indicated. Depending upon conditions applied, the syntheses may yield a free base, a TFA salt or other salt forms which can be applied equally to the syntheses of example compounds described below.

| Intermediate No. | Structure | diamino compound applied | Sythesis comment |
|---|---|---|---|
| V.2 | (structure) | III.8 | N-BOC-glycin applied; Step 2: reaction at 80° C. for 6 h |
| V.3 | (structure) | III.9 | Step 2: reaction at 60° C. for 3 days |

-continued

| Intermediate No. | Structure | diamino compound applied | Synthesis comment |
|---|---|---|---|
| V.4 | 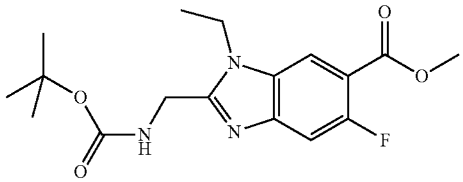 [SMILES: CCn1c(CNC(=O)OC(C)(C)C)nc2cc(F)c(C(=O)OC)cc21] | III.11 | N-BOC-glycin applied; Step 2: reaction at 60° C. overnight |
| V.5 | 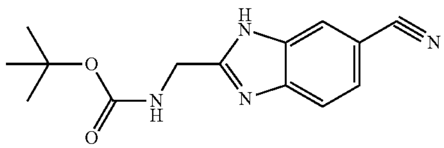 [SMILES: CC(C)(C)OC(=O)NCc1nc2ccc(C#N)cc2[nH]1] | | N-BOC-glycin applied; Step 2: reaction at 50° C. overnight |
| V.6 | 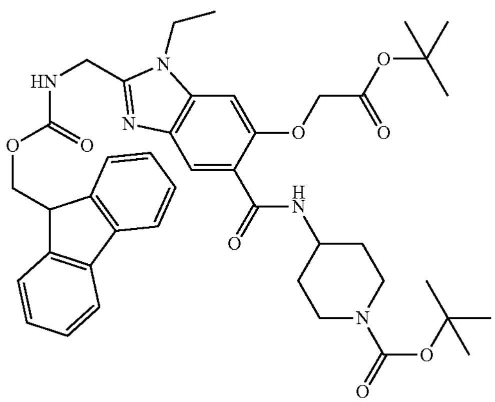 [SMILES: CCn1c(CNC(=O)OCC2c3ccccc3-c3ccccc32)nc2cc(C(=O)NC3CCN(C(=O)OC(C)(C)C)CC3)c(OCC(=O)OC(C)(C)C)cc21] | III.20 | |

Intermediate VI.1

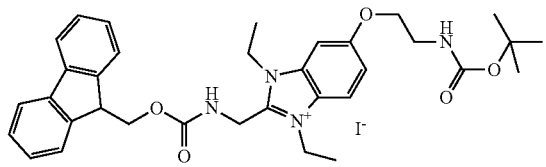

VI.1

A mixture of intermediate V.1 (9.60 g; 17.3 mmol) and ethyl iodide (20.7 ml; 259 mmol) in THF (90 ml) is stirred at 120° C. for 2 h (microwave heating). The mixture is evaporated and the residue is purified by silica gel chromatography (eluent: DCM/methanol 30/1). The residue is stirred in diethyl ether, filtered off and dried.

$C_{34}H_{41}N_4O_5 \times I$ ESI Mass spectrum: m/z=585 [M+]

The following intermediates are prepared accordingly from the respective benzimidazole as indicated. Depending upon conditions applied, the syntheses may yield a free base, a TFA salt or other salt forms which can be applied equally to the syntheses of example compounds described below.

| Intermediate No. | Structure | Benzimidazole applied | Synthesis comment |
|---|---|---|---|
| VI.2 | 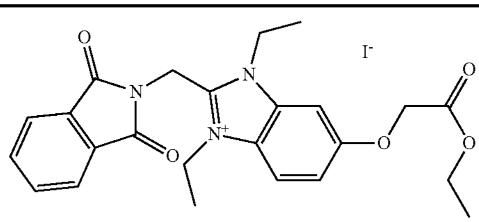 | IV.1 | Solvent: ACN |

-continued

| Intermediate No. | Structure | Benzimidazole applied | Synthesis comment |
|---|---|---|---|
| VI.3 | 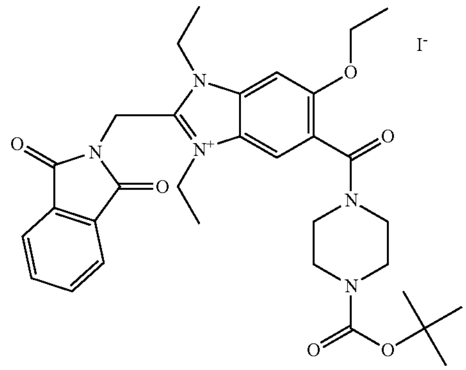 [SMILES: CCOc1cc2c(cc1C(=O)N1CCN(C(=O)OC(C)(C)C)CC1)[n+](CC)c(CN1C(=O)c3ccccc3C1=O)n2CC ; [I-]] | IV.2 | Solvent: ACN<br>Reaction at 90° C. for 3 h |
| VI.4 | 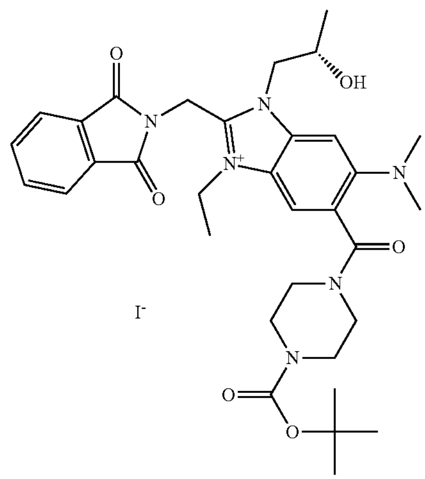 [SMILES: CC[n+]1c(CN2C(=O)c3ccccc3C2=O)n(C[C@H](C)O)c2cc(N(C)C)c(C(=O)N3CCN(C(=O)OC(C)(C)C)CC3)cc21 ; [I-]] | IV.3 | Solvent: ACN;<br>3 eq. of Iodoethane applied |
| VI.5 | 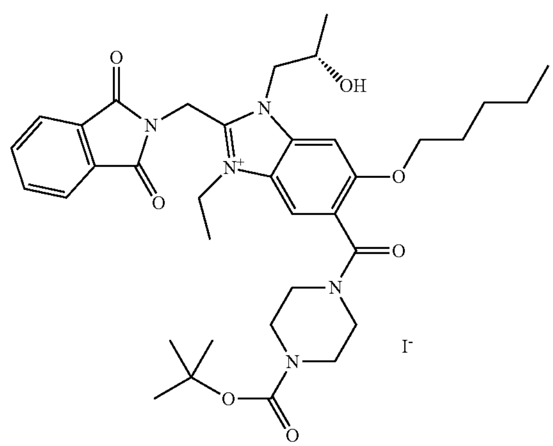 [SMILES: CCCCCOc1cc2c(cc1C(=O)N1CCN(C(=O)OC(C)(C)C)CC1)[n+](CC)c(CN1C(=O)c3ccccc3C1=O)n2C[C@H](C)O ; [I-]] | IV.4 | Solvent: ACN;<br>3 eq. of Iodoethane applied |

-continued

| Intermediate No. | Structure | Benzimidazole applied | Synthesis comment |
|---|---|---|---|
| VI.6 | 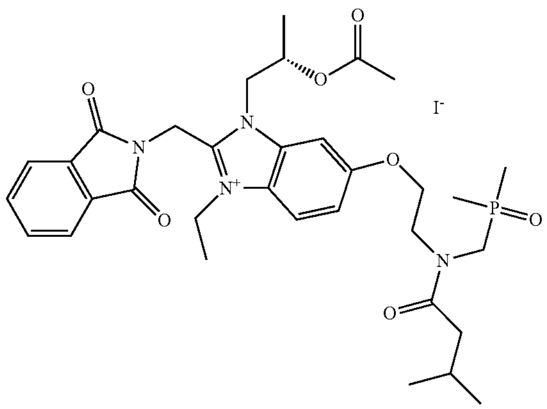 [SMILES: CC[n+]1c(CN2C(=O)c3ccccc3C2=O)n(C[C@H](C)OC(C)=O)c2cc(OCCN(CP(C)(C)=O)C(=O)CC(C)C)ccc21 ; [I-]] | XVIII.1 | Solvent: ACN; 3 eq. of Iodoethane applied |
| VI.7 | 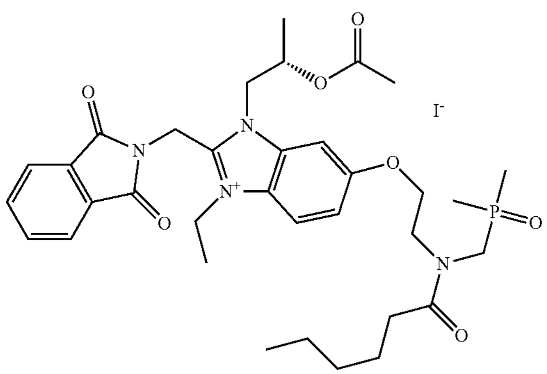 [SMILES: CCCCCC(=O)N(CCOc1ccc2c(c1)n(C[C@H](C)OC(C)=O)c(CN1C(=O)c3ccccc3C1=O)[n+]2CC)CP(C)(C)=O ; [I-]] | XVIII.2 | Solvent: ACN; 3 eq. of Iodoethane applied |
| VI.8 | 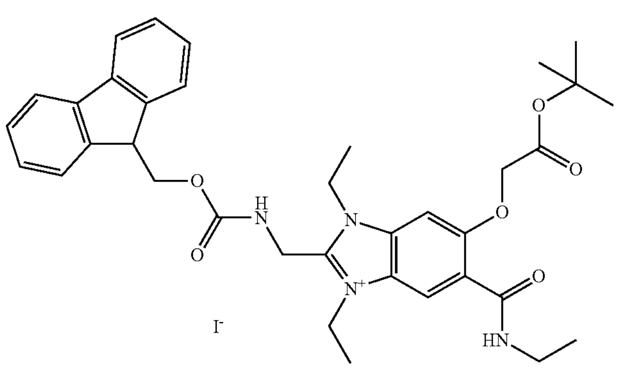 [SMILES: CCNC(=O)c1cc2c(cc1OCC(=O)OC(C)(C)C)n(CC)c(CNC(=O)OCC1c3ccccc3-c3ccccc31)[n+]2CC ; [I-]] | V.3 | Solvent: ACN Reaction at 100° C. for 6 h |
| VI.9 | 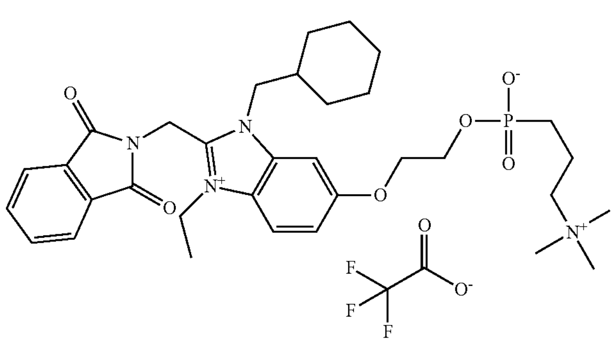 [SMILES: CC[n+]1c(CN2C(=O)c3ccccc3C2=O)n(CC2CCCCC2)c2cc(OCCOP(=O)([O-])CCC[N+](C)(C)C)ccc21 ; O=C([O-])C(F)(F)F] | XXIII.1 | Solvent: ACN; 3 eq. of Iodoethane applied, 2 eq. of Hünig's base added. Reaction overnight at 120° C. Purification by RP-HPLC (modifier: TFA) |

-continued

| Intermediate No. | Structure | Benzimidazole applied | Synthesis comment |
|---|---|---|---|
| VI.10 | 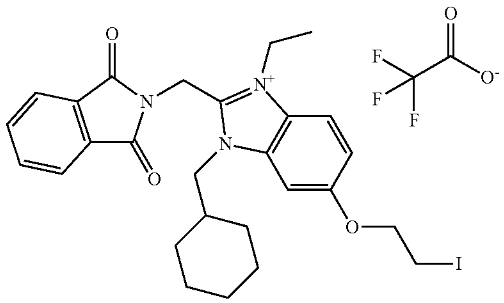 [SMILES: CC[n+]1c(CN2C(=O)c3ccccc3C2=O)n(CC2CCCCC2)c2cc(OCCI)ccc21 ; O=C([O-])C(F)(F)F] | XXIII.1 | byproduct generated in the reaction to VI.9 |
| VI.11 | 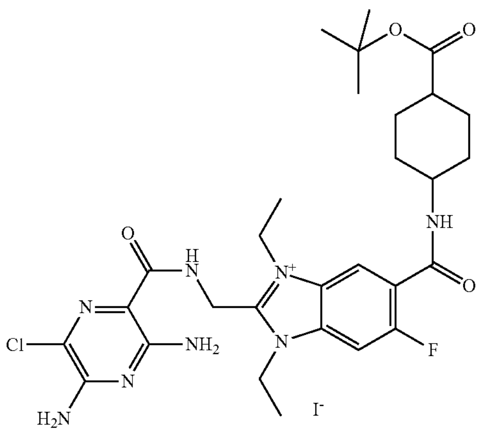 [SMILES: CCn1c(CNC(=O)c2nc(Cl)c(N)nc2N)[n+](CC)c2cc(C(=O)NC3CCC(C(=O)OC(C)(C)C)CC3)c(F)cc21 ; [I-]] | VIII.5 | |
| VI.12 | 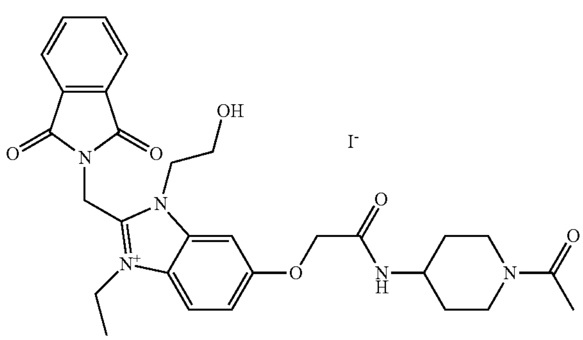 [SMILES: CC[n+]1c(CN2C(=O)c3ccccc3C2=O)n(CCO)c2cc(OCC(=O)NC3CCN(C(C)=O)CC3)ccc21 ; [I-]] | XXI.3 | Solvent: ACN; 5 eq. of Iodoethane applied |
| VI.13 | 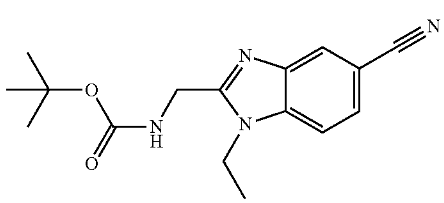 [SMILES: CCn1c(CNC(=O)OC(C)(C)C)nc2cc(C#N)ccc21] | V.5 | 1.1 eq. Iodoethane and 1.1 eq. LiHMDS applied; reaction at 50° C. overnight |

-continued

| Intermediate No. | Structure | Benzimidazole applied | Synthesis comment |
|---|---|---|---|
| VI.14 | 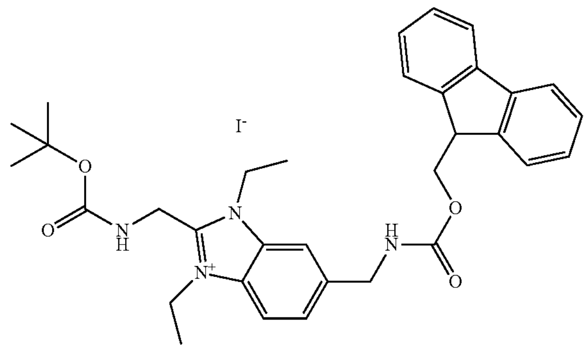 [SMILES: CCn1c(CNC(=O)OC(C)(C)C)[n+](CC)c2ccc(CNC(=O)OCC3c4ccccc4-c4ccccc43)cc21 ; [I-]] | XXV.1 | |
| VI.15 | 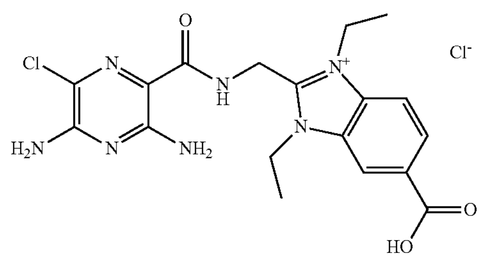 [SMILES: CCn1c(CNC(=O)c2nc(Cl)c(N)nc2N)[n+](CC)c2ccc(C(=O)O)cc21 ; [Cl-]] | VIII.7 | Solvent: ACN; purification by RP-HPLC (modifier: TFA). Product taken up in aq. HCl and evaporated to dryness |
| VI.16 | 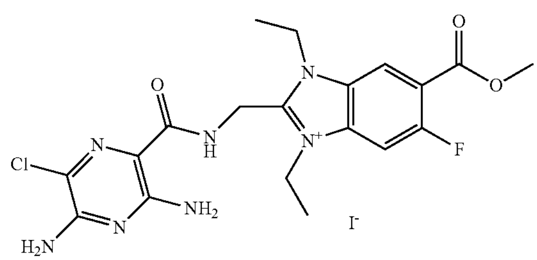 [SMILES: CCn1c(CNC(=O)c2nc(Cl)c(N)nc2N)[n+](CC)c2cc(F)c(C(=O)OC)cc21 ; [I-]] | XXIV.1 | Reaction in ACN at 100° C. for 3 h. |
| VI.17 | 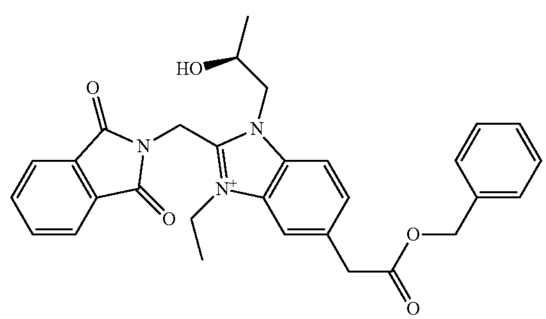 [SMILES: CC[n+]1c(CN2C(=O)c3ccccc3C2=O)n(C[C@H](C)O)c2ccc(CC(=O)OCc3ccccc3)cc21] | IV.9 | Solvent: ACN |
| VI.18 | 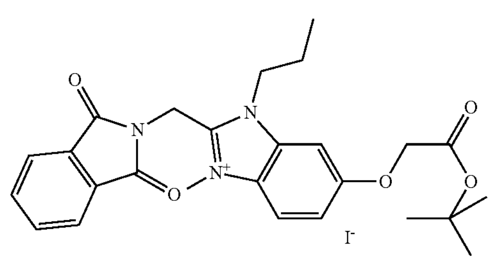 [SMILES: CCCn1c(CN2C(=O)c3ccccc3C2=O)[n+](C)c2ccc(OCC(=O)OC(C)(C)C)cc21 ; [I-]] | IV.10 | Alkylating agent: iodo-methane (3. eq.). Reaction in ACN at 100° C. for 2 h. |

-continued

| Intermediate No. | Structure | Benzimidazole applied | Synthesis comment |
|---|---|---|---|
| VI.19 | 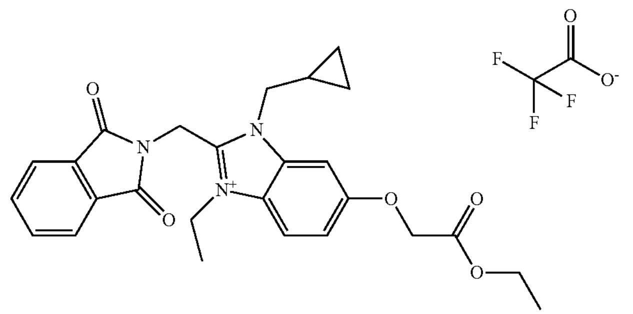 [SMILES: CCOC(=O)COc1ccc2c(c1)n(CC1CC1)c(CN1C(=O)c3ccccc3C1=O)[n+]2CC ; O=C([O-])C(F)(F)F] | IV.11 | Solvent: ACN |
| VI.20 | 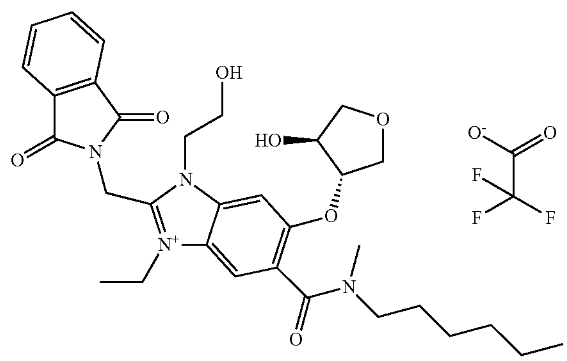 [SMILES: CCCCCCN(C)C(=O)c1cc2c(cc1O[C@H]1COC[C@@H]1O)n(CCO)c(CN1C(=O)c3ccccc3C1=O)[n+]2CC ; O=C([O-])C(F)(F)F] | IV.12 | Solvent: ACN; 3 eq. of Iodoethane applied |
| VI.21 | 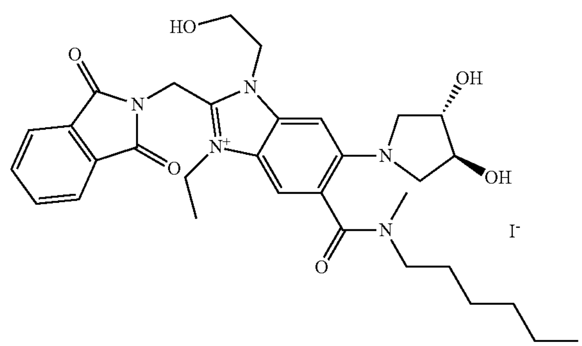 [SMILES: CCCCCCN(C)C(=O)c1cc2c(cc1N1C[C@H](O)[C@@H](O)C1)n(CCO)c(CN1C(=O)c3ccccc3C1=O)[n+]2CC ; [I-]] | IV.13 | Solvent: ACN Reaction at 90° C. for 3 h |
| VI.22 | 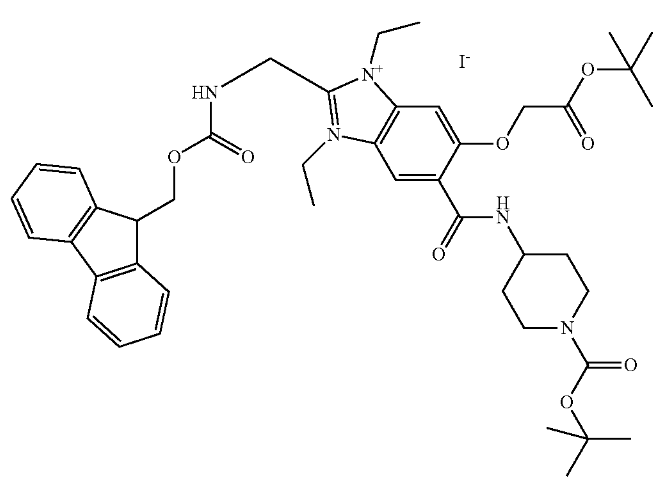 | V.6 | Solvent: ACN Reaction at 90° C. for 12 h |

-continued

| Intermediate No. | Structure | Benzimidazole applied | Synthesis comment |
|---|---|---|---|
| VI.23 | 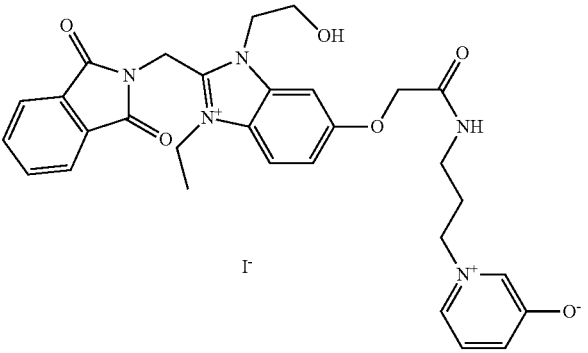 [SMILES: CC[n+]1c(CN2C(=O)c3ccccc3C2=O)n(CCO)c2cc(OCC(=O)NCCC[n+]3cccc([O-])c3)ccc21 ; [I-]] | VIII.10 | Solvent: ACN |

Intermediate VII.1

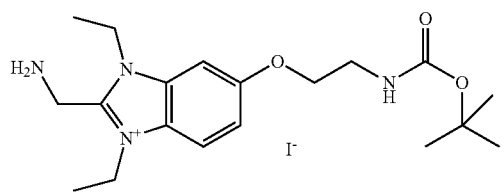

A mixture of intermediate VI.1 (8.20 g; 11.51 mmol) and piperidine (11.4 ml; 115 mmol) in THF (90 ml) is stirred at r.t. for 2 days. The precipitate is filtered off, washed with diethyl ether and dried.

$C_{19}H_{31}N_4O_3 \times I$ ESI Mass spectrum: m/z=363 [M+]

The following compounds are prepared accordingly applying the respective amine as indicated. Depending upon conditions applied, the procedures may yield a chloride salt, a TFA salt or bis-TFA salt, a zwitterion or other salt forms.

| Example | Structure | Amine applied | Synthesis comment |
|---|---|---|---|
| VII.2 | 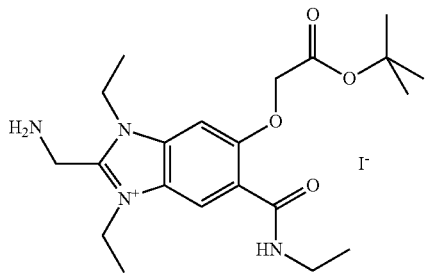 [SMILES: CCNC(=O)c1cc2c(cc1OCC(=O)OC(C)(C)C)n(CC)c(CN)[n+]2CC ; [I-]] | VI.8 | Purification by silica gel chromatography (DCM/MeOH 4:1) |
| VII.3 | 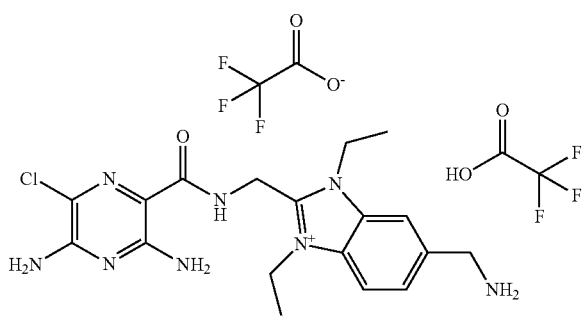 [SMILES: CCn1c(CNC(=O)c2nc(Cl)c(N)nc2N)[n+](CC)c2ccc(CN)cc21 ; O=C([O-])C(F)(F)F ; O=C(O)C(F)(F)F] | VIII.6 | Purification by RP-HPLC (modifier: TFA) |

| Example | Structure | Amine applied | Synthesis comment |
|---|---|---|---|
| VII.4 | 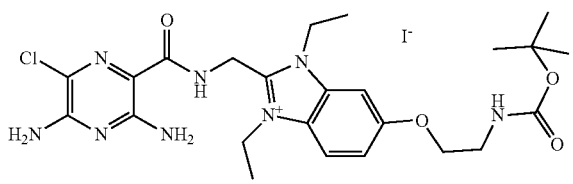 | VI.22 | Purification by silica gel chromatography (DCM/MeOH 4:1) |

Intermediate VIII.1

VIII.1

A mixture of 3,5-diamino-6-chloro-pyrazine-2-carboxylic acid (Intermediate A. 1; 1.04 g; 5.51 mmol), the amine intermediate VII.1 (2.70 g; 5.51 mmol) the coupling reagent HATU (2.25 g; 5.92 mmol) and Hünig's base (1.89 ml; 11.0 mmol) in DMF (30 ml) is stirred at r.t. over night. The mixture is evaporated, taken up in DCM, extracted with water. The organic layer is separated, dried ($Na_2SO_4$) and evaporated again. The crude product is taken to the next step without further purification.

$C_{24}H_{34}ClN_8O_4 \times I$ ESI Mass spectrum: m/z=533 $[M+H]^+$

HPLC analytics: RT=0.85 min (HPLC method B)

The following compounds are prepared accordingly applying the respective acid and amine as indicated. Depending upon conditions applied, the procedures may yield a chloride salt, a TFA salt or bis-TFA salt, a zwitterion or other salt forms.

| Intermediate No. | Structure | Acid applied | Amine applied | Synthesis comment |
|---|---|---|---|---|
| VIII.2 | 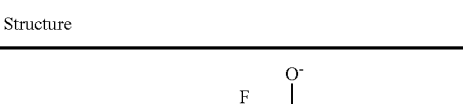 | A.1 | XI.1 | Coupling reagent: TBTU Base: triethylamine See footnote a) |
| VIII.3 | 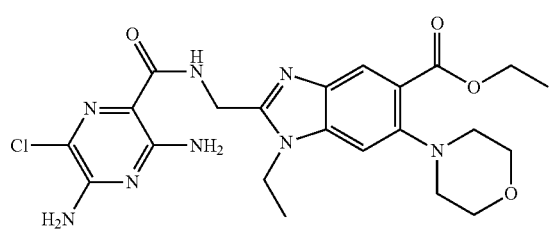 [SMILES: CCOC(=O)c1cc2nc(CNC(=O)c3nc(Cl)c(N)nc3N)n(CC)c2cc1N1CCOCC1] | A.1 | XIX.1 | Coupling reagent: TBTU |

-continued

| Intermediate No. | Structure | Acid applied | Amine applied | Synthesis comment |
|---|---|---|---|---|
| VIII.4 | 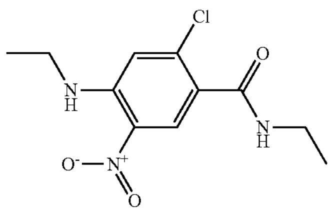 [SMILES: CCNC(=O)c1cc([N+](=O)[O-])c(NCC)cc1Cl] | II.7 | Ethylamine | |
| VIII.5 | 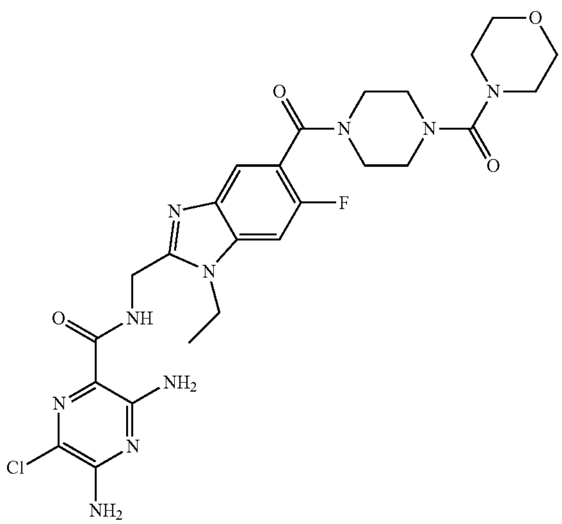 [SMILES: CCn1c(CNC(=O)c2nc(Cl)c(N)nc2N)nc2cc(C(=O)N3CCN(C(=O)N4CCOCC4)CC3)c(F)cc21] | XX.3 | | Coupling reagent: TBTU. Re-crystallization from acetone/ diethyl ether |
| VIII.6 | 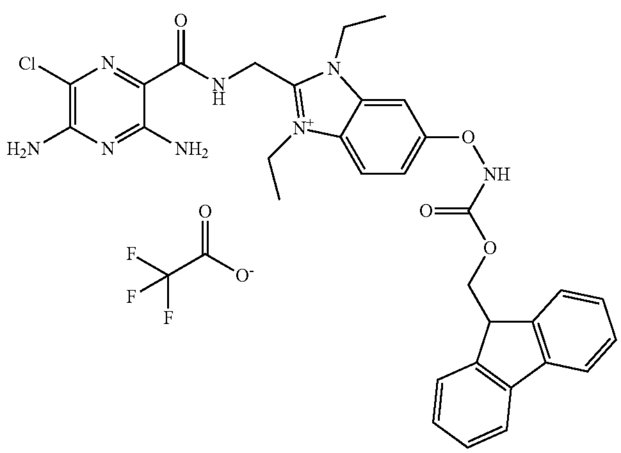 [SMILES: CCn1c(CNC(=O)c2nc(Cl)c(N)nc2N)[n+](CC)c2ccc(ONC(=O)OCC3c4ccccc4-c4ccccc43)cc21 ; O=C([O-])C(F)(F)F] | | XIX.3 | Purification by silica gel chromatography (DCM/MeOH 0->5%) |
| VIII.7 | 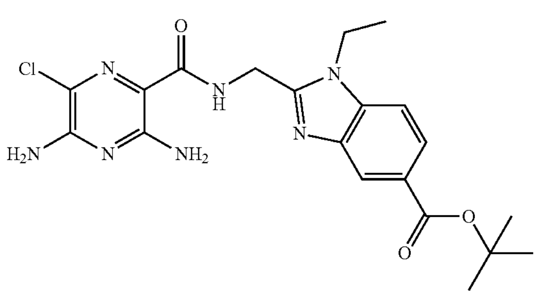 [SMILES: CCn1c(CNC(=O)c2nc(Cl)c(N)nc2N)nc2cc(C(=O)OC(C)(C)C)ccc21] | A.1 | XV.9 | |

| Intermediate No. | Structure | Acid applied | Amine applied | Synthesis comment |
|---|---|---|---|---|
| VIII.8 | 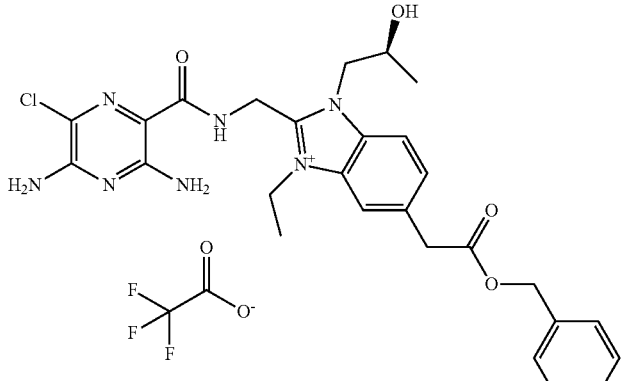 | A1 | XV.10 | Coupling reagent: TBTU<br>Base: triethylamine<br>See footnote a |
| VIII.9 | 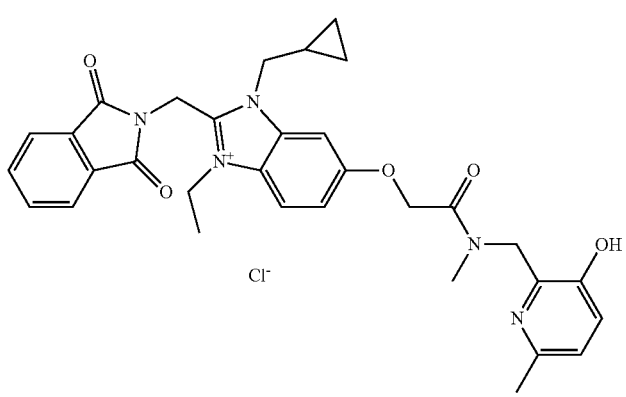 [SMILES: CC[n+]1c(CN2C(=O)c3ccccc3C2=O)n(CC2CC2)c2cc(OCC(=O)N(C)Cc3nc(C)ccc3O)ccc21 ; [Cl-]] | XII.6 | XXIX.1 | Purification by silica gel chromatography (DCM/MeOH 2->8%) |
| VIII.10 | 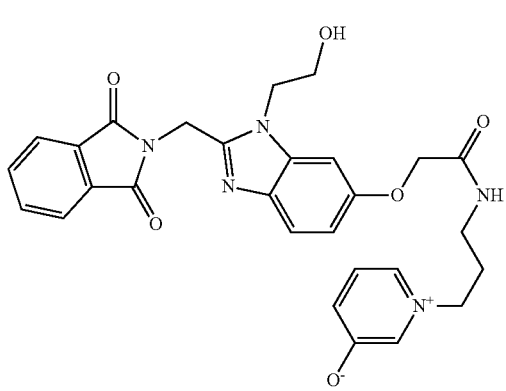 [SMILES: O=C(COc1ccc2nc(CN3C(=O)c4ccccc4C3=O)n(CCO)c2c1)NCCC[n+]1cccc([O-])c1] | XII.2 | XXX.1 | Reaction at 50° C. | a) Purification by RP-HPLC (modifier: TFA).

Intermediate IX.1

IX.1

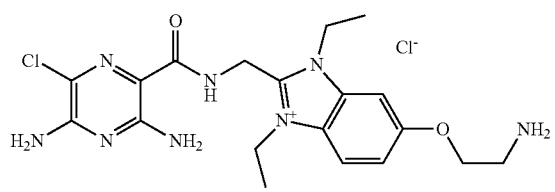

A mixture of Intermediate VIII.1 (1.20 g; 1.82 mmol) and TFA (20% in DCM; 20 ml) is stirred at r.t. for 1 h. The mixture is purified by RP-HPLC (column: SunFire C18; water-ACN; modifier TFA). The product is taken up in HCl/MeOH and the solvent is evaporated to yield the title compound.

$C_{19}H_{26}ClN_8O_2 \times Cl$ ESI Mass spectrum: m/z=433 [M]$^+$

HPLC analytics: RT=0.51 min (HPLC method B)

Intermediate X.1

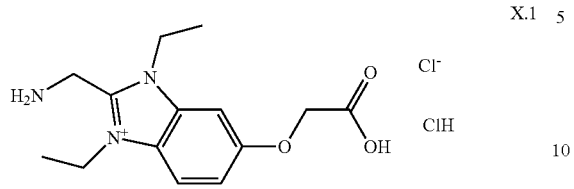

To a solution of intermediate VI.2 (21.3 g; 37.8 mmol) in ACN (250 ml) and ethanol (250 ml) is added hydrazine hydrate (9.18 ml; 189 mmol) in 3 portions over 18 h while the mixture is stirred at 65° C. Insolubles are filtered off and the filtrate is evaporated. The residue is stirred in hydrochloric acid (4 mol/l; 100 ml) at 80° C. for 2 h. The mixture is allowed to cool to r.t., insolubles are filtered off, the filtrate is freeze-dried.

$C_{14}H_{20}N_3O_3 \times Cl \times HCl$ ESI Mass spectrum: m/z=278 [M]$^+$

Intermediate XI.1

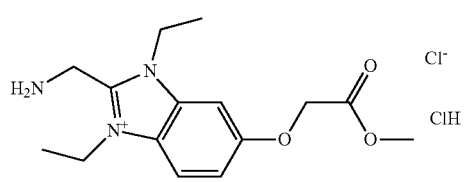

A mixture of intermediate X.1 (14.3 g; 40.8 mmol) and hydrochloric acid (1.3 mol/l in MeOH; 50 ml; 62.5 mmol) is refluxed for 30 min, filtered hot and evaporated to dryness.

$C_{15}H_{22}N_3O_3 \times Cl \times HCl$ ESI Mass spectrum: m/z=292 [M]$^+$

The following compounds are prepared accordingly applying the respective carboxylic acid as indicated. Depending upon conditions applied, the procedures may yield a chloride salt, a TFA salt or bis-TFA salt, a zwitterion or other salt forms.

Intermediate XII.1

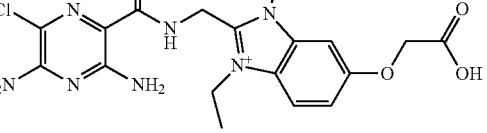

A mixture of the ester intermediate VIII.2 (540 mg; 0.938 mmol) is stirred in hydrochloric acid (1 mol/l; 10.0 ml; 10.0 mmol) at 50° C. until HPLC analytics indicate complete consumption of the starting material. The mixture is freeze dried.

$C_{19}H_{22}ClN_7O_4 \times HCl$ ESI Mass spectrum: m/z=448 [M]$^+$

HPLC analytics: RT=0.36 min (HPLC method G)

The following compounds are prepared accordingly applying the respective ester as indicated. Depending upon conditions applied, the procedures may yield a chloride salt, a TFA salt or bis-TFA salt, a zwitterion or other salt forms.

| Intermediate No. | Structure | Carboxylic acid applied | Synthesis comment |
|---|---|---|---|
| XI.2 | 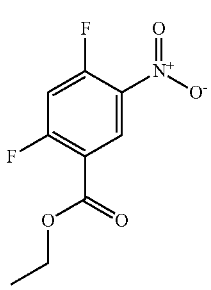 [SMILES: CCOC(=O)c1cc([N+](=O)[O-])c(F)cc1F] |  | Reaction in EtOH/ sulfuric acid 75:1 (vol/vol) |

| Intermediate No. | Structure | ester applied | Synthesis comment |
|---|---|---|---|
| XII.2 | 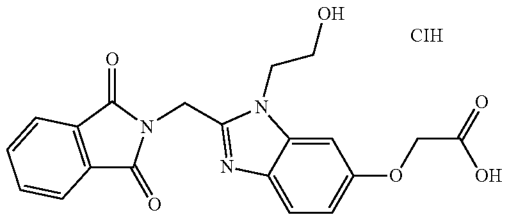 [SMILES: O=C(O)COc1ccc2nc(CN3C(=O)c4ccccc4C3=O)n(CCO)c2c1 ; "CIH"] | IV.7 | Reaction in aq. HCl (4 mol/l) at 65° C. overnight. Product precipitates upon cooling to r.t.. |
| XII.3 | 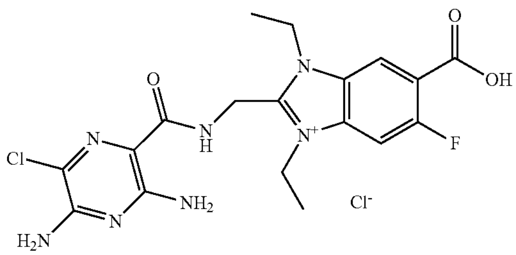 [SMILES: CCn1c(CNC(=O)c2nc(Cl)c(N)nc2N)[n+](CC)c2cc(F)c(C(=O)O)cc21 ; [Cl-]] | VI.16 | Reaction in aq. HCl (4 mol/l) at 75° C. for 3 h |
| XII.4 | 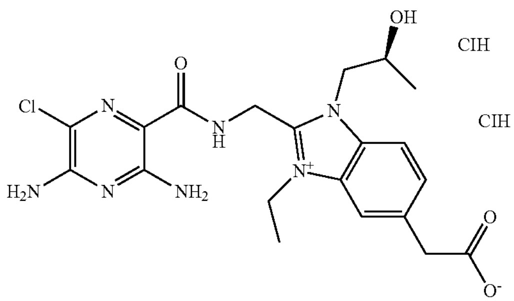 | VIII.8 | |
| XII.5 | 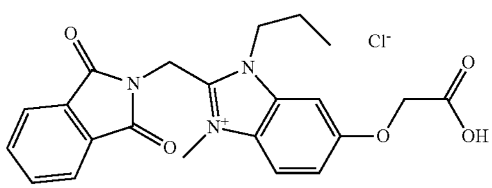 [SMILES: CCCn1c(CN2C(=O)c3ccccc3C2=O)[n+](C)c2ccc(OCC(=O)O)cc21 ; [Cl-]] | VI.18 | Reaction in dioxane/aq. HCl (4 mol/l) |
| XII.6 | 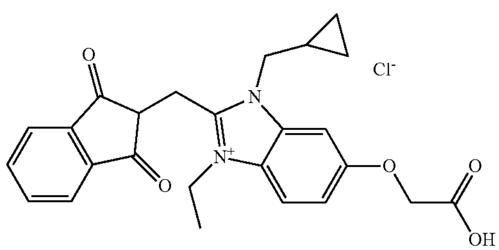 [SMILES: CC[n+]1c(CC2C(=O)c3ccccc3C2=O)n(CC2CC2)c2cc(OCC(=O)O)ccc21 ; [Cl-]] | VI.19 | |

Intermediate XIII.1

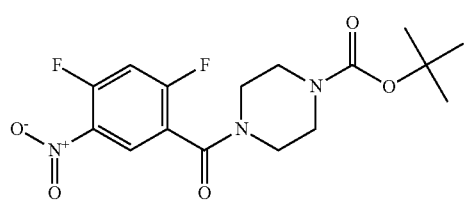

XIII.1

To 2,4-difluoro-5-nitrobenzoic acid (20.0 g; 98.4 mmol) in DCM (150 ml) and DMF (40 ml) is added dropwise a solution of oxalyl chloride (9.17 ml; 108 mmol) in DCM (10 ml). The mixture is stirred for 2 h and evaporated to dryness. The residue is taken up in DCM (150 ml) and triethylamine (30.2 ml; 217 mmol). The amine N-BOC-piperazine (18.3 g; 98.5 mmol) is added in portions while cooling with an ice-bath. The mixture is stirred for further 15 min and extracted with water. The organic layer is dried (MgSO$_4$), filtered and evaporated to dryness.

$C_{16}H_{19}F_2N_3O_5$ ESI Mass spectrum: m/z=272 [M+H−BOC]$^+$

The following compounds are prepared accordingly applying the respective amine as indicated. Depending upon conditions applied, the procedures may yield a chloride salt, a TFA salt or bis-TFA salt, a zwitterion or other salt forms.

| Intermediate No. | Structure | amine applied | Synthesis comment |
|---|---|---|---|
| XIII.2 | 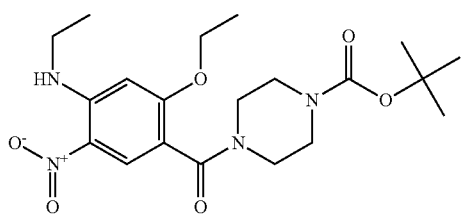 | | |

Intermediate XIV.1

To a mixture of the aryl halide intermediate 11.3 (11.4 g; 28.6 mmol) and THF (150 ml) is added sodium ethoxide (2.34 g; 34.4 mmol). The mixture is stirred overnight at r.t., then Na$_2$CO$_3$ solution and EE is added. The organic layer is separated, dried (MgSO$_4$) and evaporated. The crude product is purified by silica gel chromatography (DCM/MeOH 0->6%; then CH/EE 0->50%).

XIV.1

C$_{20}$H$_{30}$N$_4$O$_6$ ESI Mass spectrum: m/z=423 [M+H]$^+$

The following compounds are prepared accordingly applying the respective reactant(s) as indicated. Depending upon conditions applied, the procedures may yield a chloride salt, a TFA salt or bis-TFA salt, a zwitterion or other salt forms.

| Intermediate No. | Structure | Aryl halide applied | Reactand(s) applied | Synthesis comment |
|---|---|---|---|---|
| XIV.2 | 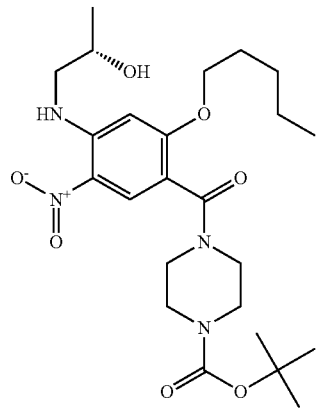 [SMILES: CCCCCOc1cc(NC[C@H](C)O)c([N+](=O)[O-])cc1C(=O)N1CCN(C(=O)OC(C)(C)C)CC1] | II.4 | 1-pentanol (3.2 eq.) and potassium tert-butylate (1.1 eq.) | Solvent: DMF Reaction yields XIV.2 and XIV.3 |
| XIV.3 | 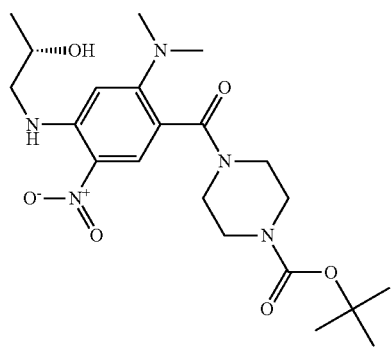 [SMILES: C[C@H](O)CNc1cc(N(C)C)c(C(=O)N2CCN(C(=O)OC(C)(C)C)CC2)cc1[N+](=O)[O-]] | II.4 | 1-pentanol (3.2 eq.) and potassium tert-butylate (1.1 eq.) | Solvent: DMF Reaction yields XIV.2 and XIV.3 |

-continued

| Intermediate No. | Structure | Aryl halide applied | Reactand(s) applied | Synthesis comment |
|---|---|---|---|---|
| XIV.4 | | II.6 | Morpholine (2 eq.) | Reaction in dioxane at 70° C. for 5 h. |
| XIV.4 | | XXVII.1 | | A solution of the alcohol and NaH is added to a solution of the aryl halide |
| XIV.5 | 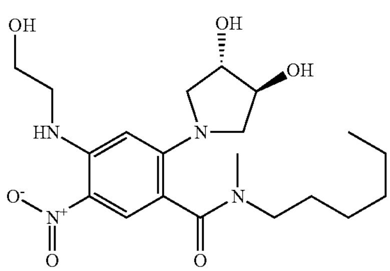 [SMILES: CCCCCCN(C)C(=O)c1cc([N+](=O)[O-])c(NCCO)cc1N1C[C@H](O)[C@@H](O)C1] | II.15 | | Reaction in dioxane at 100° C. for 5 h. |

Intermediate XV.1

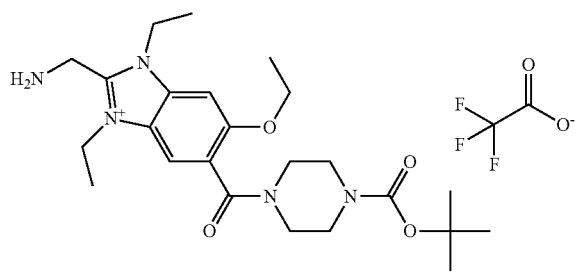

XV.1

A mixture of the phthalimide intermediate VI.3 (6.34 g; 8.84 mmol), hydrazine hydrate (2.15 ml; 44.2 mmol) and ACN (20 ml) is stirred at 60° C. overnight. The mixture is cooled to r.t., insolubles are filtered off with suction, the filtrate is evaporated. The residue is purified by RP-HPLC (modifier: TFA).

$C_{24}H_{38}N_5O_4 \times$TFA ESI Mass spectrum: m/z=460 [M]$^+$

The following compounds are prepared accordingly applying the respective phthalimide as indicated. Depending upon conditions applied, the procedures may yield a chloride salt, a TFA salt or bis-TFA salt, a zwitterion or other salt forms.

| Intermediate No. | Structure | phthalimide applied | Synthesis comment |
|---|---|---|---|
| XV.2 | 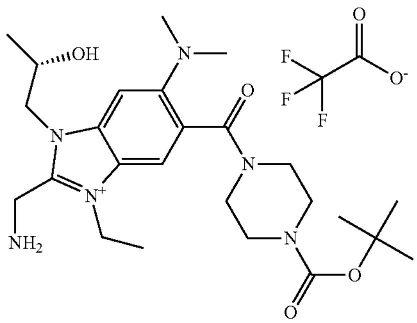 [SMILES: CC[n+]1c(CN)n(C[C@H](C)O)c2cc(N(C)C)c(C(=O)N3CCN(C(=O)OC(C)(C)C)CC3)cc21 ; O=C([O-])C(F)(F)F] | VI.4 | |
| XV.3 | 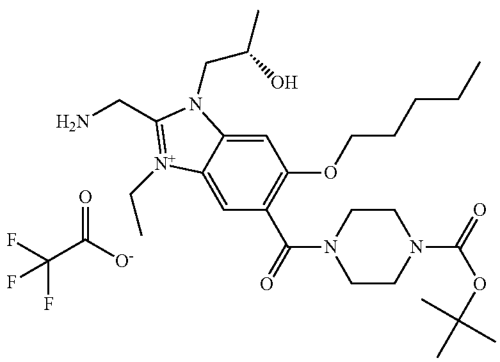 [SMILES: O=C([O-])C(F)(F)F ; CCCCCOc1cc2c(cc1C(=O)N1CCN(C(=O)OC(C)(C)C)CC1)[n+](CC)c(CN)n2C[C@H](C)O] | VI.5 | |
| XV.4 | 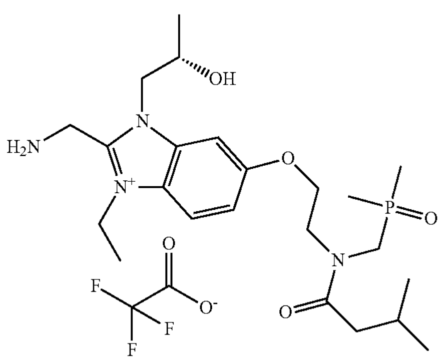 [SMILES: CC[n+]1c(CN)n(C[C@H](C)O)c2cc(OCCN(CP(C)(C)=O)C(=O)CC(C)C)ccc21 ; O=C([O-])C(F)(F)F] | VI.6 | Solvent: MeOH |
| XV.5 | 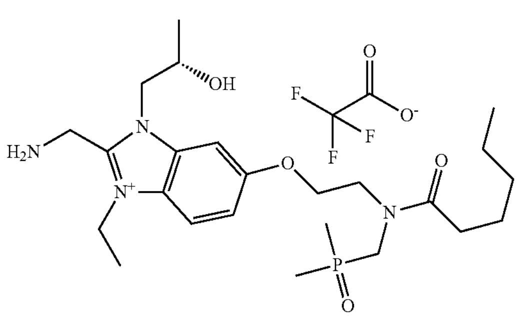 [SMILES: CCCCCC(=O)N(CCOc1ccc2c(c1)n(C[C@H](C)O)c(CN)[n+]2CC)CP(C)(C)=O ; O=C([O-])C(F)(F)F] | VI.7 | Solvent: MeOH |

-continued
| Intermediate No. | Structure | phthalimide applied | Synthesis comment |
|---|---|---|---|
| XV.6 | 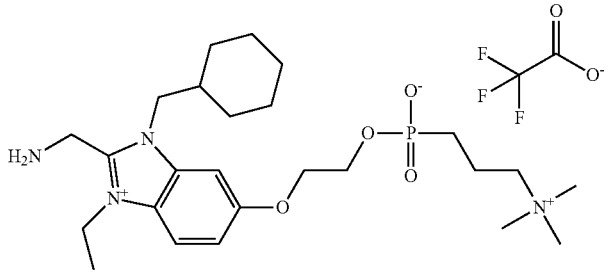 [SMILES: CC[n+]1c(CN)n(CC2CCCCC2)c2cc(OCCOP(=O)([O-])CCC[N+](C)(C)C)ccc21 ; O=C([O-])C(F)(F)F] | VI.9 | Solvent: MeOH |
| XV.7 | 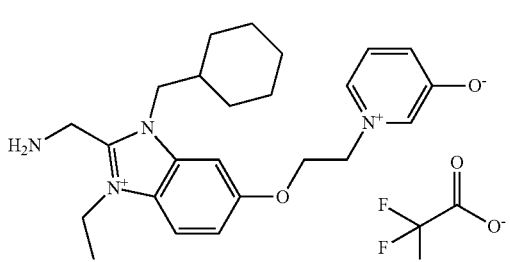 | VI.10 | Prior to the reaction with hydrazine hydrate, 3-hydroxypyridine (4 eq.) is added and the mixture is stirred at 70° C. overnight. |
| XV.8 | 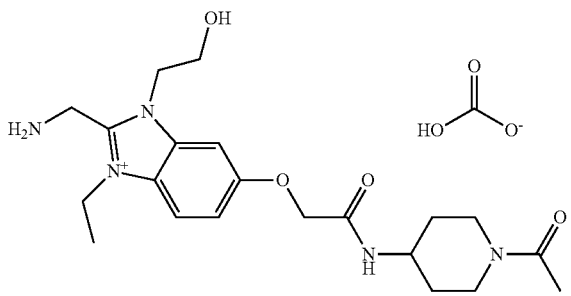 | VI.12 | Solvent: MeOH; exchange of counterion by elution through ion exchange cartridge |
| XV.9 | 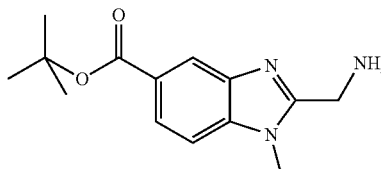 | IV.8 | Solvent: MeOH |
| XV.10 | 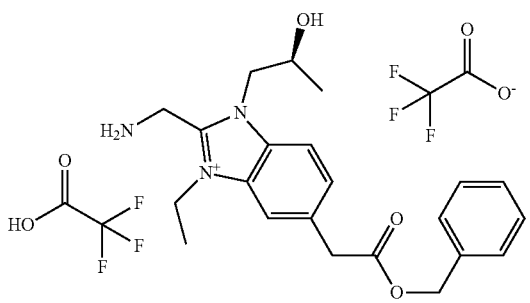 [SMILES: O=C(O)C(F)(F)F ; CC[n+]1c(CN)n(C[C@H](C)O)c2ccc(CC(=O)OCc3ccccc3)cc21 ; O=C([O-])C(F)(F)F] | VI.17 | |

-continued

| Intermediate No. | Structure | phthalimide applied | Synthesis comment |
|---|---|---|---|
| XV.11 | 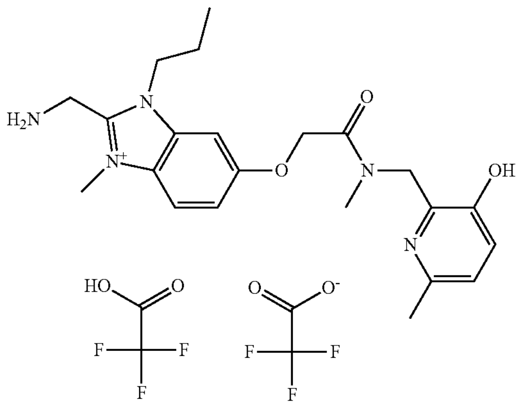 [SMILES: CCCn1c(CN)[n+](C)c2ccc(OCC(=O)N(C)Cc3nc(C)ccc3O)cc21 ; O=C(O)C(F)(F)F ; O=C([O-])C(F)(F)F] | XXVI.1 | Reaction in EtOH at 70° C. overnight |
| XV.12 | 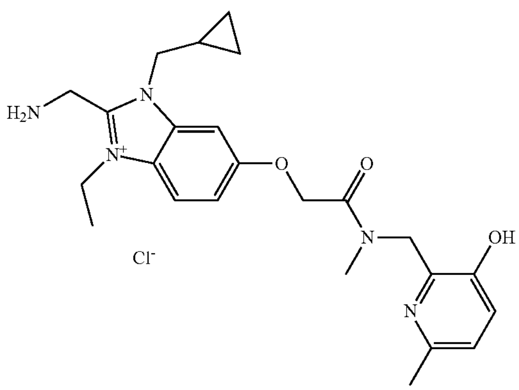 [SMILES: CC[n+]1c(CN)n(CC2CC2)c2cc(OCC(=O)N(C)Cc3nc(C)ccc3O)ccc21 ; [Cl-]] | VIII.9 | Reaction in EtOH, reflux for 1 h |
| XV.13 | 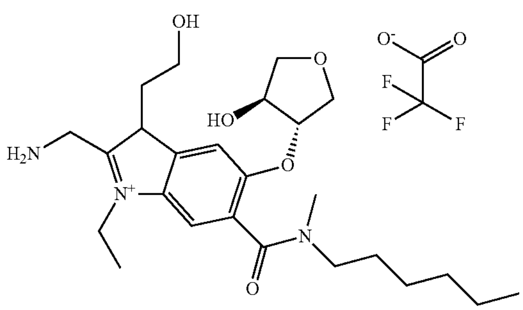 [SMILES: CCCCCCN(C)C(=O)c1cc2c(cc1O[C@H]1COC[C@@H]1O)C(CCO)C(CN)=[N+]2CC ; O=C([O-])C(F)(F)F] | VI.20 | Reaction in EtOH at 50° C. for 2 h |
| XV.14 | 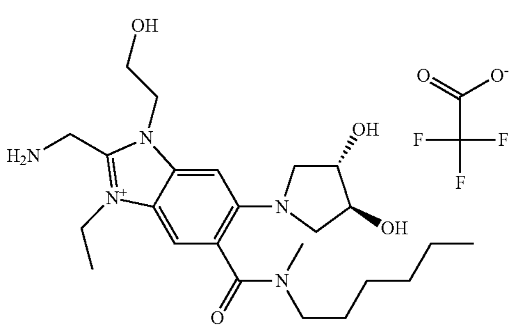 [SMILES: CCCCCCN(C)C(=O)c1cc2c(cc1N1C[C@H](O)[C@@H](O)C1)n(CCO)c(CN)[n+]2CC ; O=C([O-])C(F)(F)F] | VI.21 | Reaction in EtOH, reflux for 2 h |

-continued

| Intermediate No. | Structure | phthalimide applied | Synthesis comment |
|---|---|---|---|
| XV.15 | 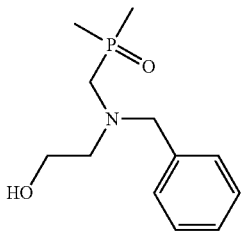 | VI.23 | Solvent: MeOH |

Intermediate XVI.1

XVI.1

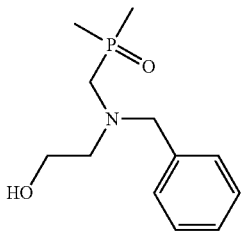

A mixture of N-benzylethanolamine (13.6 g; 90.0 mmol), Chloromethyl-dimethyl-phosphinoxide (12.0 g; 94.5 mmol), potassium carbonate (12.4 g; 90.0 mmol), sodium iodide (13.5 g; 90.0 mmol) and ACN (150 ml) is stirred at 80° C. for 3 days. After cooling to r.t., insolubles are filtered off and the filtrate is evaporated. The residue is purified by silica gel chromatography (DCM/(MeOH/aq. Ammonia 9:1) 0->15%).

$C_{12}H_{20}NO_2P$ ESI Mass spectrum: m/z=242 [M+H]$^+$

Intermediate XVII. 1

XVII.1

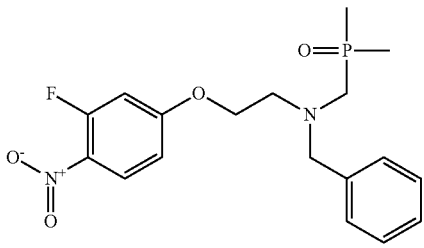

To a mixture of 3-fluoro-4-nitrophenol (10.3 g; 65.6 mmol), intermediate XVI.1 (17.5 g; 72.4 mmol), triphenyl-phosphine (18.9 g; 72.1 mmol) and DCM (200 ml) is added dropwise diisopropyl azodicarboxylate (16.6 g; 82.0 mmol). The mixture is stirred overnight and evaporated. The residue is purified by silica gel chromatography (DCM/(MeOH/aq. Ammonia 9:1) 0->12%.

$C_{18}H_{22}FN_2O_4P$ ESI Mass spectrum: m/z=381 [M+H]$^+$

Intermediate XVIII.1

XVIII.1

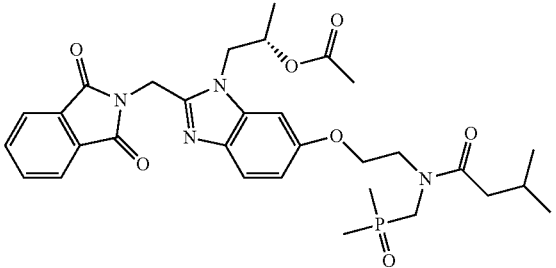

A mixture of intermediate II1.7 (1.70 g; 3.23 mmol), 3-methylbutanoic acid chloride (437 µl; 3.55 mmol), triethylamine (675 µl; 4.84 mmol) and DCM (20 ml) is stirred at r.t. for 2 h. The mixture is extracted with water. The organic layer is separated and evaporated.

$C_{31}H_{39}N_4O_7P$ ESI Mass spectrum: m/z=611 [M+H]$^+$

The following compounds are prepared accordingly applying the respective acid chloride as indicated. Depending upon conditions applied, the procedures may yield a chloride salt, a TFA salt or bis-TFA salt, a zwitterion or other salt forms.

| Intermediate No. | Structure | Acid chloride applied | Synthesis comment |
|---|---|---|---|
| XVIII.2 | 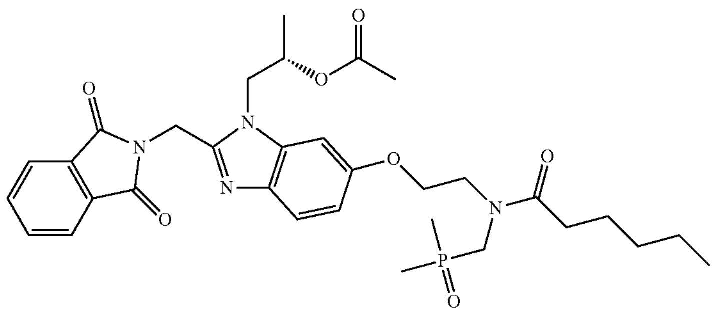 [SMILES: CCCCCC(=O)N(CCOc1ccc2nc(CN3C(=O)c4ccccc4C3=O)n(C[C@H](C)OC(C)=O)c2c1)CP(C)(C)=O] | Hexanoyl chloride | |

Intermediate XIX.1

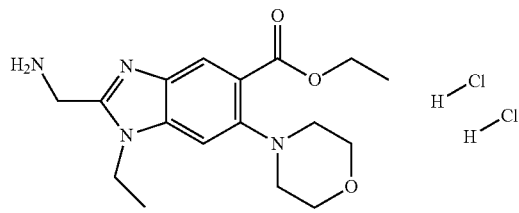

XIX.1

To a mixture of intermediate V.2 (12.0 g; 25.0 mmol), diethyl ether (100 ml) and EtOH (30 ml) is added aq. HCl (4 mol/l; 62.4 ml; 150 mmol). The mixture is stirred at r.t. for 6 h, then the precipitate formed is filtered and washed with diethyl ether and dried.

$C_{17}H_{24}N_4O_3$ ESI Mass spectrum: m/z=333 [M+H]$^+$

The following compounds are prepared accordingly applying the respective BOC derivates as indicated. Depending upon conditions applied, the procedures may yield a chloride salt, a TFA salt or bis-TFA salt, a zwitterion or other salt forms.

| Intermediate No. | Structure | BOC derivative applied | Synthesis comment |
|---|---|---|---|
| XIX.2 | 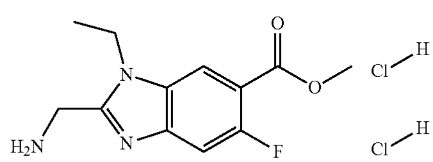 | V.4 | Reaction in HCl (4 mol/l in dioxane)/diethyl ether 1:2 for 6 h at r.t. |
| XIX.3 | 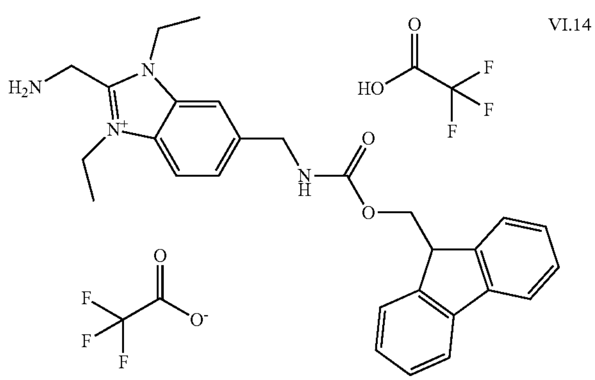 | VI.14 | Reaction in DCM/TFA 3:1 at r.t. for 3 h. Purification by RP-HPLC (modifier: TFA). |

Intermediate XX.1

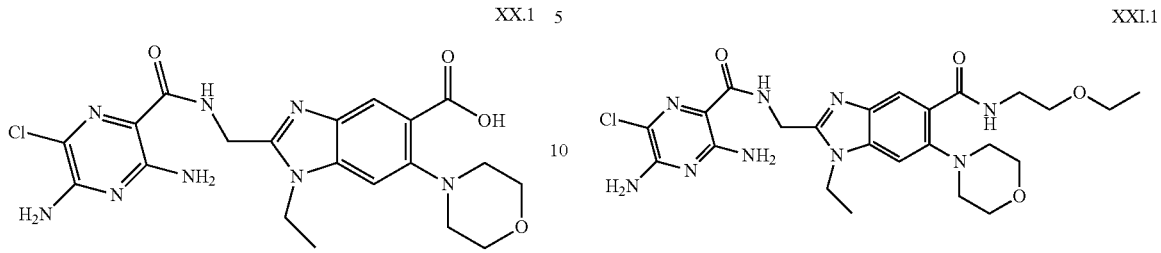

To a mixture of the ester intermediate VIII.3 (1.00 g; 1.89 mmol) in EtOH (10 ml) is added a KOH (623 mg; 9.44 mmol) in water (10 ml). The mixture is stirred overnight at 45° C. Aq. Hydrochlorc acid (4 mol/1) is added to adjust pH to ~5, then EtOH is removed by distillation. The precipitate formed upon cooling is filtered off, washed with water and dried (50° C.).

$C_{20}H_{23}ClN_8O_4$ ESI Mass spectrum: m/z=476 [M+H]$^+$

The following compounds are prepared accordingly applying the respective ester as indicated. Depending upon conditions applied, the procedures may yield a chloride salt, a TFA salt or bis-TFA salt, a zwitterion or other salt forms.

Intermediate XXI.1

To a mixture of carboxylic acid intermediate XX.1 (150 mg; 0.368 mmol), 2-ethoxyethylamine (46 µl; 0.442 mmol) and DMF (3.00 ml) is added TBTU (148 mg; 0.461 mmol) and Hünig's base (128 µl; 0.737 mmol). The mixture is stirred overnight at r.t., then water (15 ml) is added. The precipitate formed upon standing at 4° C. is filtered off, washed with small amounts of water and diethyl ether and dried (50° C.).

$C_{24}H_{32}ClN_9O_4$ ESI Mass spectrum: m/z=546 [M]$^+$

HPLC analytics: RT=0.84 min (HPLC method F)

The following intermediates are prepared accordingly from the respective carboxylic acid and the respective amine as indicated. Depending upon conditions applied, the syntheses may yield a free base, a TFA salt or other salt forms which can be applied equally to the syntheses of example compounds described below.

| Intermediate No. | Structure | ester applied | Synthesis comment |
|---|---|---|---|
| XX.2 | 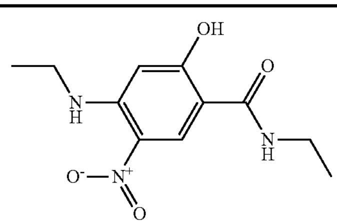 | VIII.4 | Reaction with aq. NaOH (2 mol/l)/dioxane 2:1 for 3 days at 90° C. |
| XX.3 | 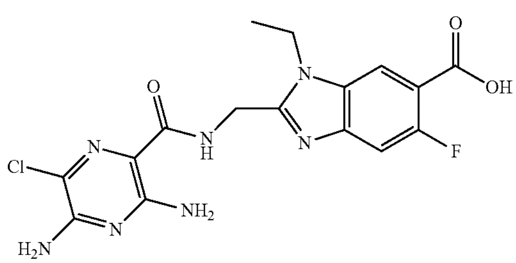 [SMILES: CCn1c(CNC(=O)c2nc(Cl)c(N)nc2N)nc2cc(F)c(C(=O)O)cc21] | XXIV.1 | Reaction with LiOH (4 eq.) in water/THF 4:1 at r.t. for 2 days |
| XX.4 | 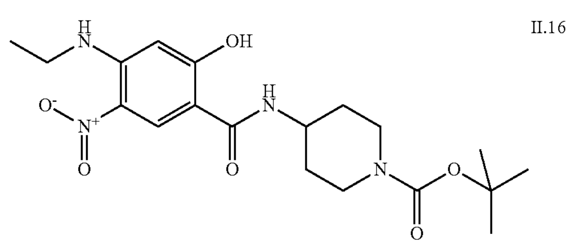 | II.16 | Reaction with aq. KOH (1 mol/l)/dioxane 1:1 for 24 h at 120° C. |

| Intermediate No. | Structure | Carboxylic acid applied | amine applied | Synthesis comment |
|---|---|---|---|---|
| XXI.2 | 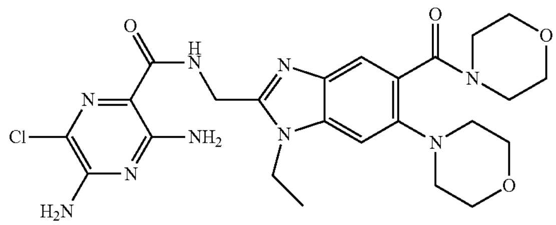 [SMILES: CCn1c(CNC(=O)c2nc(Cl)c(N)nc2N)nc2cc(C(=O)N3CCOCC3)c(N3CCOCC3)cc21] | XX.1 | Morpholine | |
| XXI.3 | 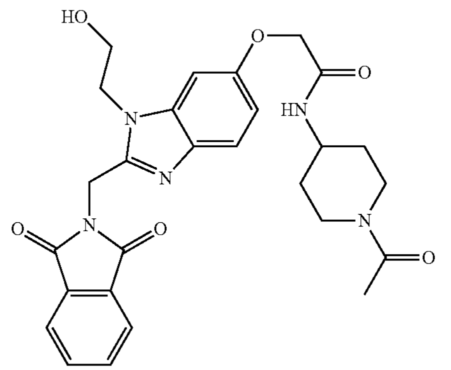 [SMILES: CC(=O)N1CCC(NC(=O)COc2ccc3nc(CN4C(=O)c5ccccc5C4=O)n(CCO)c3c2)CC1] | XII.2 | NH₂ | Purification by silica gel chromatography (DCM/MeOH 0->12%) |

Intermediate XXII.1

XXII.1

A mixture of intermediate IV.6 (3.00 g; 6.92 mmol), 3-chloropropylphosphonic acid (1.10 g; 6.92 mmol), Dicyclohexyl carbodiimide (2.86 g; 13.8 mmol) and DMAP (85 mg; 0.692 mmol) in THF (50 ml) is stirred at 50° C. over night. Water is added and the mixture is stirred for further 20 min. The precipitate is filtered off, refluxed in MeOH (70 ml), cooled to r.t. and filtrated. The combined filtrates are evaporated to yield the title compound.

$C_{28}H_{33}ClN_3O_6P$ ESI Mass spectrum: m/z=574 [M+H]+

Intermediate XXIII.1

XXIII.1

A mixture of intermediate XXII.1 (4.20 g; 7.32 mmol), lithium bromide (3.18 g; 36.6 mmol), trimethylamine (4.2 M in ethanol; 10.0 ml; 42.0 mmol) and methanol (20 ml) is stirred at 60° C. overnight. Water (20 ml) is added, insolubles are filtered off and discarded, and the filtrate is evaporated. The residue is purified by RP-HPLC (Sunfire; water/ACN, modifier: TFA) to yield the title compound.

$C_{31}H_{43}N_4O_7P$ ESI Mass spectrum: m/z=597 [M+H]+

Intermediate XXIV.1

XXIV.1

To a mixture of intermediate XIX.2 (1.50 g; 4.63 mmol), intermediate B.1 (1.44 g; 4.40 mmol) and THF (40 ml) is added Hünig's base (2.80 ml; 16.2 mmol). The mixture is stirred overnight at 50° C., then cooled to r.t. Insolubles are filtered off with suction and the filtrate is evaporated. The residue is taken up in water (30 ml), the solid formed is filtered, washed with water and diethyl ether and dried.

$C_{17}H_{17}ClFN_7O_3$ ESI Mass spectrum: m/z=422 [M+H]⁺

HPLC analytics: RT=0.88 min (HPLC method F)

Intermediate XXV. 1

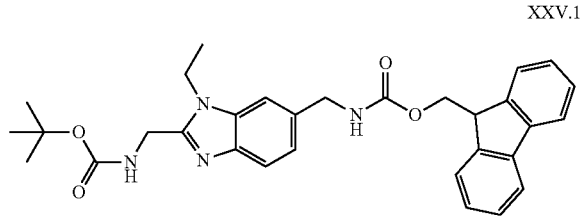 [SMILES: CCn1c(CNC(=O)OC(C)(C)C)nc2ccc(CNC(=O)OCC3c4ccccc4-c4ccccc43)cc21]

To a solution of intermediate III.13 (17.2 g; 56.5 mmol) in dioxane (250 ml) and THF (250 ml) are added at 50° C. 9-fluorenylmethyl chloroformate (15.3 g; 59.3 mmol) and potassium carbonate (8.59 g; 62.1 mmol). The mixture is stirred for 3 h, then evaporated. The residue is taken up in DCM (1 l) and extracted three times with water. The organic layer is dried (MgSO4) and evaporated. The residue is triturated with diethyl ether, filtered off with suction and dried (60° C.). The product is taken to the next step without further purification.

Intermediate XXVI.1

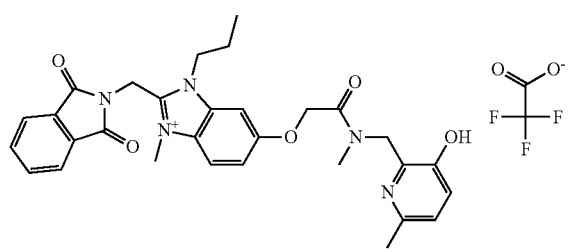

A mixture of intermediate XII.5 (1.00 g; 2.25 mmol), 1,1'-carbonyldiimidazole (475 mg; 2.93 mmol) and THF (10 ml) is stirred for 30 min at 50° C. 6-Methyl-2-methylaminomethyl-pyridin-3-ol dihydrochloride (609 mg; 2.70 mmol) is added, the mixture is stirred overnight and evaporated. The product is purified by RP-HPLC (modifier: TFA).
$C_{30}H_{32}N_5O_5 \times TFA$ ESI Mass spectrum: m/z=542 [M]$^+$
HPLC analytics: RT=0.37 min (HPLC method G)

Intermediate XXVII.1

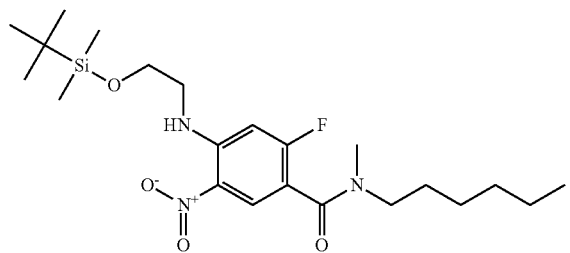

To an ice-cold mixture of intermediate 11.15 (11.4 g; 33.3 mmol), imidazole (4.99 g; 73.3 mmol) and DMF (70 ml) is added dropwise tert-butyldimethylchlorosilane (5.52 g; 36.6 mmol) in DCM (30 ml). The mixture is stirred overnight at r.t. and then evaporated. The residue is taken up in DCM, extracted with water. The organic layer is separated, dried (MgSO$_4$) and evaporated. The residue is purified by silica gel chromatography (DCM/MeOH 0->10%).
$C_{22}H_{38}FN_3O_4Si \times TFA$ ESI Mass spectrum: m/z=456 [M+H]$^+$ Intermediate XXVIII.1

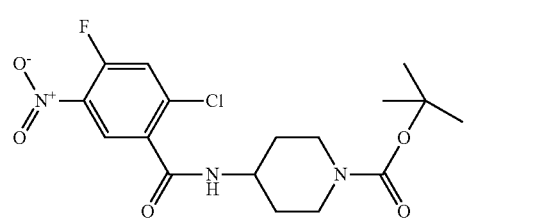

To a solution of 2-Chloro-4-fluoro-5-nitro-benzoyl chloride (100 g; 420 mmol; prepared from the respective acid by treatment with thionyl chloride in DCM/cat. DMF) are added first 1-BOC-4-aminopiperidine (96.6 g; 483 mmol), then triethylamine (130 ml). The mixture is stirred for 1 h at r.t., then extracted with water. The organic layer is separated, dried (Na$_2$SO$_4$) and evaporated. The residue is purified by silica gel chromatography (petrol ether/EE 30->50%)
$C_{17}H_{21}ClFN_3O_5$ TLC: Rf=0.6 (Silica; hexane/EE 1:1)

Intermediate XXIX.1

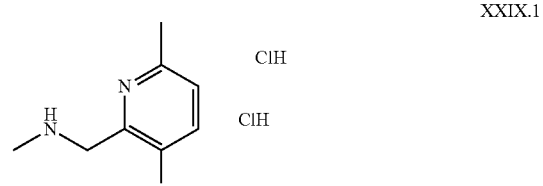

The compound is prepared according to the procedure described in: Stempel, Buzzi; Journal of the American Chemical Society 71 (1949) p. 2968ff.

The following intermediates are prepared accordingly from the respective pyridine and amine. Depending upon conditions applied, the syntheses may yield a free base, a TFA salt or other salt forms which can be applied equally to the syntheses of example compounds described below.

| Example | Structure | Pyridine applied | Amine applied |
|---|---|---|---|
| XXIX.2 | (structure) | (structure) | (structure) |

Intermediate XXX.1

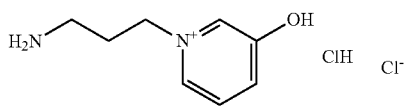

A mixture of 3-hydroxy-pyridine (500 mg; 5.26 mmol), tert-butyl N-(3-(tosyloxy)propyl)carbamate (1.73 g; 5.26 mmol) and THF (10 ml) is stirred at 65° C. overnight. The mixture is evaporated to dryness, taken up in HCl (4 mol/l in dioxane; 10.0 ml; 40.0 mmol), ACN (15 ml) and EE (15 ml). The mixture is stirred overnight, the precipitate is filtered off, washed with EE and dried at 50° C.

$C_8H_{13}N_2O \times HCl \times Cl$ ESI Mass spectrum: m/z=153 $[M+H]^+$

7.2 SYNTHESIS OF EXAMPLES

Example 1.01

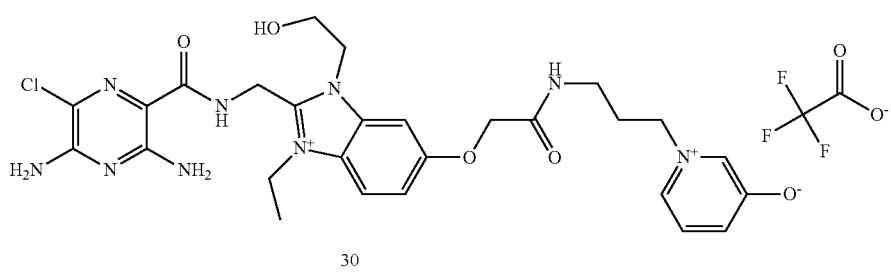

The amine intermediate XV. 15 (150 mg; 0.222 mmol) is added to a mixture of intermediate A. 1 (41.0 mg; 0.220 mmol), TBTU (71.0 mg; 0.220 mmol), triethylamine (93.0 µl; 0.660 mmol) and DMF (3.0 ml). The mixture is stirred at r.t. overnight, then evaporated and the crude product is purified by RP-HPLC (modifier: TFA).

$C_{27}H_{33}ClN_9O_5 \times C_2F_3O_2$ ESI Mass spectrum: m/z=598 $[M]+$

HPLC analytics: RT=0.39 min (HPLC method E)

The following example compounds are prepared accordingly from intermediate A.1 and the respective amine intermediate as indicated. Depending upon conditions applied, the syntheses may yield a TFA salt, a zwitterion or other salt forms.

| Example No. | Structure | Amine applied | M+ | RT | HPLC method |
|---|---|---|---|---|---|
| 1.02 | (structure) | XV.2 | 659 | 0.85 | B |

-continued

| Example No. | Structure | Amine applied | M+ | RT | HPLC method |
|---|---|---|---|---|---|
| 1.03 | 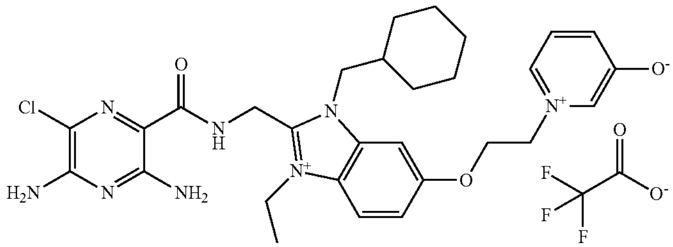 [SMILES: CC[n+]1c(CNC(=O)c2nc(Cl)c(N)nc2N)n(CC2CCCCC2)c2cc(OCC[n+]3cccc([O-])c3)ccc21 ; O=C([O-])C(F)(F)F] | XV.7 | 579 | 0.5 | E |
| 1.04 | 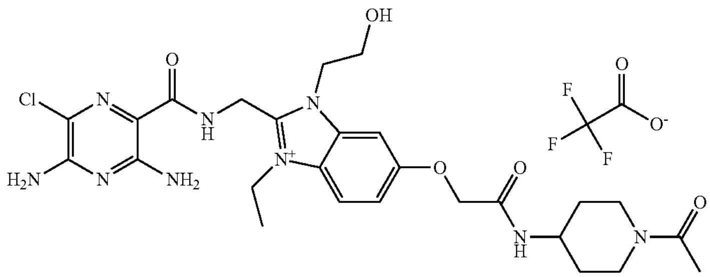 [SMILES: CC[n+]1c(CNC(=O)c2nc(Cl)c(N)nc2N)n(CCO)c2cc(OCC(=O)NC3CCN(C(C)=O)CC3)ccc21 ; O=C([O-])C(F)(F)F] | XV.8 | 588 | 0.69 | B |
| 1.05 | 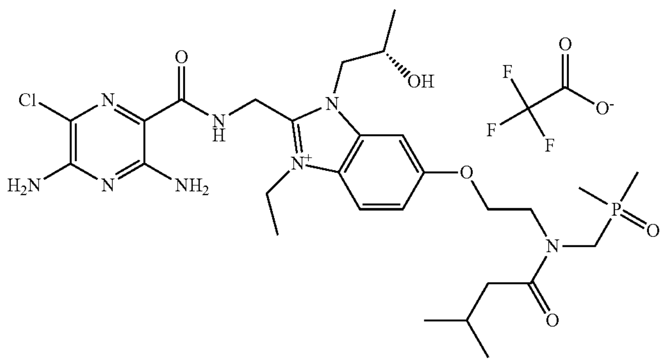 [SMILES: CC[n+]1c(CNC(=O)c2nc(Cl)c(N)nc2N)n(C[C@H](C)O)c2cc(OCCN(CP(C)(C)=O)C(=O)CC(C)C)ccc21 ; O=C([O-])C(F)(F)F] | XV.4 | 637 | 0.78 | B |
| 1.06 | 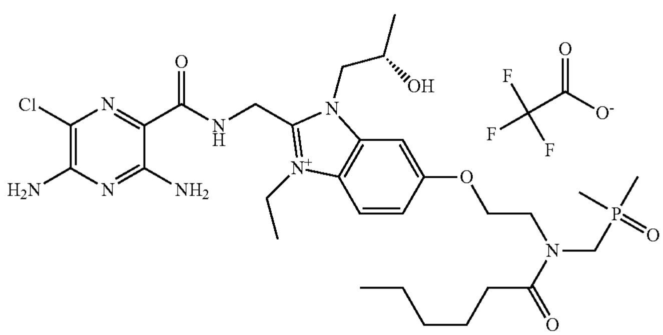 [SMILES: CCCCCC(=O)N(CCOc1ccc2c(c1)n(C[C@H](C)O)c(CNC(=O)c1nc(Cl)c(N)nc1N)[n+]2CC)CP(C)(C)=O ; O=C([O-])C(F)(F)F] | XV.5 | 651 | 0.57 | E |
| 1.07 | 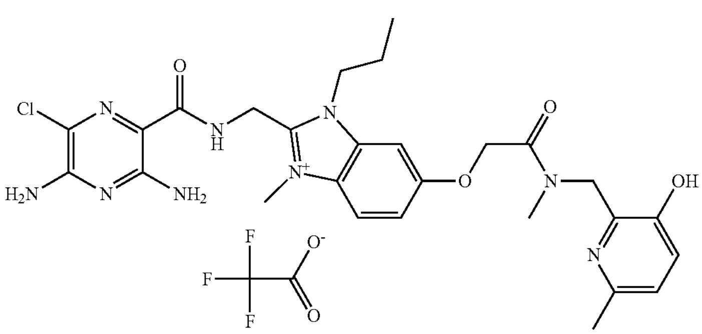 [SMILES: CCCn1c(CNC(=O)c2nc(Cl)c(N)nc2N)[n+](C)c2ccc(OCC(=O)N(C)Cc3nc(C)ccc3O)cc21 ; O=C([O-])C(F)(F)F] | XV.11 | 582 | 0.34 | G |

-continued

| Example No. | Structure | Amine applied | M+ | RT | HPLC method |
|---|---|---|---|---|---|
| 1.08 | 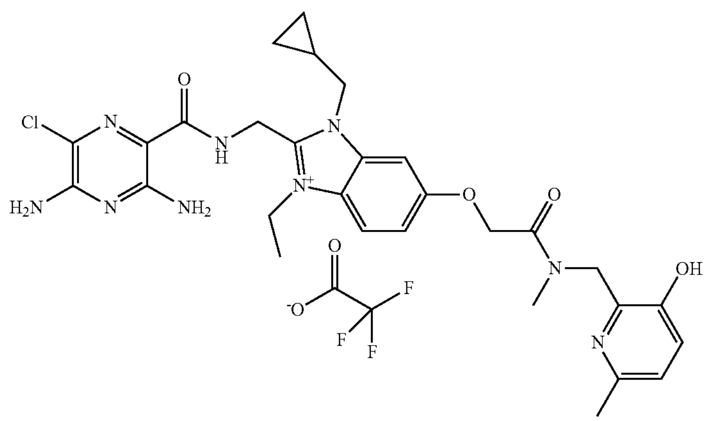 | XV.12 | 608 | 0.71 | B |
| 1.09 | 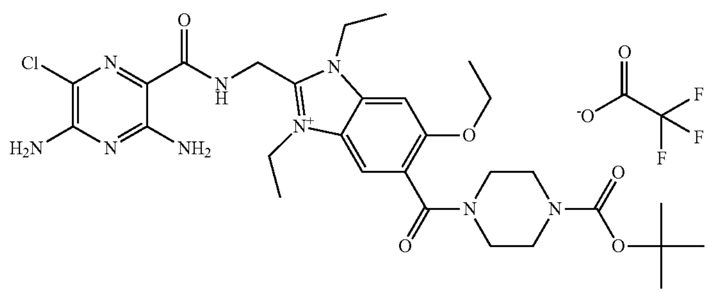 | XV.1 | 630 | 0.88 | B |
| 1.10 | 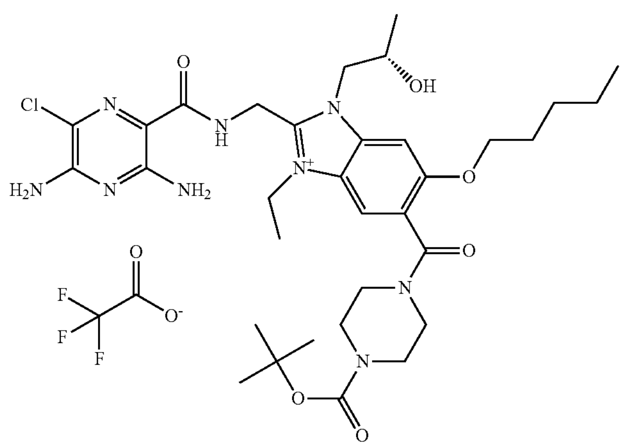 [SMILES: CCCCCOc1cc2c(cc1C(=O)N1CCN(C(=O)OC(C)(C)C)CC1)[n+](CC)c(CNC(=O)c1nc(Cl)c(N)nc1N)n2C[C@H](C)O ; O=C([O-])C(F)(F)F] | XV.3 | 702 | 0.94 | B |
| 1.11 | 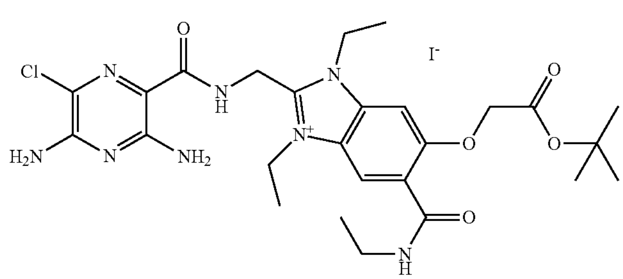 [SMILES: CCNC(=O)c1cc2c(cc1OCC(=O)OC(C)(C)C)n(CC)c(CNC(=O)c1nc(Cl)c(N)nc1N)[n+]2CC ; [I-]] | VII.2 | 575 | 0.87 | B |

-continued

| Example No. | Structure | Amine applied | M+ | RT | HPLC method |
|---|---|---|---|---|---|
| 1.12 | 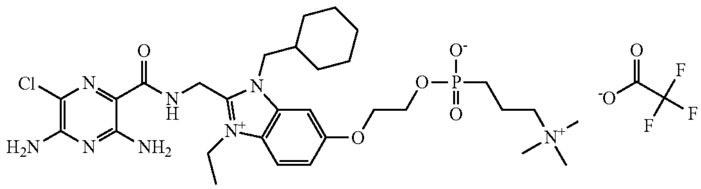 | XV.6 | 665 | 0.76 | B |
| 1.13 | 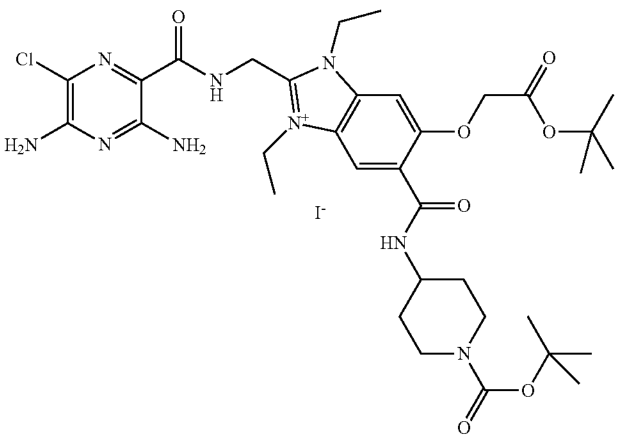 [SMILES: CCn1c(CNC(=O)c2nc(Cl)c(N)nc2N)[n+](CC)c2cc(C(=O)NC3CCN(C(=O)OC(C)(C)C)CC3)c(OCC(=O)OC(C)(C)C)cc21 ; [I-]] | VII.4 | 730 | 0.97 | B |
| 1.14 | 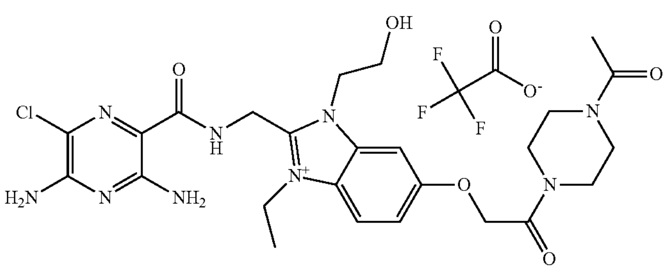 [SMILES: CC[n+]1c(CNC(=O)c2nc(Cl)c(N)nc2N)n(CCO)c2cc(OCC(=O)N3CCN(C(C)=O)CC3)ccc21 ; O=C([O-])C(F)(F)F] | XV.8 | 574 | 0.69 | B |
| 1.15 | 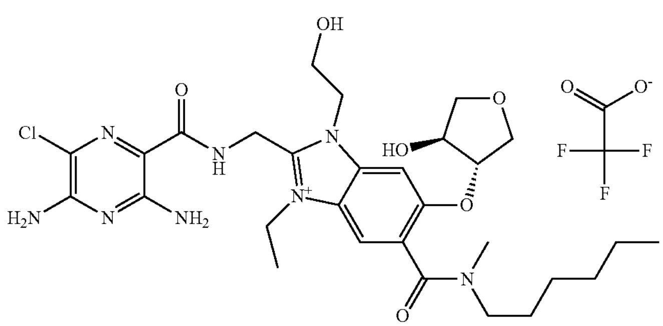 [SMILES: CCCCCCN(C)C(=O)c1cc2c(cc1O[C@H]1COC[C@@H]1O)n(CCO)c(CNC(=O)c1nc(Cl)c(N)nc1N)[n+]2CC ; O=C([O-])C(F)(F)F] | XV.13 | 633 | 0.49 | G |
| 1.16 | 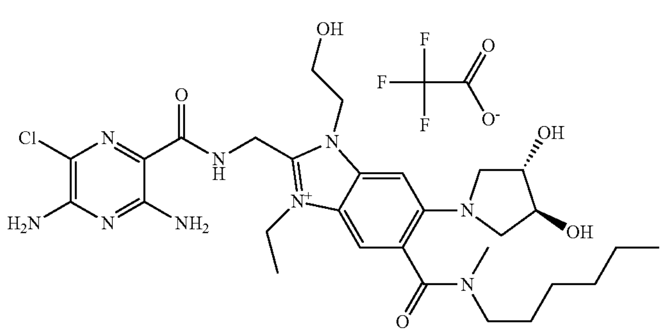 [SMILES: CCCCCCN(C)C(=O)c1cc2c(cc1N1C[C@H](O)[C@@H](O)C1)n(CCO)c(CNC(=O)c1nc(Cl)c(N)nc1N)[n+]2CC ; O=C([O-])C(F)(F)F] | XV.14 | 633 | 0.49 | G |

Example 2.01

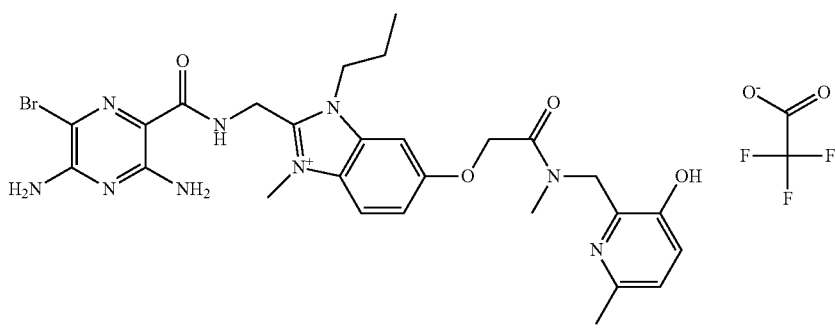

The compound is prepared from intermediate XV.11 and intermediate A.2 according to the procedure described for example 1.01.

$C_{27}H_{33}BrN_9O_4 \times C_2F_3O_2$ ESI Mass spectrum: m/z=626 [M]+

HPLC analytics: RT=0.35 min (HPLC method G)

Example 3.01

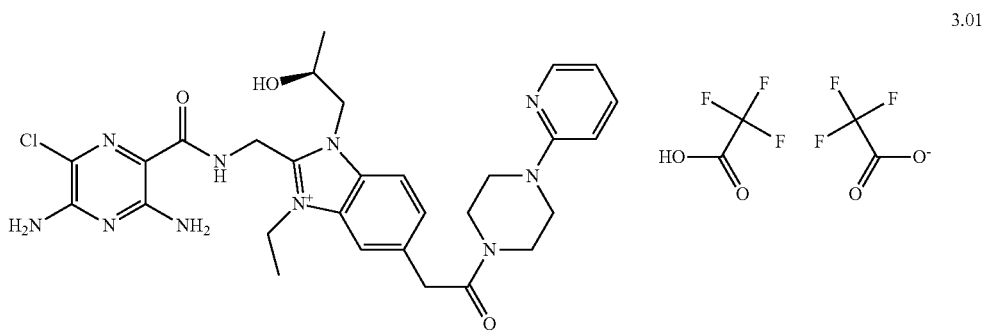 [SMILES: CC[n+]1c(CNC(=O)c2nc(Cl)c(N)nc2N)n(C[C@H](C)O)c2ccc(CC(=O)N3CCN(c4ccccn4)CC3)cc21 ; O=C(O)C(F)(F)F ; O=C([O-])C(F)(F)F]

The amine 1-(2-pyridinyl)-piperazine (27.0 mg; 0.168 mmol) is added to a mixture of the acid intermediate XII.4 (120 mg; 0.1698 mmol), TBTU (54.0 mg; 0.168 mmol), triethylamine (94.0 μl; 0.673 mmol) and DMF (4.0 ml). The mixture is stirred at r.t. overnight, then evaporated. The crude product is purified by RP-HPLC (modifier: TFA).

$C_{29}H_{36}ClN_{10}O_3 \times C_2F_3O_2 \times C_2HF_3O_2$ ESI Mass spectrum: m/z=607 [M]+

HPLC analytics: RT=0.70 min (HPLC method L)

The following example compounds are prepared accordingly from the respective amine and acid as indicated. Depending upon conditions applied, the syntheses may yield a TFA salt, a zwitterion or other salt forms.

| Example No. | Structure | Amine applied | Acid applied | M+ | RT | HPLC method |
|---|---|---|---|---|---|---|
| 3.02 | (structure) | XXIX.1 | XII.1 | 582 (M + H)+ | 0.34 | A |

-continued
| Example No. | Structure | Amine applied | Acid applied | M+ | RT | HPLC method |
|---|---|---|---|---|---|---|
| 3.03 | 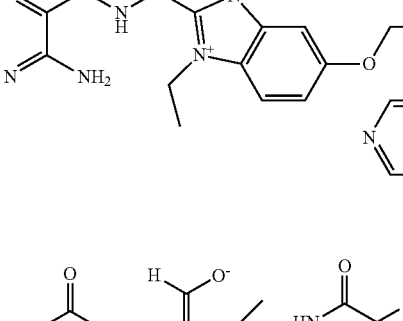 | 3-amino-5-hydroxy-pyridine | XII.1 | 540 | 0.34 | G |
| 3.04 | 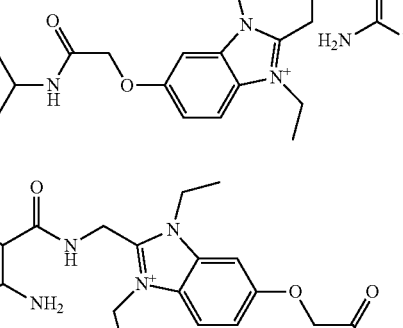 | 4-amino-1-hexyl-piperidine | XII.1 | 614 | 3.48 | C |
| 3.05 | 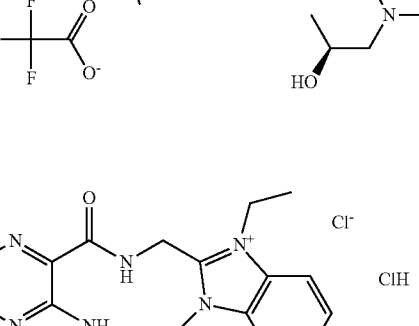 | XXIX.2 | XII.1 | 626 | 0.35 | A |
| 3.06 | 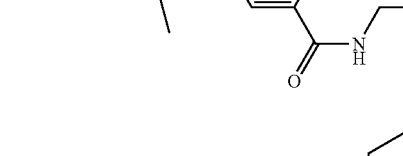 | 2-(dimethyl-amino)-ethyl-amine | VI.15 | 488 | 0.62 | B |
| 3.07 | 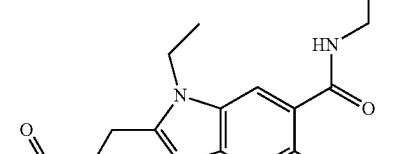 | 3-(dimethyl-amino)-propyl-amine | XII.3 | 520 | 2.70 | C |

-continued
| Example No. | Structure | Amine applied | Acid applied | M+ | RT | HPLC method |
|---|---|---|---|---|---|---|
| 3.08 | 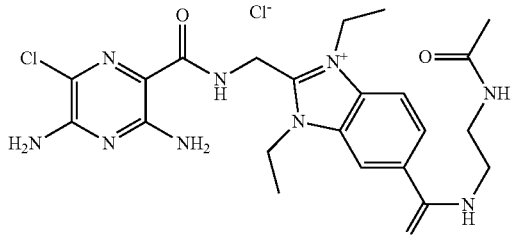 | 2-acetyl-amino-ethyl-amine | VI.15 | 502 | 0.68 | B |
| 3.09 | 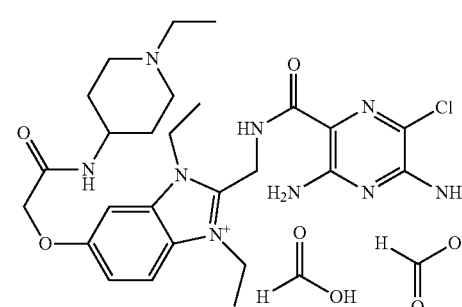 | 4-amino-1-ethyl-piperi-dine | XII.1 | 558 | 3.00 | C |
| 3.10 | 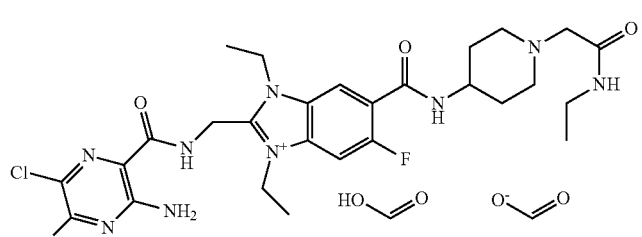 | 2-(4-Amino-piperi-din-1-yl)-N-ethyl-aceta-mide | XII.3 | 603 | 2.85 | C |
| 3.11 | 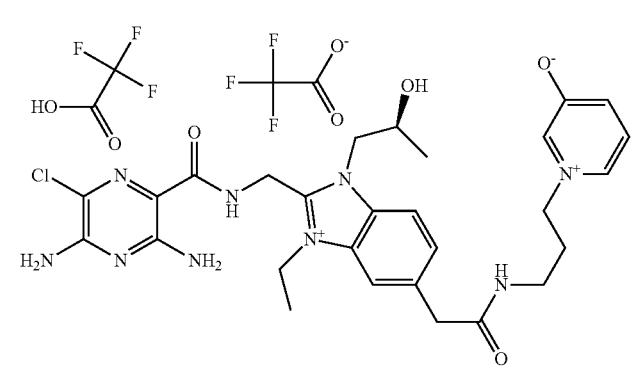 [SMILES: CC[n+]1c(CNC(=O)c2nc(Cl)c(N)nc2N)n(C[C@H](C)O)c2ccc(CC(=O)NCCC[n+]3cccc([O-])c3)cc21 ; O=C(O)C(F)(F)F ; O=C([O-])C(F)(F)F] | XXX.1 | XII.4 | 596 | 0.45 | H |
| 3.12 | 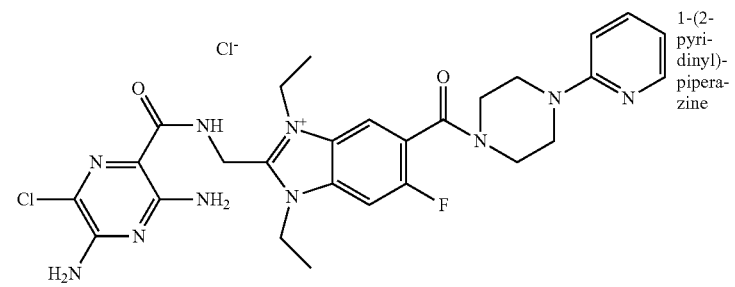 | 1-(2-pyri-dinyl)-pipera-zine | XII.3 | 581 | 2.93 | C |

-continued
| Example No. | Structure | Amine applied | Acid applied | M+ | RT | HPLC method |
|---|---|---|---|---|---|---|
| 3.13 | 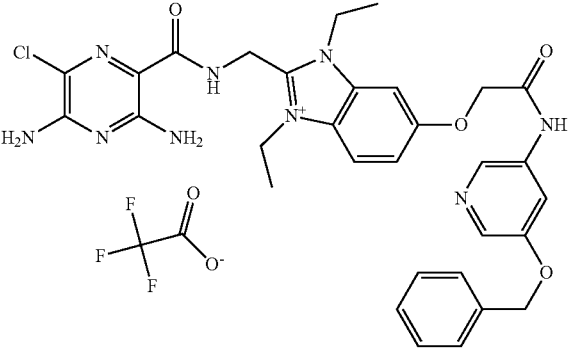 [SMILES: CCn1c(CNC(=O)c2nc(Cl)c(N)nc2N)[n+](CC)c2ccc(OCC(=O)Nc3cncc(OCc4ccccc4)c3)cc21 ; O=C([O-])C(F)(F)F] | 3-amino-5-benzyl-oxy-pyridine | XII.1 | 630 | 0.46 | G |
| 3.14 | 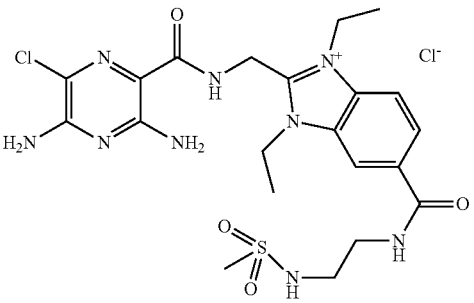 [SMILES: CCn1c(CNC(=O)c2nc(Cl)c(N)nc2N)[n+](CC)c2ccc(C(=O)NCCNS(C)(=O)=O)cc21 ; [Cl-]] | N-(2-amino-ethyl)-methane-sulfona-mide | VI.15 | 538 | 0.69 | B |
| 3.15 | 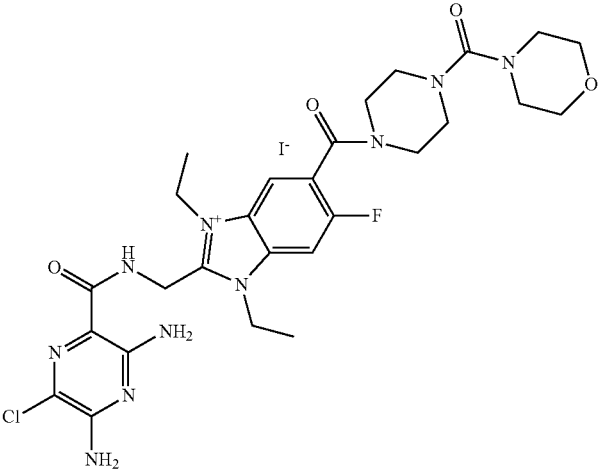 [SMILES: CCn1c(CNC(=O)c2nc(Cl)c(N)nc2N)[n+](CC)c2cc(C(=O)N3CCN(C(=O)N4CCOCC4)CC3)c(F)cc21 ; [I-]] | morpho-lin-4-yl-pipera-zin-1-yl-metha-none | XII.3 | 617 | 3.25 | C |
| 3.16 | 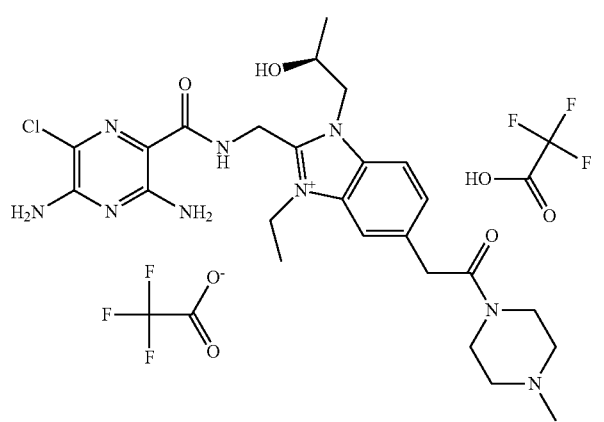 [SMILES: CC[n+]1c(CNC(=O)c2nc(Cl)c(N)nc2N)n(C[C@H](C)O)c2ccc(CC(=O)N3CCN(C)CC3)cc21 ; O=C([O-])C(F)(F)F ; O=C(O)C(F)(F)F] | 1-methyl-pipera-zine | XII.4 | 544 | 0.66 | L |

-continued
| Example No. | Structure | Amine applied | Acid applied | M+ | RT | HPLC method |
|---|---|---|---|---|---|---|
| 3.17 | 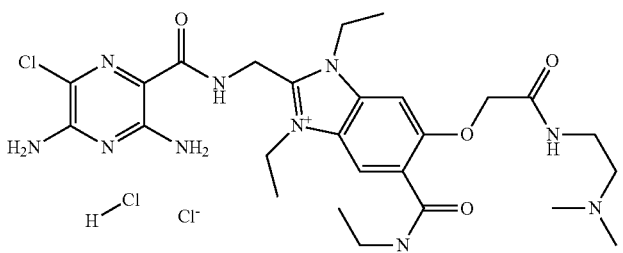 | 2-(di-methyl-amino)-ethyl-amine | 7.01 | 589 | 0.67 | B |
| 3.18 | 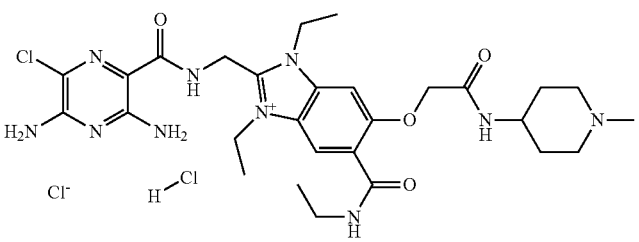 [SMILES: CCNC(=O)c1cc2c(cc1OCC(=O)NC1CCN(C)CC1)n(CC)c(CNC(=O)c1nc(Cl)c(N)nc1N)[n+]2CC ; [Cl-] ; Cl] | 1-methyl-4-amino-piperi-dine | 7.01 | 615 | 0.66 | B |
| 3.19 | 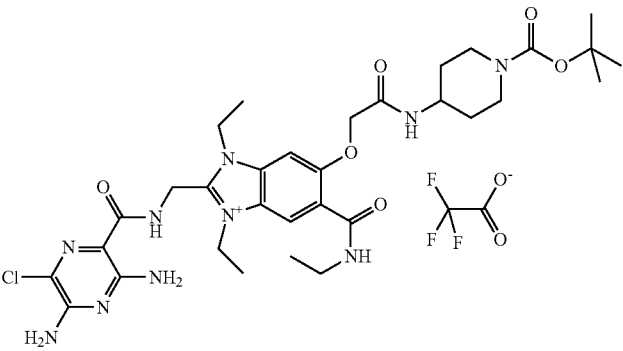 [SMILES: CCNC(=O)c1cc2c(cc1OCC(=O)NC1CCN(C(=O)OC(C)(C)C)CC1)n(CC)c(CNC(=O)c1nc(Cl)c(N)nc1N)[n+]2CC ; O=C([O-])C(F)(F)F] | 4-amino-1-tert-butoxy-carbonyl-piperi-dine | 7.01 | 701 | 0.88 | B |
| 3.20 | 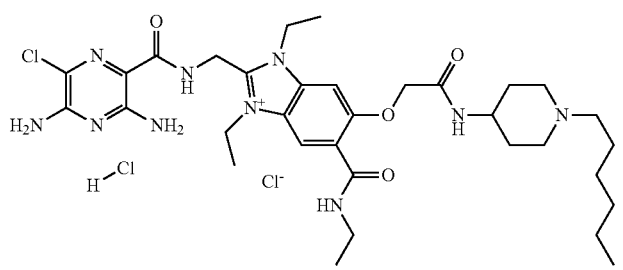 [SMILES: CCCCCCN1CCC(NC(=O)COc2cc3c(cc2C(=O)NCC)[n+](CC)c(CNC(=O)c2nc(Cl)c(N)nc2N)n3CC)CC1 ; Cl ; [Cl-]] | 4-amino-1-hexyl-piperi-dine | 7.01 | 343.5 (M + 2H)++ | 0.76 | B |
| 3.21 | 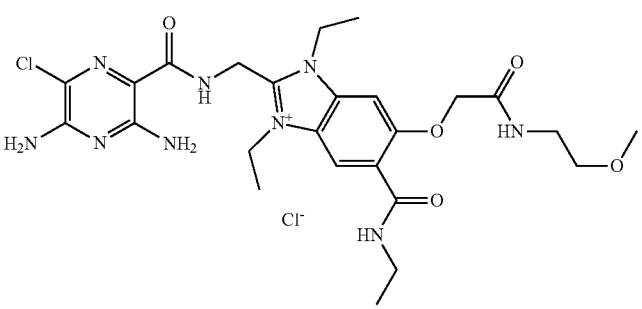 [SMILES: CCNC(=O)c1cc2c(cc1OCC(=O)NCCOC)n(CC)c(CNC(=O)c1nc(Cl)c(N)nc1N)[n+]2CC ; [Cl-]] | 2-methoxy-ethyl-amine | 7.01 | 576 | 0.75 | B |

-continued
| Example No. | Structure | Amine applied | Acid applied | M+ | RT | HPLC method |
|---|---|---|---|---|---|---|
| 3.22 | 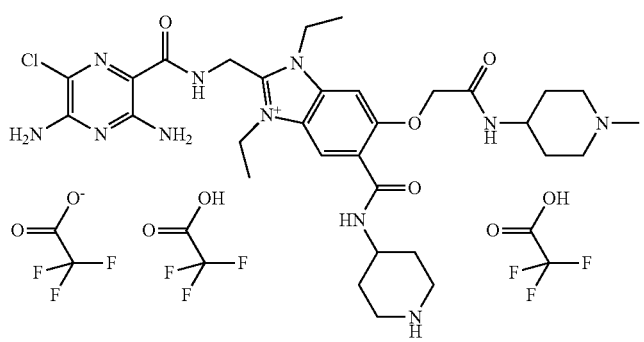 [SMILES: O=C([O-])C(F)(F)F ; CCn1c(CNC(=O)c2nc(Cl)c(N)nc2N)[n+](CC)c2cc(C(=O)NC3CCNCC3)c(OCC(=O)NC3CCN(C)CC3)cc21 ; O=C(O)C(F)(F)F ; O=C(O)C(F)(F)F] | 4-amino-1-methyl-piperidine | 9.01 | 670 | 0.28 | A |
| 3.23 | 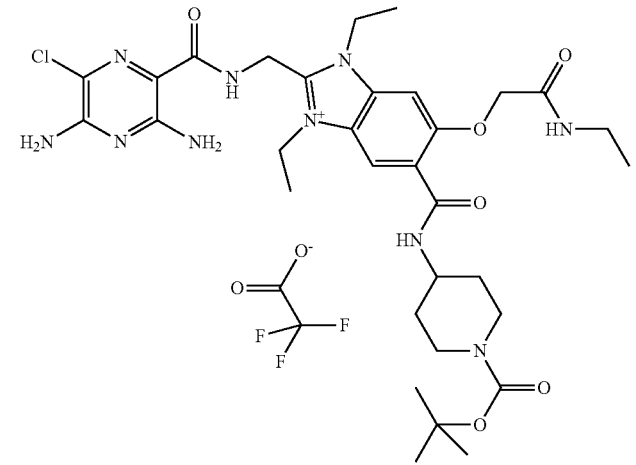 [SMILES: CCNC(=O)COc1cc2c(cc1C(=O)NC1CCN(C(=O)OC(C)(C)C)CC1)[n+](CC)c(CNC(=O)c1nc(Cl)c(N)nc1N)n2CC ; O=C([O-])C(F)(F)F] | ethylamine | 9.01 | 701 | 0.88 | B |
| 3.24 | 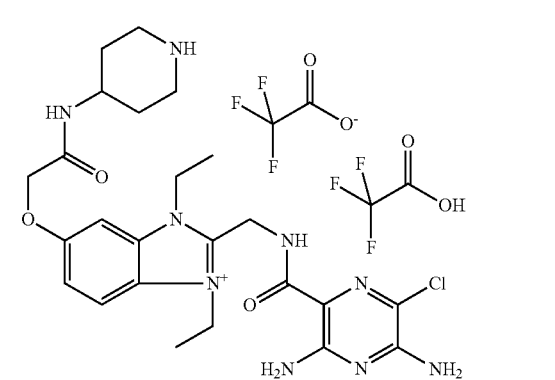 [SMILES: CCn1c(CNC(=O)c2nc(Cl)c(N)nc2N)[n+](CC)c2ccc(OCC(=O)NC3CCNCC3)cc21 ; O=C([O-])C(F)(F)F ; O=C(O)C(F)(F)F] | 4-amino-1-tert-butoxy-carbonyl-piperidine | XII.1 | 530 | 2.88 | C |
| 3.25 | 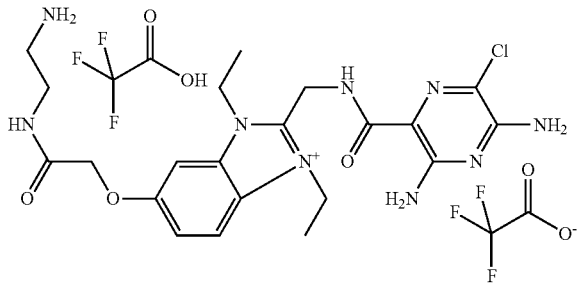 [SMILES: CCn1c(CNC(=O)c2nc(Cl)c(N)nc2N)[n+](CC)c2ccc(OCC(=O)NCCN)cc21 ; O=C(O)C(F)(F)F ; O=C([O-])C(F)(F)F] | N-(2-amino-ethyl)-tert-butyl-carbamate | XII.1 | 490 | 2.84 | C |

-continued

| Example No. | Structure | Amine applied | Acid applied | M+ | RT | HPLC method |
|---|---|---|---|---|---|---|
| 3.26 | 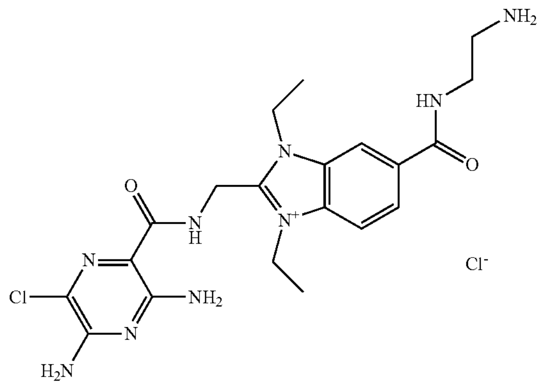 [SMILES: CCn1c(CNC(=O)c2nc(Cl)c(N)nc2N)[n+](CC)c2ccc(C(=O)NCCN)cc21 ; [Cl-]] | N-(2-aminoethyl)-tert-butyl-carbamate | VI.15 | 460 | 0.59 | B |

Example 4.01

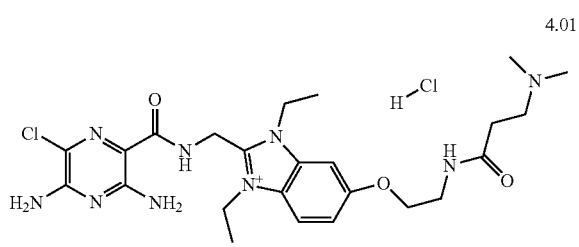 [SMILES: CCn1c(CNC(=O)c2nc(Cl)c(N)nc2N)[n+](CC)c2ccc(OCCNC(=O)CCN(C)C)cc21 ; Cl]

4.01

The amine intermediate IX. 1 (60.0 mg; 0.119 mmol) is added to a mixture of the acid 3-dimethylaminopropionic acid (13.9 mg; 0.119 mmol), HATU (45.1 mg; 0.119 mmol), Hünig's base (40.6 µl; 0.237 mmol) and DMF (3.0 ml). The mixture is stirred at r.t. overnight, then evaporated. The crude product is purified by RP-HPLC (modifier: TFA).

$C_{24}H_{35}ClN_9O_3 \times Cl \times HCl$ ESI Mass spectrum: m/z=532 [M]+

HPLC analytics: RT=0.68 min (HPLC method B)

The following example compounds are prepared accordingly from the respective amine and acid as indicated. Depending upon conditions applied, the syntheses may yield a chloride salt, a TFA salt, a zwitterion or other salt forms.

| Example No. | Structure | Amine applied | Acid applied | M+ | RT | HPLC method |
|---|---|---|---|---|---|---|
| 4.02 | 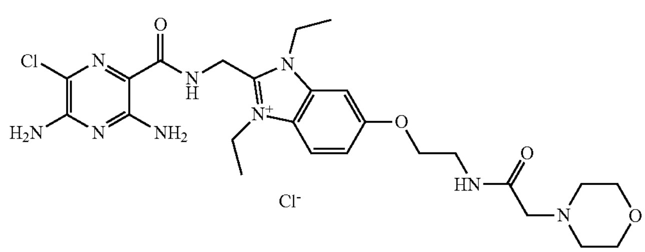 [SMILES: CCn1c(CNC(=O)c2nc(Cl)c(N)nc2N)[n+](CC)c2ccc(OCCNC(=O)CN3CCOCC3)cc21 ; [Cl-]] | IX.1 | morpholin-4-yl-acetic acid | 560 | 0.66 | B |
| 4.03 | 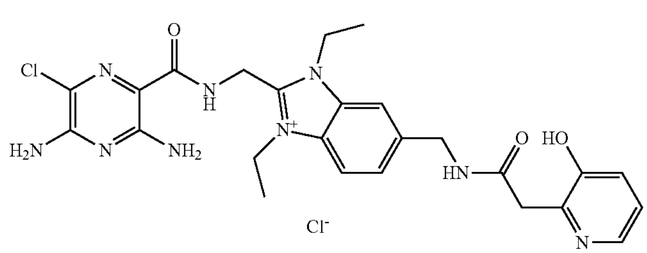 [SMILES: CCn1c(CNC(=O)c2nc(Cl)c(N)nc2N)[n+](CC)c2ccc(CNC(=O)Cc3ncccc3O)cc21 ; [Cl-]] | VII.3 | 3-hydroxy-pyridin-2-yl-acetic acid | 538 | 0.68 | B |

-continued

| Example No. | Structure | Amine applied | Acid applied | M+ | RT | HPLC method |
|---|---|---|---|---|---|---|
| 4.04 | 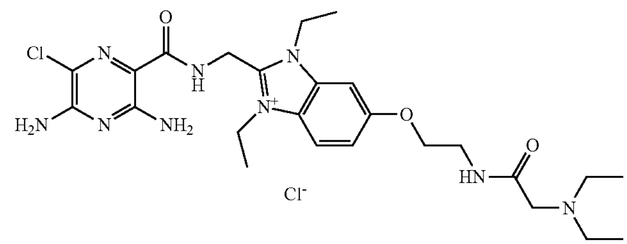 [SMILES: CCN(CC)CC(=O)NCCOc1ccc2c(c1)n(CC)c(CNC(=O)c1nc(Cl)c(N)nc1N)[n+]2CC ; [Cl-]] | IX.1 | 2-diethyl-amino-acetic acid | 546 | 0.68 | B |
| 4.05 | 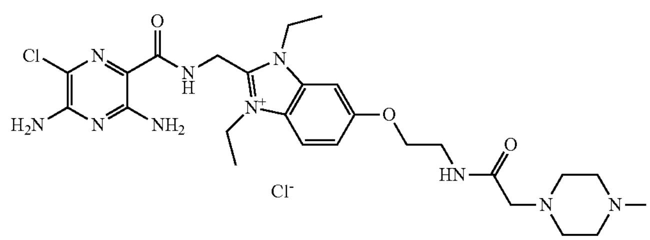 [SMILES: CCn1c(CNC(=O)c2nc(Cl)c(N)nc2N)[n+](CC)c2ccc(OCCNC(=O)CN3CCN(C)CC3)cc21 ; [Cl-]] | IX.1 | 1-methyl-pipera-zin-4-yl-acetic acid | 573 | 0.67 | B |
| 4.06 | 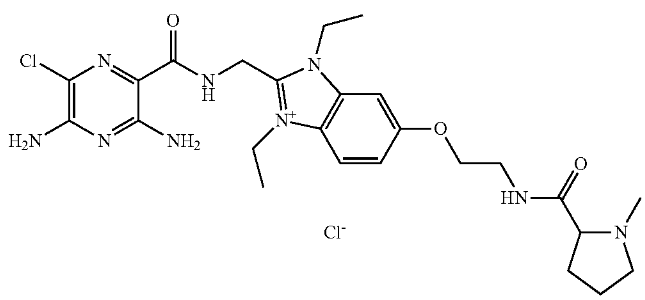 [SMILES: CCn1c(CNC(=O)c2nc(Cl)c(N)nc2N)[n+](CC)c2ccc(OCCNC(=O)C3CCCN3C)cc21 ; [Cl-]] | IX.1 | N-methyl-proline | 544 | 0.67 | B |
| 4.07 | 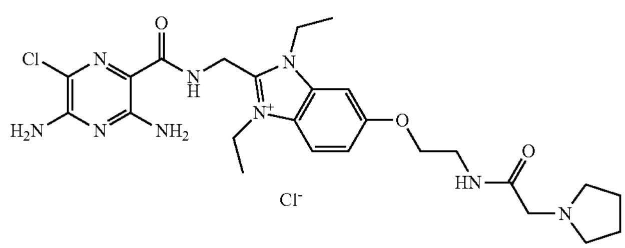 [SMILES: CCn1c(CNC(=O)c2nc(Cl)c(N)nc2N)[n+](CC)c2ccc(OCCNC(=O)CN3CCCC3)cc21 ; [Cl-]] | IX.1 | pyrroli-din-1-yl-acetic acid | 544 | 0.68 | B |
| 4.08 | 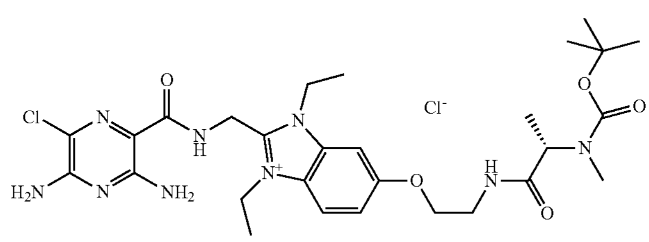 [SMILES: CCn1c(CNC(=O)c2nc(Cl)c(N)nc2N)[n+](CC)c2ccc(OCCNC(=O)[C@H](C)N(C)C(=O)OC(C)(C)C)cc21 ; [Cl-]] | IX.1 | (S)-2-(tert-butoxy-carbonyl-methyl-amino)-propionic acid | 618 | 0.5 | A |
| 4.09 | 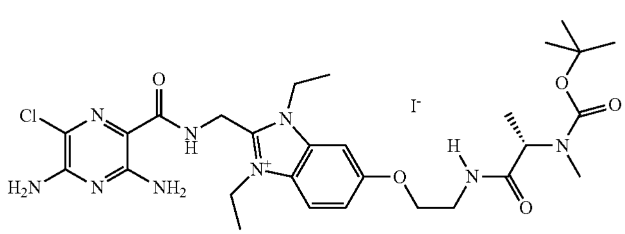 [SMILES: CCn1c(CNC(=O)c2nc(Cl)c(N)nc2N)[n+](CC)c2ccc(OCCNC(=O)[C@H](C)N(C)C(=O)OC(C)(C)C)cc21 ; [I-]] | IX.1 | (S)-2-(tert-butoxy-carbonyl-amino)-propionic acid | 604 | n.d. | n.d. |

-continued
| Example No. | Structure | Amine applied | Acid applied | M+ | RT | HPLC method |
|---|---|---|---|---|---|---|
| 4.10 | 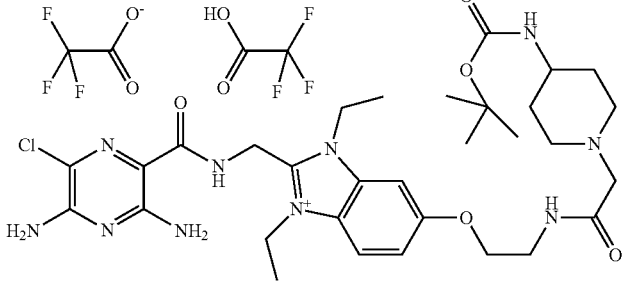 | IX.1 | (4-tert-butoxy-carbonyl-amino-piperidin-1-yl)-acetic acid | 673 | 0.77 | B |
| 4.11 | 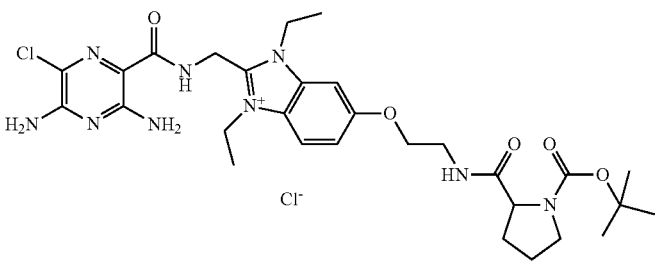 [SMILES: CCn1c(CNC(=O)c2nc(Cl)c(N)nc2N)[n+](CC)c2ccc(OCCNC(=O)C3CCCN3C(=O)OC(C)(C)C)cc21 ; [Cl-]] | IX.1 | N-tert-butoxy-carbonyl-proline | 630 | 0.83 | B |
| 4.12 | 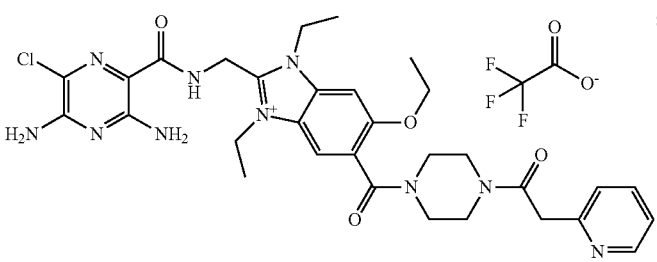 [SMILES: CCOc1cc2c(cc1C(=O)N1CCN(C(=O)Cc3ccccn3)CC1)[n+](CC)c(CNC(=O)c1nc(Cl)c(N)nc1N)n2CC ; O=C([O-])C(F)(F)F] | 8.02 | 2-(2-pyridinyl)-acetic acid | 649 | 0.34 | A |
| 4.13 | 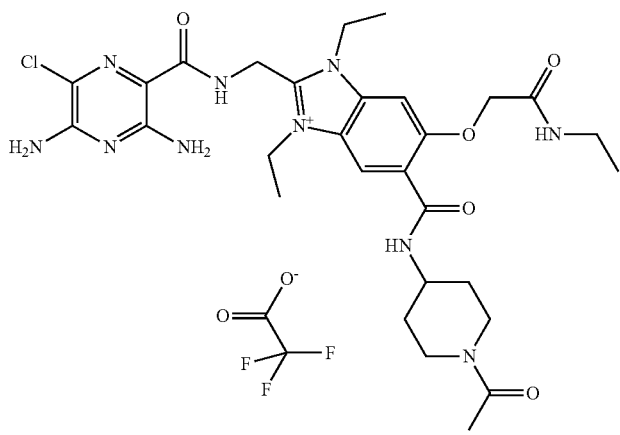 [SMILES: CCNC(=O)COc1cc2c(cc1C(=O)NC1CCN(C(C)=O)CC1)[n+](CC)c(CNC(=O)c1nc(Cl)c(N)nc1N)n2CC ; O=C([O-])C(F)(F)F] | 6.03 | acetic acid | 643 | 0.67 | A |

-continued
| Example No. | Structure | Amine applied | Acid applied | M+ | RT | HPLC method |
|---|---|---|---|---|---|---|
| 4.14 | 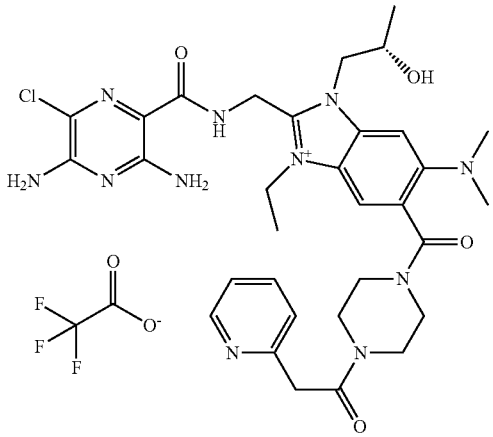 [SMILES: CC[n+]1c(CNC(=O)c2nc(Cl)c(N)nc2N)n(C[C@H](C)O)c2cc(N(C)C)c(C(=O)N3CCN(C(=O)Cc4ccccn4)CC3)cc21 ; O=C([O-])C(F)(F)F] | 8.01 | 2-pyridinyl-acetic acid | 678 | 0.66 | B |
| 4.15 | 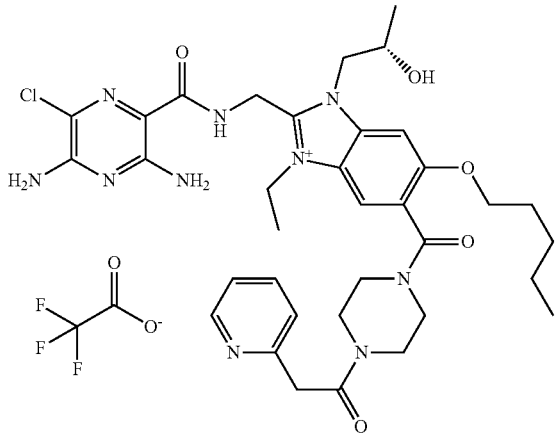 [SMILES: CCCCCOc1cc2c(cc1C(=O)N1CCN(C(=O)Cc3ccccn3)CC1)[n+](CC)c(CNC(=O)c1nc(Cl)c(N)nc1N)n2C[C@H](C)O ; O=C([O-])C(F)(F)F] | 8.03 | 2-pyridinyl-acetic acid | 721 | 0.75 | B |
| 4.16 | 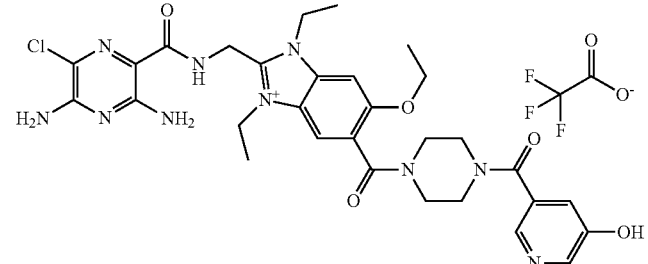 | 8.02 | 3-hydroxy-pyridin-5-yl-carboxylic acid | 651 | 0.35 | A |

| Example No. | Structure | Amine applied | Acid applied | M+ | RT | HPLC method |
|---|---|---|---|---|---|---|
| 4.17 | 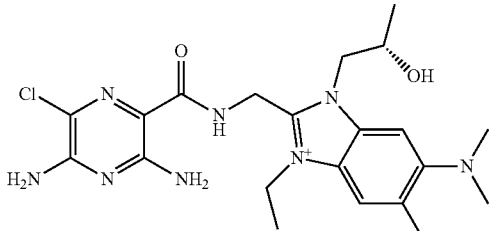 | 8.01 | 3-hydroxy-pyridin-5-yl-carboxylic acid | 680 | 0.68 | B |
| 4.18 | 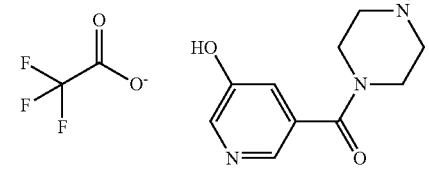 | 8.03 | 3-hydroxy-pyridin-5-yl-carboxylic acid | 723 | 0.76 | B |

Example 5.01

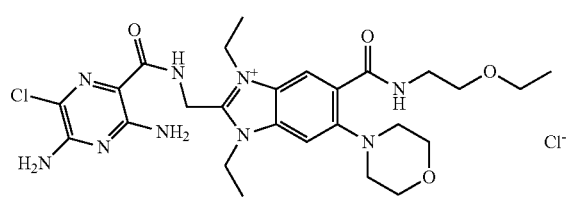

5.01

A mixture of the benzimidazole intermediate XXI.1 (80.0 mg; 0.122 mmol), Iodoethane (190 mg; 1.22 mmol) and ACN (3.0 ml) is heated to 110° C. for 1 h (closed vessel; microwave irradiation). The mixture is evaporated to dryness and the crude product is purified by RP-HPLC (modifier: TFA), taken up in aq. HCl (2 mol/l) and evaporated.

$C_{26}H_{37}ClN_9O_4 \times Cl$ ESI Mass spectrum: m/z=574 [M]+

HPLC analytics: RT=3.55 min (HPLC method C)

The following example compounds are prepared accordingly from the respective benzimidazole as indicated. Depending upon conditions applied, the syntheses may yield a TFA salt, a zwitterion or other salt forms.

| Example No. | Structure | Benzimidazole applied | M+ | RT | HPLC method |
|---|---|---|---|---|---|
| 5.02 | 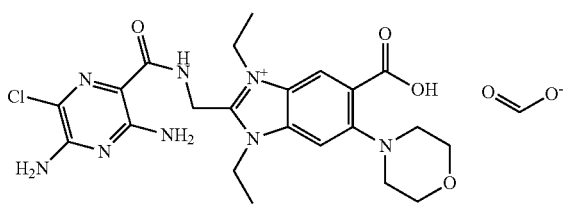 | XXI.2 | 572 | 3.26 | C |

Example 6.01

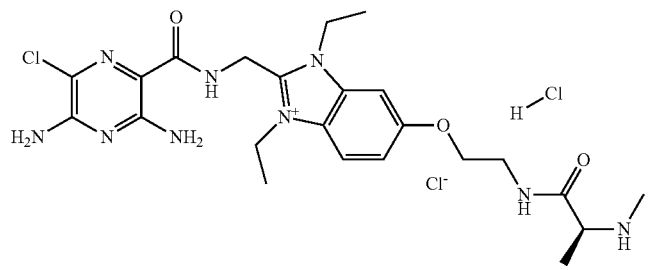

6.01

A mixture of intermediate VIII.3 (120 mg; 0.173 mmol) and aq. HCl (4 mol/l; 4.33 ml; 17.3 mmol) is heated to 80° C. for 2 h (closed vessel; microwave heating). The mixture is evaporated and the crude product is purified by RP-HPLC (modifier: formic acid).

$C_{22}H_{28}ClN_4O_4 \times CHO_2$ ESI Mass spectrum: m/z=503 [M]+

HPLC analytics: RT=2.97 min (HPLC method C)

The following example compounds are prepared accordingly from the respective BOC derivative as indicated. Depending upon conditions applied, the syntheses may yield a TFA salt, a zwitterion or other salt forms.

| Example No. | Structure | BOC derivative applied | M+ | RT | HPLC method |
|---|---|---|---|---|---|
| 6.02 | 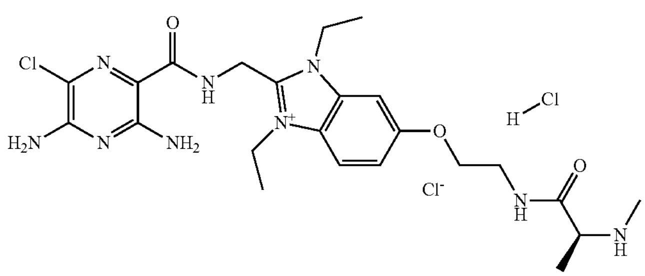 [SMILES: CCn1c(CNC(=O)c2nc(Cl)c(N)nc2N)[n+](CC)c2ccc(OCCNC(=O)[C@H](C)NC)cc21 ; [Cl-] ; Cl] | 4.08 | 518 | 0.34 | A |
| 6.03 | 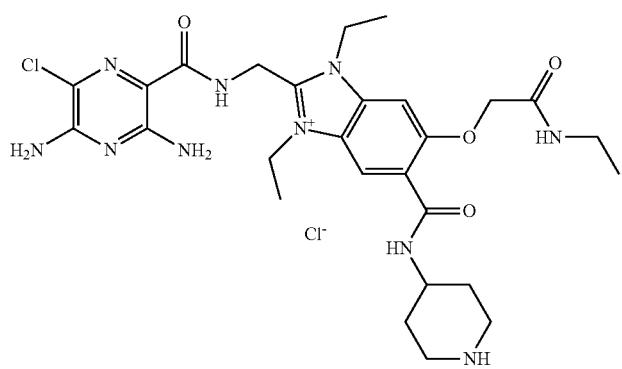 [SMILES: CCNC(=O)COc1cc2c(cc1C(=O)NC1CCNCC1)[n+](CC)c(CNC(=O)c1nc(Cl)c(N)nc1N)n2CC ; [Cl-]] | 3.23 | 601 | 0.32 | A |

-continued

| Example No. | Structure | BOC derivative applied | M+ | RT | HPLC method |
|---|---|---|---|---|---|
| 6.04 | 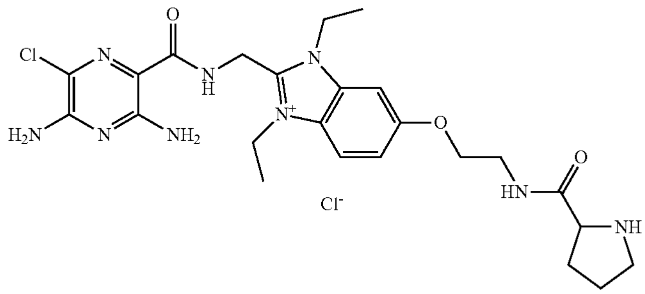 [SMILES: CCn1c(CNC(=O)c2nc(Cl)c(N)nc2N)[n+](CC)c2ccc(OCCNC(=O)C3CCCN3)cc21 ; [Cl-]] | 4.11 | 530 | 0.67 | B |
| 6.05 | 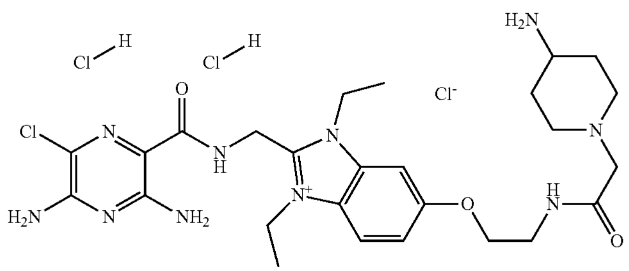 [SMILES: CCn1c(CNC(=O)c2nc(Cl)c(N)nc2N)[n+](CC)c2ccc(OCCNC(=O)CN3CCC(N)CC3)cc21 ; Cl ; Cl ; [Cl-]] | 4.1 | 573 | 0.65 | B |
| 6.06 | 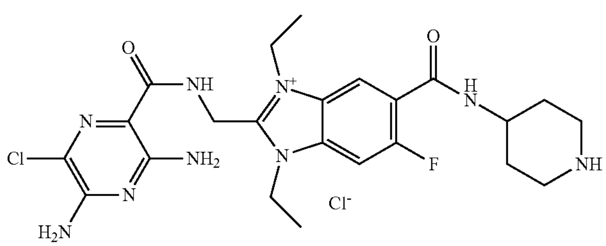 [SMILES: CCn1c(CNC(=O)c2nc(Cl)c(N)nc2N)[n+](CC)c2cc(C(=O)NC3CCNCC3)c(F)cc21 ; [Cl-]] | VI.11 | 518 | 2.74 | C |
| 6.07 | 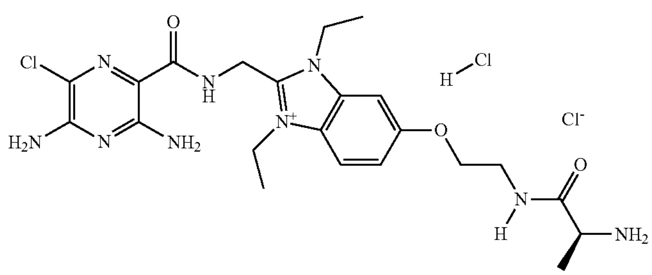 [SMILES: CCn1c(CNC(=O)c2nc(Cl)c(N)nc2N)[n+](CC)c2ccc(OCCNC(=O)[C@H](C)N)cc21 ; Cl ; [Cl-]] | 4.09 | 504 | 0.66 | B |
| 6.08 | 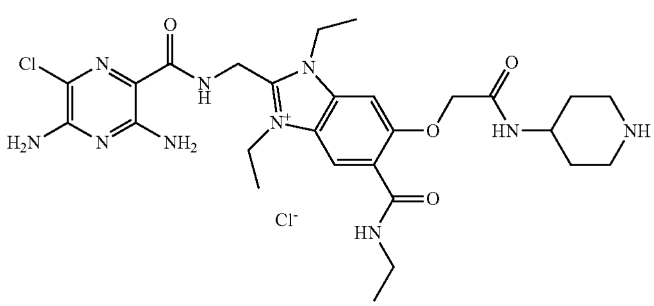 [SMILES: CCNC(=O)c1cc2c(cc1OCC(=O)NC1CCNCC1)n(CC)c(CNC(=O)c1nc(Cl)c(N)nc1N)[n+]2CC ; [Cl-]] | 3.19 | 601 | 0.66 | B |

Example 7.01

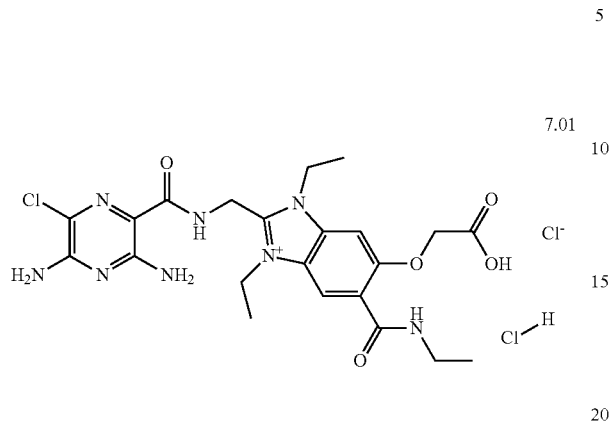

Example 7.01 (750 mg; 1.07 mmol) is stirred in a mixture of TFA (1 ml) and DCM (20 ml) at 70° C. for 5 h. The mixture is evaporated and the residue is taken up in MeOH (2 ml). The precipitate is filtered off and triturated with HCl (4 mol/l in dioxane) and evaporated to dryness.

$C_{22}H_{28}ClN_8O_5 \times Cl \times HCl$ ESI Mass spectrum: m/z=519 [M]+

HPLC analytics: RT=0.72 min (HPLC method B)

The following example compounds are prepared accordingly from the respective ester as indicated. Depending upon conditions applied, the syntheses may yield a TFA salt, a zwitterion or other salt forms.

Example 8.01

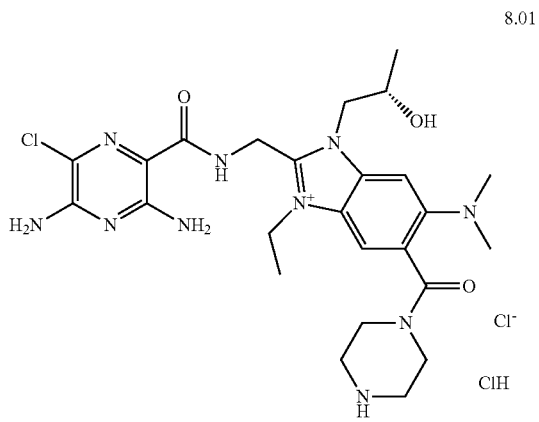

A mixture of example 1.02 (220 mg; 0.285 mmol), HCl (4 mol/l in dioxane; 1.0 ml) and ACN (4.0 ml) is stirred at r.t. for 2 h. Methyl tert-butyl ether (10 ml) is added and the mixture is stirred for 30 min. The precipitate is filtered off, and dried (50° C.).

$C_{25}H_{36}ClN_{10}O_3 \times Cl \times HCl$ ESI Mass spectrum: m/z=559 [M]+

HPLC analytics: RT=0.64 min (HPLC method B)

The following example compounds are prepared accordingly from the respective BOC derivative as indicated. Depending upon conditions applied, the syntheses may yield a TFA salt, a zwitterion or other salt forms.

| Example No. | Structure | Ester applied | M+ | RT | HPLC method |
|---|---|---|---|---|---|
| 7.02 | 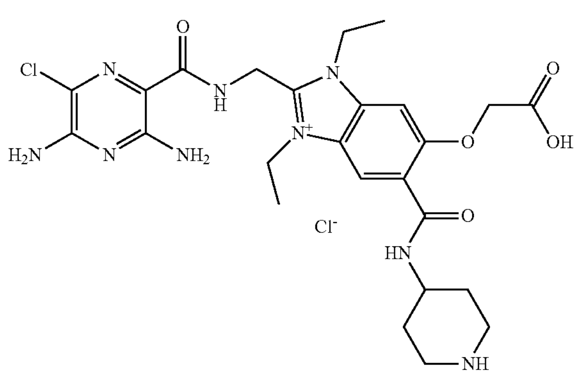 [SMILES: CCn1c(CNC(=O)c2nc(Cl)c(N)nc2N)[n+](CC)c2cc(C(=O)NC3CCNCC3)c(OCC(=O)O)cc21 ; [Cl-]] | 1.13 | 574 | 0.66 | B |

| Example No. | Structure | BOC derivative applied | M+ | RT | HPLC method |
|---|---|---|---|---|---|
| 8.02 | 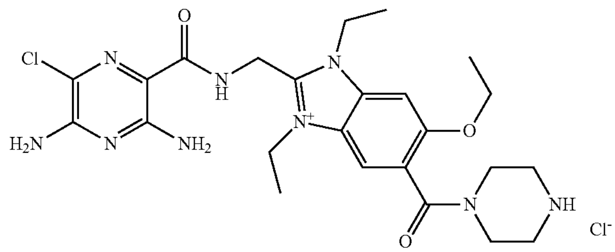 [SMILES: CCOc1cc2c(cc1C(=O)N1CCNCC1)[n+](CC)c(CNC(=O)c1nc(Cl)c(N)nc1N)n2CC ; [Cl-]] | 1.09 | 530 | 0.31 | A |
| 8.03 | 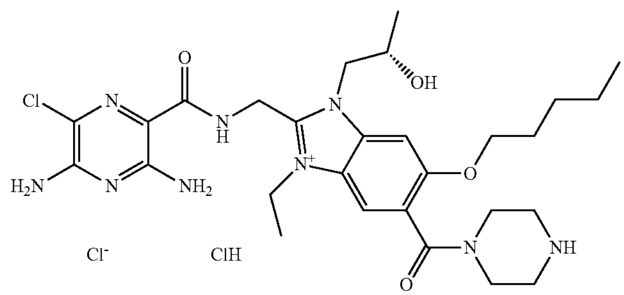 [SMILES: CCCCCOc1cc2c(cc1C(=O)N1CCNCC1)[n+](CC)c(CNC(=O)c1nc(Cl)c(N)nc1N)n2C[C@H](C)O ; [Cl-] ; Cl] | 1.10 | 602 | 0.38 | A |

Example 9.01

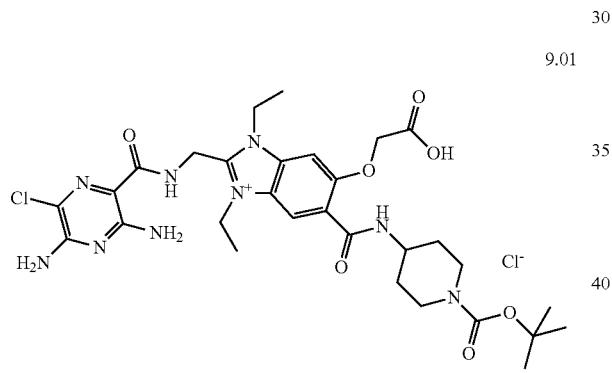

9.01

A mixture of example 7.02 (1.30 g; 2.01 mmol), di-tert-butyl-dicarbonate (449 mg; 2.06 mmol), triethylamine (840 µl; 6.03 mmol), EE (20 ml) and methanol (20 ml) is stirred at r.t. for 3 h. The mixture is evaporated and the crude product is purified by silica gel chromatography (DCM/MeOH 25->50%).

$C_{30}H_{41}ClN_9O_7 \times Cl$ ESI Mass spectrum: m/z=674 [M]+
HPLC analytics: RT=0.86 min (HPLC method B)

Example 10.01

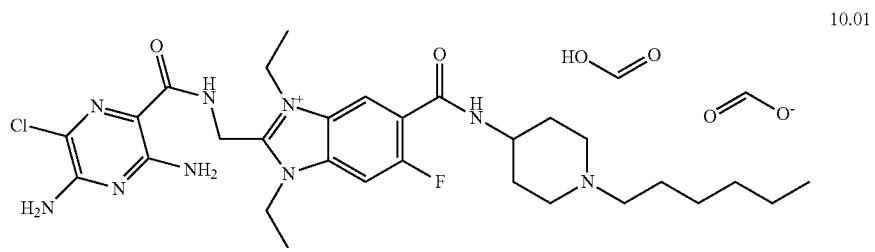

10.01

A mixture of example 6.06 (90.0 mg; 0.136 mmol), 1-iodohexane (34.5 mg; 0.163 mmol), potassium carbonate (20.6 mg; 0.149 mmol), ACN (10 ml) and DMF (1 ml) is stirred at 50° C. overnight. The mixture is evaporated and the crude product is purified by RP-HPLC (modifier: formic acid).

$C_{29}H_{42}ClFN_9O_2 \times CH_2O_2 \times CHO_2$ ESI Mass spectrum: m/z=602 [M]+

HPLC analytics: RT=3.33 min (HPLC method C)

Analytical Methods and Preparative Chromatography

As a rule, $^1$H-NMR and mass spectra have been obtained for the compounds prepared. Mass peaks given (e.g. (M+H)+, (M+HCOO)—) refer to monoisotopic molecular weight. $R_f$ values from TLC are determined using ready-made silica gel 60 TLC plates $F_{254}$ (E. Merck, Darmstadt, Item no. 1.05714) without chamber saturation or using ready-made aluminium oxide 60 $F_{254}$ TLC plates (E. Merck, Darmstadt, Item no. 1.05713) without chamber saturation. The ratios given for the eluents relate to units by volume of the solvent in question. The units by volume for $NH_3$ relate to a concentrated solution of $NH_3$ in water. For silica gel chromatographic purifications, silica gel from Millipore (MATREX™, 35-70 my) is used.

Preparative Thin Layer Chromatography (TLC):

Preparative TLC plates from Merck (PLC Silica gel 60 $F_{254+366}$, 2 mm) are used. Product containing bands are scraped off and the resulting product-on-silica powder is extracted with DCM, methanol or a mixture thereof (depending on product solubility). Silica is filtered off and the filtrate is evaporated to dryness to yield the purified compound.

Preparative HPLC:

Stationary phase (unless stated otherwise): XBridge C18; 10 μm or SunFire C18; 10 μm (both from waters, www.waters.com)

Analytical HPLC/MS Methods

The HPLC retention times given are measured under the following parameters.

| HPLC method A Column: SunFire C18, 2.1 × 30 mm, 2.5 μm (Waters) | | | | |
|---|---|---|---|---|
| Gradient time [min] | % Sol [H2O, 0.1% TFA] | % Sol [ACN] | Flow [ml/min] | Temp [° C.] |
| 0.00 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

| HPLC method B Column: SunFire, 3 × 30 mm, 2.5 μm (Waters) | | | | |
|---|---|---|---|---|
| Gradient time [min] | % Sol [H2O, 0.1% TFA] | % Sol [ACN] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| HPLC method C | |
|---|---|
| Column: | Atlantis dC18 5 μm 4.6 × 50 mm, Temp 35° C. |
| Mobile phase: | A = H2O 90% + 10% CH3CN + CF3COOH 0.05% B = CH3CN 90% + 10% H2O |

| HPLC method C | | | |
|---|---|---|---|
| Time in min | % A | % B | flow rate in ml/min |
| 0.00 | 100 | 0 | 1.3 |
| 0.70 | 100 | 0 | 1.3 |
| 4.5 | 0 | 100 | 1.3 |
| 5.80 | 0 | 100 | 1.3 |
| 6.00 | 100 | 0 | 1.3 |

| HPLC method E Column: Sunfire C18 3.0 × 30 mm, 2.5 μm (Waters) | | | | |
|---|---|---|---|---|
| Gradient Time [min] | % Sol [H2O 0.1% TFA] | % Sol [Acetonitrile] | Flow [ml/min] | Temp [° C.] |
| 0.0 | 98.0 | 2.0 | 2.0 | 60.0 |
| 1.2 | 0.0 | 100.0 | 2.0 | 60.0 |
| 1.4 | 0.0 | 100.0 | 2.0 | 60.0 |

| HPLC method F | |
|---|---|
| Column: | BEH C18 1.7 μm 2.1 × 50 mm, Temp 35° C. |
| Mobile phase: | A = H2O 90% + CH3CN 10% + NH4COOH 5 mM B = CH3CN 90% + H2O 10% |

| Time in min | % A | % B | flow rate in mL/min |
|---|---|---|---|
| 0.00 | 100 | 0 | 0.70 |
| 1.20 | 0 | 100 | 0.70 |
| 1.45 | 0 | 100 | 0.70 |
| 1.55 | 100 | 0 | 0.70 |
| 1.75 | 100 | 0 | 0.70 |

| HPLC method G Column: XBridge BEH C18, 2.1 × 30 mm, 1.7 μm (Waters) | | | | |
|---|---|---|---|---|
| Gradient time [min] | % Sol [H2O, 0.1% TFA] | % Sol [ACN] | Flow [ml/min] | Temp [° C.] |
| 0.00 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

| HPLC method H Column: XSELECT HSS PFP, 2.1 × 30 mm, 1.8 μm (Waters) | | | | |
|---|---|---|---|---|
| Gradient/Solvent Time [min] | % Sol [H2O, 0.1% TFA] | % Sol [Acetonitril] | Flow [ml/min] | Temp [° C.] |
| 0.0 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

| HPLC method I Column: XBridge C18, 3 × 30 mm, 2.5 μm (Waters) | | | | |
|---|---|---|---|---|
| Gradient/Solvent Time [min] | % Sol [H2O, 0.1% TFA] | % Sol [Acetonitril] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |

-continued

HPLC method I
Column: XBridge C18, 3 × 30 mm, 2.5 μm (Waters)

| Gradient/Solvent Time [min] | % Sol [H2O, 0.1% TFA] | % Sol [Acetonitril] | Flow [ml/min] | Temp [° C.] |
|---|---|---|---|---|
| 1.25 | 0 | 100 | 3 | 60 |
| 1.40 | 0 | 100 | 3 | 60 |

HPLC method L
Column: Sunfire C18_3.0 × 30 mm_3.5 μm (Waters)

| Gradient Time [min] | % Sol [H2O 0.1% TFA] | % Sol [Acetonitrile] | Flow [ml/min] | Temp [° C.] |
|---|---|---|---|---|
| 0.0 | 98.0 | 2.0 | 2.0 | 60.0 |
| 0.3 | 98.0 | 2.0 | 2.0 | 60.0 |
| 1.5 | 0.0 | 100.0 | 2.0 | 60.0 |
| 1.6 | 0.0 | 100.0 | 2.0 | 60.0 |

The following abbreviations are used above and hereinafter:

ACN Acetonitrile
BOC tert-Butoxycarbonyl
Cbz Carbobenzyloxy
CH Cyclohexane
DCM Dichloromethane
DIPEA Diisopropyl-ethylamine
DMAP 4-Dimethylaminopyridine
DMF N,N-Dimethylformamide
DPPF 1,1'-Bis(diphenylphosphino)ferrocene
EDC 1-Ethyl-3-(3-dimethylaminopropyl)carbodiimide hydrochloride
EE Ethyl acetate
Eq. Molar equivalent
ESI Electrospray ionization
h hour
HATU O-(7-Azabenzotriazol-1-yl)-N,N,N',N'-tetramethyl-uronium hexafluorophosphate
HCl Hydrochloric acid
KOH Potassium hydroxide
l liter
LiHMDS Lithium bis(trimethylsilyl)amide
M mol/l
Min minutes
Mp melting point
NaOH Sodium hydroxide
n.d. not determined
NMP N-Methylpyrrolidone
Pd/C palladium on charcoal
r.t. ambient temperature (about 20° C.)
RT retention time
TBME Methyl tert-butyl ether
TBTU 2-(1H-Benzotriazol-1-yl)-1,1,3,3-tetramethyluro-nium-tetrafluoroborate
TEA Triethylamine
TFA Trifluoroacetic acid
THF Tetrahydrofurane
TLC Thin Layer Chromatography
TMS Trimethylsilyl Pharmacological Test Method The $IC_{50}$ values of the example compounds given above were determined in the Ussing Chamber assay.

Ussing Chamber: Mouse kidney M-1 cells were cultivated in DMEM containing 5% FCS and 5 μM dexamethasone for 10 to 12 days on polyester transwell filters. Filters were inserted into a teflon-coated well-plate which fit into the ussing chamber system. Prior to measurement the medium of M-1 cells was replaced with Caco-2 transport buffer (Invitrogen, Germany). During measurements, the Ussing chamber temperature was kept at 37° C. Short circuit currents (I_sc) were measured in the voltage-clamp mode with the software package Lab View for data acquisition and analysis. The transepithelial electrical resistance (TEER) was determined by the application of voltage steps of ±5 mV every 5 sec. Compounds were administered at a final concentration of 3 μM or at increasing concentrations (1-3-10 μM) to the apical solution. At the end of each experiment the amiloride sensitive I_SC was measured by adding 3 μM amiloride to the apical compartment. Results are expressed as inhibition in percent of the amiloride effect or as $IC_{50}$.

With the example compounds given above, the following $IC_{50}$ values were determined in the Ussing Chamber assay:

| Example | 1.01 | 1.02 | 1.03 | 1.04 | 1.05 | 1.06 | 1.07 | 1.08 | 1.09 | 1.10 | 1.11 | 1.12 |
|---|---|---|---|---|---|---|---|---|---|---|---|---|
| $IC_{50}$ [nM] | 2 | 25 | 5 | 2 | 1 | 2 | 3 | 1 | 7 | 52 | 10 | 8 |
| Example | 1.13 | 1.14 | 1.15 | 1.16 | 2.01 | 3.02 | 3.03 | 3.04 | 3.05 | 3.06 | 3.07 | 3.08 |
| $IC_{50}$ [nM] | 9 | 3 | 8 | 11 | 1 | 0.4 | 0.3 | 0.6 | 2 | 1 | 1 | 0.4 |
| Example | 3.09 | 3.10 | 3.13 | 3.14 | 3.15 | 3.17 | 3.18 | 3.19 | 3.20 | 3.21 | 3.22 | 3.23 |
| $IC_{50}$ [nM] | 0.2 | 1 | 2 | 0.4 | 1 | 15 | 4 | 9 | 15 | 9 | 10 | 8 |
| Example | 3.24 | 3.25 | 4.01 | 4.02 | 4.03 | 4.04 | 4.05 | 4.06 | 4.07 | 4.08 | 4.09 | 4.10 |
| $IC_{50}$ [nM] | 0.1 | 1 | 1 | 2 | 0.4 | 1 | 0.4 | 0.3 | 1 | 2 | 1 | 1 |
| Example | 4.11 | 4.12 | 4.13 | 4.14 | 4.15 | 4.16 | 4.17 | 4.18 | 5.01 | 5.02 | 6.01 | 6.02 |
| $IC_{50}$ [nM] | 2 | 2 | 4 | 19 | 34 | 2 | 23 | 19 | 5 | 3 | 14 | 1 |
| Example | 6.03 | 6.04 | 6.05 | 6.06 | 6.07 | 6.08 | 7.01 | 7.02 | 8.01 | 8.02 | 8.03 | 9.01 |
| $IC_{50}$ [nM] | 8 | 0.4 | 1 | 0.4 | 0.4 | 1 | 38 | 29 | 6 | 1 | 8 | 9 |
| Example | 10.01 | | | | | | | | | | | |
| $IC_{50}$ [nM] | 1 | | | | | | | | | | | |

Permeability in CALU-3 Cells:

Permeability measurements across polarized, confluent CALU-3 cell monolayers grown on permeable filter supports are used to provide information on the potential of a compound to pass the lung epithelium. Apparent permeability coefficients (Papp) of the compounds across the CALU-3 cell monolayers are measured (pH 7.4, 37° C.) in apical-to-basal (AB) and basal-to-apical (BA) transport direction. AB permeability (Papp, AB) represents drug absorption from the lung lumen into the blood and BA permeability (Papp, BA) drug transport from the blood into the lung lumen mainly via passive permeability since Calu-3 cells as well as lung epithelial cells do not express efflux transporters like P-gp, while uptake transporters may be expressed.

CALU-3 cells ($1-2\times10^5$ cells/1 $cm^2$ area) are seeded on filter inserts (Costar transwell polycarbonate filters, 0.4 μm pore size) and cultured (for 10-12 days DMEM) until tight monolayers are formed. Compounds of interest are dissolved in appropriate solvent (DMSO, 10 mM stock solution). Stock solutions are diluted with HTP-4 buffer (128.13 mM NaCl, 5.36 mM KCl, 1 mM MgSO$_4$, 1.8 mM CaCl$_2$, 4.17 mM NaHCO3, 1.19 mM Na2HPO4×7H2O, 0.41 mM NaH2PO4×H2O, 15 mM HEPES, 20 mM glucose, 0.25% BSA, pH 7.4) to prepare the transport solutions (10 μM compound, final DMSO<=0.5%). The transport solution (TL) is applied to the apical or basolateral donor side for measuring A-B or B-A permeability (3 filter replicates), respectively. The receiver side contains the same buffer as the donor side. After 30 min of accommodation, samples are collected at the start t0=0 min and at the end of the experiment tn=90 min from the donor and at 0, 30, 60, and 90 min also from the receiver chamber. Volume removed is replenwashed by HTP-4 buffer. The compound concentration in the samples is measured by HPLC-MS/MS or scintillation counting. The permeability coefficient (Papp) and efflux ratio are calculated according to: Papp [cm/s]=(concentration receiver [nM]*volume receiver [mL]/time interval [sec])*(1/filter area)*(1/donor concentration [nM]).

With example compounds given above, the following permeability values were determined in the CALU-3 cells assay:

| Example | 1.01 | 1.02 | 1.05 | 1.08 | 1.12 | 1.15 | 3.05 | 3.06 | 3.17 |
|---|---|---|---|---|---|---|---|---|---|
| Papp, AB [$10^{-6}$ cm/s] | 0.04 | 0.08 | 0.1 | 0.08 | 0.1 | 0.2 | 0.2 | 0.02 | 0.08 |
| Papp, BA [$10^{-6}$ cm/s] | 0.06 | 0.1 | 0.01 | 0.2 | 0.04 | 0.08 | 0.3 | 0.03 | 0.08 |
| Example | 4.01 | 4.14 | 4.15 | 5.01 | | 5.02 | | 6.02 | 10.01 |
| Papp, AB [$10^{-6}$ cm/s] | 0.2 | 0.3 | 0.3 | 0.3 | | 0.09 | | 0.08 | 0.3 |
| Papp, BA [$10^{-6}$ cm/s] | 0.2 | 0.2 | 0.3 | 0.06 | | 0.1 | | 0.06 | 0.3 |

Indications

As has been found, the compounds of formula (I) are characterised by their wide range of applications in the therapeutic field. Particular mention should be made of those applications for which the compounds according to the invention of formula (I) are preferably suited on account of their pharmaceutical efficacy as ENaC inhibitors. Examples include respiratory diseases or complaints, or allergic diseases of the airways.

Particular mention should be made of the prevention and treatment of diseases of the airways and of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, paediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Particularly preferably the present invention relates to the use of compounds of formula (I) for preparing a pharmaceutical composition for the treatment of inflammatory or obstructive diseases of the upper and lower respiratory tract including the lungs, such as for example allergic rhinitis, chronic rhinitis, bronchiectasis, cystic fibrosis, COPD, chronic bronchitis, chronic sinusitis and asthma.

It is most preferable to use the compounds of formula (I) for the treatment of inflammatory and obstructive diseases such as COPD, chronic bronchitis, chronic sinusitis, asthma, cystic fibrosis, particularly COPD, chronic bronchitis, asthma and cystic fibrosis.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Combinations

The compounds of formula (I) may be used on their own or in conjunction with other active substances of formula (I) according to the invention. If desired the compounds of formula (I) may also be used in combination with other pharmacologically active substances.

Therefore the invention further relates to medicament combinations which preferably contain, besides one or more compounds of formula (I) or a salt thereof, as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators, or double or triple combinations thereof.

Formulations

Suitable forms for administration are for example inhalable powders or aerosols. The content of the pharmaceutically effective compound(s) in each case should be in the range from 0.2 to 50 wt %, preferably 0.5 to 25 wt % of the total composition, i.e. in amounts which are sufficient to achieve the dosage range specified hereinafter.

Administered by inhalation the active substance combination may be given as a powder, as an aqueous or aqueous-ethanolic solution or using a propellant gas formulation.

Preferably, therefore, pharmaceutical formulations are characterised in that they contain one or more compounds of formula (I) according to the preferred embodiments above.

It is also preferred if the compounds of formula (I) are administered by inhalation, particularly preferably if they are administered once or twice a day. For this purpose, the compounds of formula (I) have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also include concentrates or sterile ready-to-use inhalable solutions. The preparations which may be used according to the invention are described in more detail in the next part of the specification.

Inhalable Powders

If the active substances of formula (I) are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain a compound of formula (I) dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula (I) according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finwashed pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, a compound according to the invention and one or more combination partners selected from those described above.

What we claim:

1. A compound of formula (I), or a tautomer thereof, or a pharmacologically acceptable acid addition salt of the compound or the tautomer,

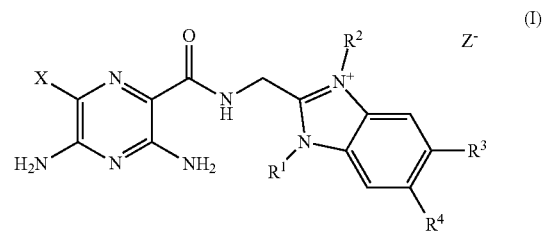

wherein $R^1$ and $R^2$ are independently selected from $C_1$-$C_6$-alkyl, wherein $C_1$-$C_6$-alkyl may be substituted by hydroxy, $C_1$-$C_4$-alkoxy, or $C_3$-$C_7$-cycloalkyl;

X is Cl or Br; and $Z^-$ is chloride, bromide, iodide, hydroxide, hydrogensulfate, sulfate, nitrate, phosphate, formate, acetate, trifluoroacetate, fumarate, citrate, tartrate, oxalate, succinate, mandelate, methanesulfonate or p-toluenesulfonate; or Z— may be absent if the remaining compound of formula (I) carries at least one negatively charged substituent $R^3$ or $R^4$;

wherein the compound of formula (I) is characterized by a topological polar surface area value (TPSA) of at least 145; and wherein at least one of $R^3$ or $R^4$ is independently selected from a substituent —C(O)$NR_aR_b$, —CH$_2$—C(O)$NR_aR_b$, or —O—CH$_2$—C(O)$NR_aR_b$, wherein $R^a$ is H, methyl, ethyl, hydroxyethyl, or hydroxypropyl, and $R^b$ is selected from $C_1$-$C_2$-alkoxy-$C_2$-$C_3$-alkyl, amino-$C_2$-$C_3$-alkyl, 4-piperidinyl, 1-acetyl-4-piperidinyl, dimethylamino-$C_2$-$C_3$-alkyl, (3-hydroxy-1-pyridinylium)-$C_2$-$C_3$-alkyl, acetylamino-$C_2$-$C_3$-alkyl, 1-($C_1$-$C_6$-alkyl)-4-piperidinyl, 1-($C_1$-$C_4$-alkoxy-carbonyl)-4-piperidinyl, $C_1$-$C_3$-alkylsulfonylamino-($C_2$-$C_3$-alkyl), 3-hydroxy-5-pyridyl, 1-(ethylaminocarbonylmethyl)-4-piperidinyl, 3-benzyloxy-5-pyridyl, 3-hydroxy-6-methyl-2-pyridylmethyl and 3-hydroxy-2-pyridylmethyl-, or wherein $R^a$ and $R^b$ together with the nitrogen atom they are attached to form a group selected from 1-(2-pyridyl)-4-piperazinyl, 1-($C_1$-$C_4$-alkoxycarbonyl)-4-piperazinyl, 1-(1-morpholinyl-carbonyl)-4-piperazinyl, 1-(2-pyridylacetyl)-4-piperazinyl, 1-(3-hydroxy-5-pyridycarbonyl)-4-piperazinyl, and 1-acetyl-4-piperazinyl, or wherein at least one of $R^3$ or $R^4$ is independently selected from hydroxycarbonyl, (hydroxycarbonyl)methoxy, N-morpholinylcarbonyl, 3,4-dihydroxypyrrolidin-1-yl, 4-hydroxytetrahydrofur-3-yloxy, tert-butoxycarbonylmethoxy, (3-hydroxy-1-pyridinylium)-$C_2$-$C_3$-alkoxy, $(CH_3)_3N^+$—$(CH_2)_3$—$P(O)(O^-)$—O—$(CH_2)_2$—O—, ($C_1$-$C_5$-alkylcarbonyl)(($CH_3)_2P(O)CH_2$)N—$(CH_2)_2$—O—, 1-piperazinylcarbonyl-$(CH_2)_m$—, or 1-methyl-4-piperazinyl-carbonyl-$(CH_2)_m$—, wherein m is 0, 1 or 2, or wherein at least one of $R^3$ or $R^4$ is independently selected from one of the following substituents:

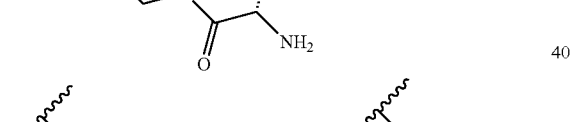

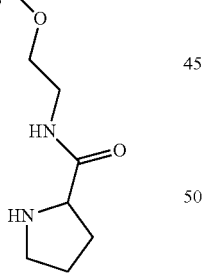

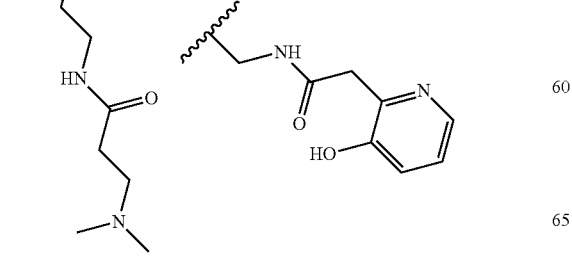

-continued

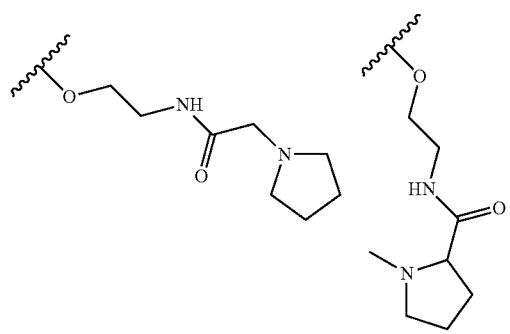

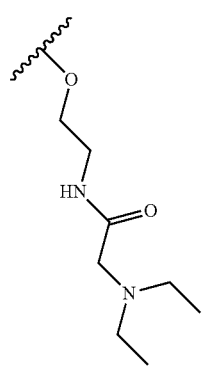

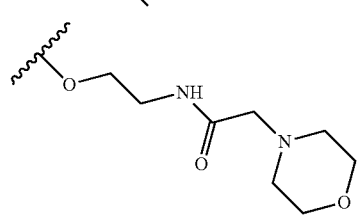

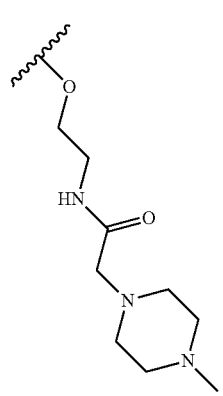

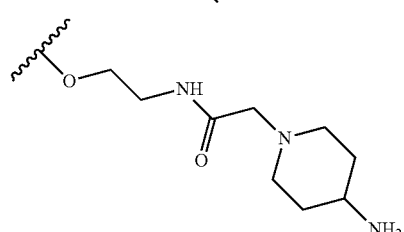

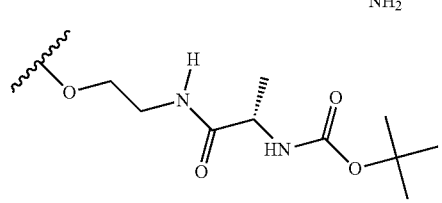

-continued

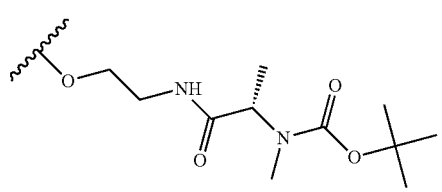

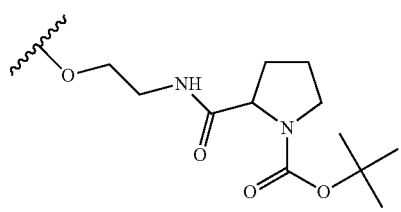

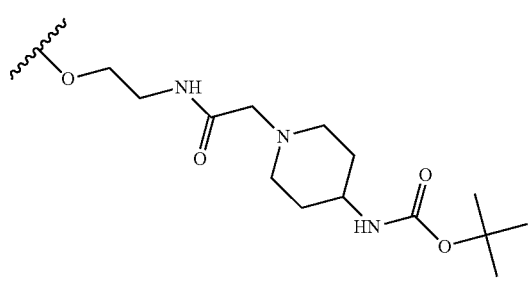

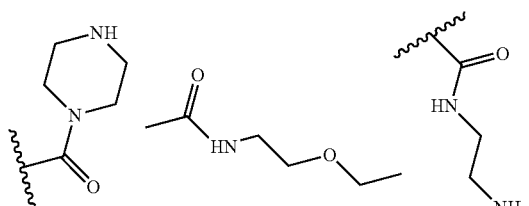

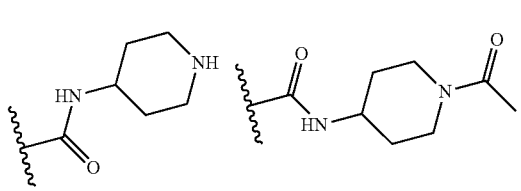
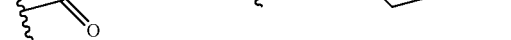

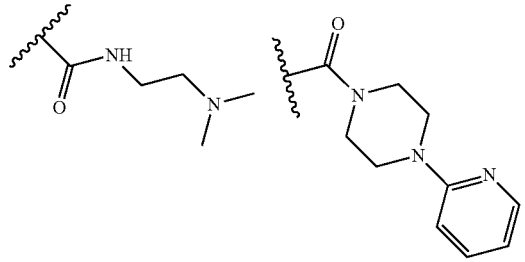

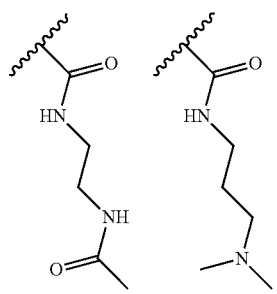

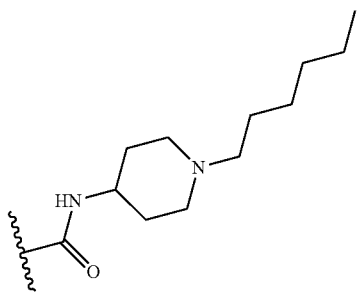

wherein ⌇ denotes the point of attachment; and the remaining substituent $R^3$ or $R^4$ may additionally be selected from H, F, $C_1$-$C_6$-alkoxy, di($C_1$-$C_6$-alkyeamino, $C_1$-$C_6$-alkylaminocarbonyl, $C_1$-$C_6$-alkylaminocarbonylmethoxy, di($C_1$-$C_6$-alkyl)aminocarbonyl, and N-morpholino;

provided that if one of $R^3$ or $R^4$ is

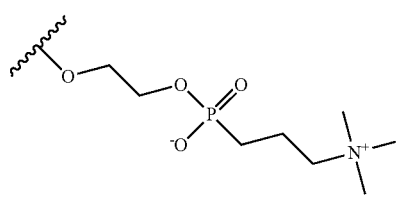

at least one of $R^1$ or $R^2$ is $C_3$-$C_7$-cycloalkyl-$C_1$-$C_6$-alkyl; and provided that if one of $R^3$ or $R^4$ is N-morpholinocarbonyl the remaining substituent $R^3$ or $R^4$ is different from H, F or $C_1$-$C_6$-alkylaminocarbonyl; and provided that at least one of $R^3$ or $R^4$ is different from H, hydroxycarbonyl, (hydroxycarbonyl)methoxy and tert-butoxycarbonylmethoxy.

2. The compound of formula (I) according to claim 1, or a tautomer thereof or a pharmacologically acceptable acid addition salt of the compound or the tautomer, wherein at least one of $R^3$ or $R^4$ is independently selected from a substituent —C(O)NR$_a$R$_b$ selected from

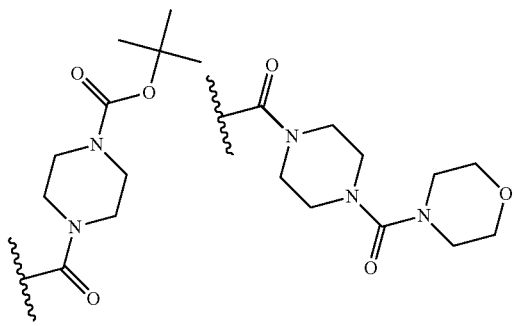

-continued

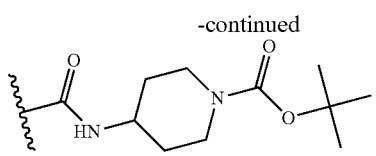

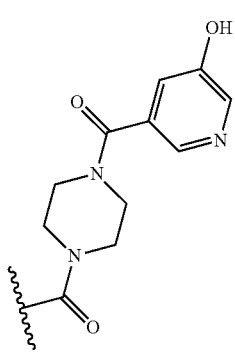

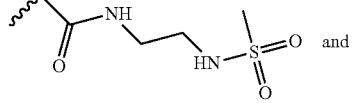

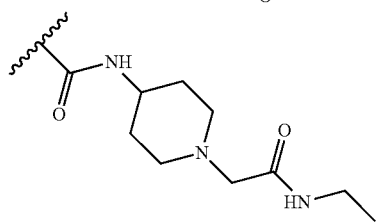

wherein ⌁ denotes the point of attachment.

3. The compound of formula (I) according to claim 1, or a tautomer thereof or a pharmacologically acceptable acid addition salt of the compound or the tautomer, wherein at least one of $R^3$ or $R^4$ is independently selected from a substituent —$CH_2$—$C(O)NR_aR_b$, selected from wherein ⌁ denotes the point of attachment.

4. The compound of formula (I) according to claim 1, or a tautomer thereof or a pharmacologically acceptable acid addition salt of the compound or the tautomer, wherein at least one of $R^3$ or $R^4$ is independently selected from a substituent —O—$CH_2$—$C(O)NR_aR_b$ selected from

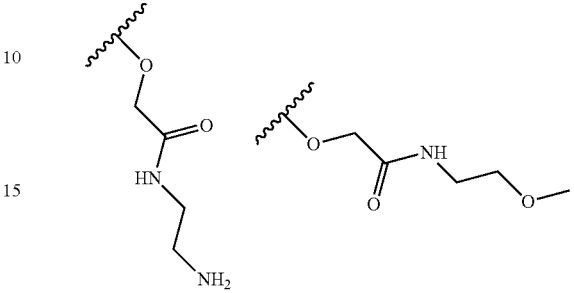

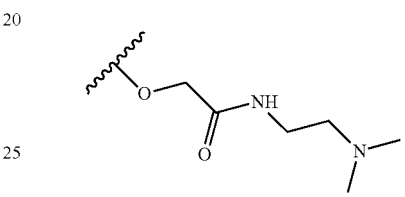

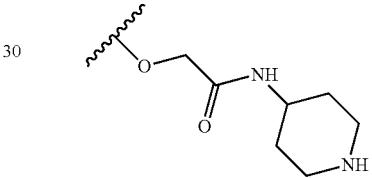

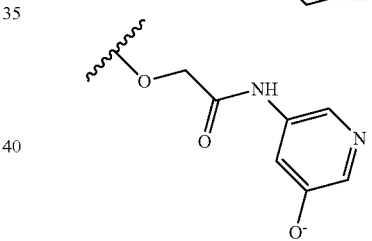

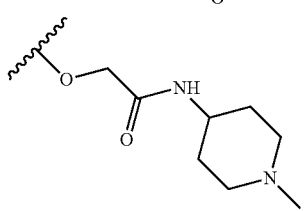

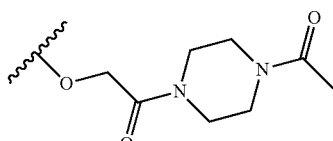

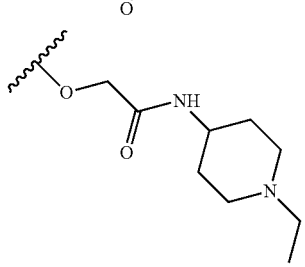

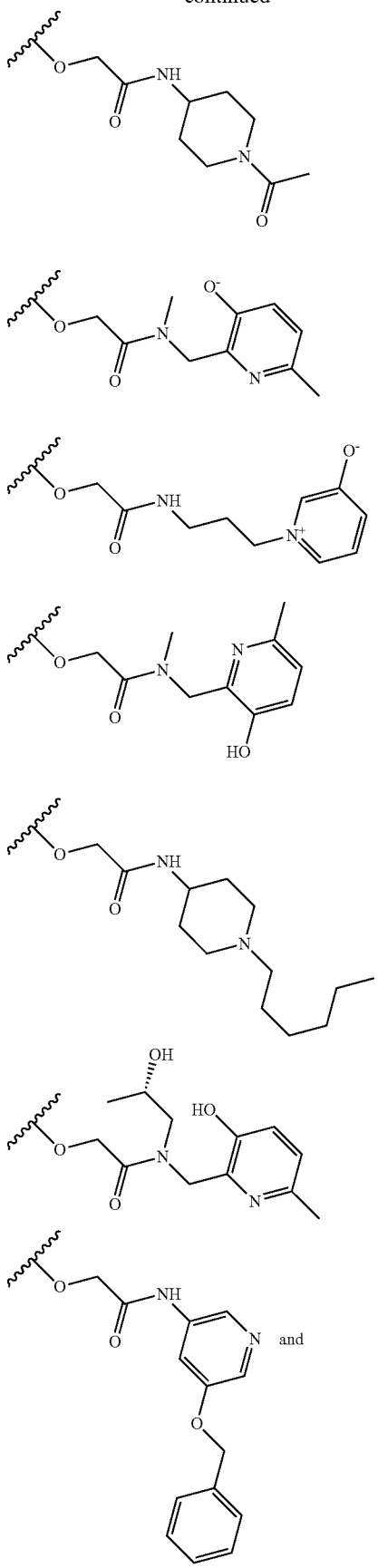

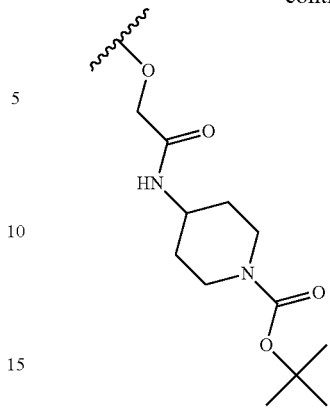

wherein ⌒ denotes the point of attachment.

5. The compound of formula (I) according to claim 1, or a tautomer thereof or a pharmacologically acceptable acid addition salt of the compound or the tautomer, wherein one of $R^3$ or $R^4$ is selected from (3-hydroxy-1-pyridinylium) ethoxy, 2-(N-(dimethylphosphinoylmethyl)-N-(3-methylbutanoyl)amino)ethyloxy, 2-(N-(dimethylphosphinoylmethyl)-N-(hexanoyl)amino)ethyloxy, piperazin-1-ylcarbonyl, or 1-methylpiperazin-4-yl-carbonyl-($CH_2$)—.

6. The compound of formula (I) according to claim 1, or a tautomer thereof or a pharmacologically acceptable acid addition salt of the compound or the tautomer, wherein $R^1$ and $R^2$ are independently selected from methyl, ethyl, n-propyl, 2-hydroxyethyl, 2-hydroxypropyl, cyclopropylmethyl, and cyclohexylmethyl.

7. The compound of formula (I) according to claim 1, or a tautomer thereof or a pharmacologically acceptable acid addition salt of the compound or the tautomer, wherein $Z^-$ is chloride, iodide, formate or trifluoroacetate, or $Z^-$ may be absent if the remaining compound of formula (I) carries a negatively charged substituent $R^3$ or $R^4$.

8. The compound of formula (I) according to claim 1, or a tautomer thereof or a pharmacologically acceptable acid addition salt of the compound or the tautomer, wherein the remaining substituent $R^3$ or $R^4$ is selected from H, F, ethoxy, n-pentyloxy, dimethylamino, ethylaminocarbonyl, ethylaminocarbonylmethoxy, n-hexyl(methyl)aminocarbonyl, and N-morpholino.

9. A method for treating a disease comprising administering an effective amount of a compound of formula (I) according to claim 1 or a tautomer thereof or a pharmacologically acceptable acid addition salt of the compound or the tautomer, wherein the disease is selected from the group consisting of a respiratory disease, a respiratory complaint, and an allergic disease of the airways.

10. A method for treating a disease, comprising administering an effective amount of a compound of formula (I) according to claim 1 or a tautomer thereof or a pharmacologically acceptable acid addition salt of the compound or the tautomer, wherein the disease is selected from the group consisting of chronic bronchitis, acute bronchitis, bronchitis caused by bacterial or viral infection or fungi or helminths, allergic bronchitis, toxic bronchitis, chronic obstructive bronchitis (COPD), asthma (intrinsic or allergic), pediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases, alveolitis, hyperreactive airways, nasal polyps, pulmonary oedema, pneumonitis of different origins, and dry eyes.

11. A pharmaceutical composition comprising a compound of formula (I) according to claim 1 or a tautomer thereof or a pharmacologically acceptable acid addition salt of the compound or the tautomer and a pharmaceutically acceptable carrier.

12. A pharmaceutical composition comprising a compound of formula (I) according to claim 1 or a tautomer thereof or a pharmacologically acceptable acid addition salt of the compound or the tautomer, and one or more compounds selected from an ENaC inhibitor, a betamimetic, an anticholinergic, a corticosteroid, a PDE4-inhibitor, an LTD4-antagonist, a EGFR-inhibitor, a dopamine agonist, an H1 antihistamine, a PAF-antagonist, a MAP-kinase inhibitor, an MPR4-Inhibitor, an iNOS-Inhibitor, a SYK-Inhibitor, a cystic fibrosis transmembrane regulator (CFTR) potentiator, and double or triple combinations thereof.

\* \* \* \* \*